(12) United States Patent
Wickens et al.

(10) Patent No.: US 7,476,742 B2
(45) Date of Patent: Jan. 13, 2009

(54) INDANE ACETIC ACID DERIVATIVES AND THEIR USE AS PHARMACEUTICAL AGENTS

(75) Inventors: Philip Wickens, Wallingford, CT (US); Louis-David Cantin, Hamden, CT (US); Ellalahewage Kumarasinghe, Hamden, CT (US); Chih-Yuan Chuang, Orange, CT (US); Sidney X. Liang, Bethany, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 378 days.

(21) Appl. No.: 10/506,270

(22) PCT Filed: Apr. 16, 2003

(86) PCT No.: PCT/US03/11725

§ 371 (c)(1),
(2), (4) Date: Aug. 30, 2004

(87) PCT Pub. No.: WO03/089418

PCT Pub. Date: Oct. 30, 2003

(65) Prior Publication Data

US 2005/0107392 A1    May 19, 2005

Related U.S. Application Data

(60) Provisional application No. 60/373,048, filed on Apr. 16, 2002.

(51) Int. Cl.
*A61K 31/421* (2006.01)
*C07D 263/32* (2006.01)

(52) U.S. Cl. .................. 548/236; 548/203; 548/235; 514/365; 514/370; 514/374

(58) Field of Classification Search ................ 548/203, 548/235, 236
See application file for complete search history.

(56) References Cited

U.S. PATENT DOCUMENTS 6,828,335 B2 * 12/2004 Lowe et al. .................. 514/340
7,112,597 B2 *  9/2006 Lowe et al. .................. 514/365

FOREIGN PATENT DOCUMENTS

| WO | 0116120 | 3/2001 |
| WO | 02018335 | 3/2002 |
| WO | 03011842 | 2/2003 |

* cited by examiner

*Primary Examiner*—Laura L. Stockton
(74) *Attorney, Agent, or Firm*—Edwards Angell Palmer & Dodge, LLP

(57) ABSTRACT

This invention relates to novel indane acetic acid derivatives which are useful in the treatment of diseases such as diabetes, obesity, hyperlipidemia, and atherosclerotic diseases and to pharmaceutical compositions containing these compounds.

13 Claims, No Drawings

INDANE ACETIC ACID DERIVATIVES AND THEIR USE AS PHARMACEUTICAL AGENTS

This application claims benefit of U.S. Provisional Application Ser. No. 60/373,048, filed on Apr. 16, 2002, the contents of which are incorporated herein by reference in their entirety.

FIELD OF THE INVENTION

This invention is directed to the use of indane acetic acid derivatives and pharmaceutical compositions useful in the treatment of disease such as diabetes, obesity, hyperlipidemia, and atherosclerotic disease. The invention is also directed to intermediates useful in preparation of said indane acetic derivatives and to methods of preparation.

BACKGROUND OF THE INVENTION

Non-insulin dependent diabetes mellitus (NIDDM), or Type II diabetes, is the more common form of diabetes, with 90-95% of hyperglycemic patients experiencing this form of the disease. In Type II diabetes, there appears to be a reduction in the pancreatic β-cell mass, several distinct defects in insulin secretion, or a decrease in tissue sensitivity to insulin. The symptoms of this form of diabetes include fatigue, frequent urination, thirst, blurred vision, frequent infections and slow healing of sores, diabetic nerve damage, retinopathy, micro and macro blood vessel damage, and heart and renal disease.

Resistance to the metabolic actions of insulin is one of the key features of Type II diabetes. Insulin resistance is characterized by impaired uptake and utilization of glucose in insulin-sensitive target organs, for example, adipocytes and skeletal muscle, and by impaired inhibition of hepatic glucose output. Functional insulin deficiency, insulin resistance in the periphery, and the failure of insulin to suppress hepatic glucose output results in fasting hyperglycemia. Pancreatic β-cells compensate for the insulin resistance by secreting increased levels of insulin. However, the β-cells are unable to maintain this high output of insulin, and eventually, the glucose-induced insulin secretion falls, leading to the deterioration of glucose homeostasis and to the subsequent development of overt diabetes. Hyperinsulinemia is also linked to insulin resistance, hypertriglyceridemia, low high-density lipoprotein (HDL) cholesterol, and increased plasma concentration of low-density lipoproteins (LDL). The association of insulin resistance and hyperinsulinemia with these metabolic disorders has been termed "Syndrome X," and has been strongly linked to an increased risk of hypertension and coronary artery disease.

Obesity is an excessive accumulation of adipose tissue. Excess adipose tissue is associated with the development of serious medical conditions, for example, Type II diabetes, hypertension, coronary artery disease, hyperlipidemia, obesity, and certain malignancies. The adipocyte may also influence glucose homeostasis through the production of tumor necrosis factor α (TNFα) and other molecules.

Atherosclerotic disease is known to be caused by a number of factors, for example, hypertension, diabetes, low levels of high-density lipoprotein (HDL), and high levels of low-density lipoprotein (LDL). Atherosclerotic diseases include cardiovascular disease, coronary heart disease (CHD), cerebrovascular disease, and peripheral vessel disease. Coronary heart disease includes CHD death, myocardial infarction, and coronary revascularization. Cerebrovascular disease includes ischemic or hemorrhagic stroke, and transient ischemic attacks.

Accordingly, despite the presence of some pharmaceuticals that are used to treat these diseases, there remains a need for new pharmaceuticals that are both safe and effective agents for the treatment of disease, and for useful methods to prepare them.

The present invention relates to compounds which are useful in the treatment of diabetes and related disorders such as Syndrome X, impaired glucose tolerance, impaired fasting glucose, and hyperinsulinemia; obesity; atherosclerotic disease and related disorders such as hypertriglyceridemia and hypercholesteremia; cardiovascular disease; and cerebrovascular disease.

DESCRIPTION OF THE INVENTION

The present invention encompasses the compounds of Formula (I),

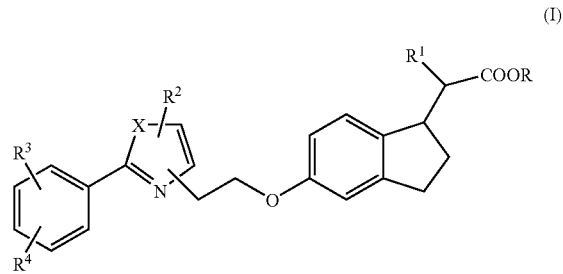

(I)

wherein
R and $R^1$ is H or $C_1$-$C_6$ alkyl;
$R^2$ is H, $C_1$-$C_6$ alkyl, or phenyl which may be unsubstituted or substituted with $R^3$;
$R^3$ is H, halo, $NO_2CF_3$, 2,3-methylenedioxy, 3,4-methylenedioxy, $C_1$-$C_6$alkylthio, $C_1$-$C_6$ alkyl optionally substituted with oxo or hydroxy, $C_1$-$C_6$ alkoxy optionally substituted with fluoro, or carboxy optionally substituted with H or $C_1$-$C_6$ alkyl;
$R^4$ is $C_3$-$C_8$ cycloalkyl,
$C_2$-$C_6$ alkenyl,
$NO_2$,
$CO_2R$,
$N^+(R^5)_3$, where $R^5$ is $C_1$-$C_6$ alkyl optionally substituted with phenyl,
N—(Y—$R^6$)$_n$,
where n=1 or 2,
Y is a bond, —$SO_2$—, —$SO_2NR^7$—, —C(O)—, —C(O)—$NR^7$— or —C(O)O—,
$R^6$ is H, aryl, benzyl, $C_1$-$C_6$ alkoxyalkyl, $C_1$-$C_6$ alkyl, heteroaryl, each of which can be substituted by $R^3$, or
when Y is a bond, two $R^6$ groups may form, together with the N atom to which they are attached, a 3-7 membered heterocyclic ring optionally containing an additional N, S, or O atom, which is optionally substituted by $N(R^7)_2$ or $N^+(R^5)_3$, and
$R^7$ is H, $C_1$-$C_6$ alkyl or phenyl substituted with $R^3$,
or
phenyl, naphthyl, furyl, thienyl, pyrrolyl, tetrahydrofuryl, pyrrolidinyl, pyrrolinyl, tetrahydrothienyl, oxazolyl, thiazolyl, imidazolyl, pyrazolyl, isoxazolyl, isothiazolyl, triazolyl, oxadiazolyl, thiadiazolyl, tetrazolyl, pyridyl, piperidinyl, tetrahydropyranyl, tetrahydrothiopyranyl, pyrimidinyl, pyrazinyl, pyridazinyl, piperazinyl, triazinyl, morpholinyl, benzofuryl, dihydrobenzofuryl, benzothienyl, dihydrobenzothienyl, indolyl, indolinyl, indazolyl, benzoxazolyl, benxothiazolyl, benzimidazolyl, benzisoxazolyl, benzisothiazolyl, benzodioxolyl, quinolyl, isoquinolyl, quinazolinyl, quinoxazolinyl, dihydrobenzopyranyl, dihydrobenzothiopyranyl, or 1,4-benzodioxanyl, each of which is substituted by one or more $R^8$, where $R^8$ is $C_3$-$C_8$ cycloalkyl, $C_2$-$C_6$ alkenyl $NO_2$, $CO_2R$, $N^+(R^7)_3$, or $N-(Y-R^6)_n$, where n=1 or 2; and X is O or S.

The terms identified above have the following meaning throughout:

"$C_1$-$C_6$ alkyl" means straight or branched chain alkyl groups having from one to about six carbon atoms. Such groups include methyl, ethyl, n-propyl, isopropyl, n-butyl, isobutyl, sec-butyl, tert-butyl, n-pentyl, neo-pentyl, 2-pentyl, n-hexyl, 2-hexyl, 3-hexyl, 2,3-dimethylbutyl, and the like.

"$C_2$-$C_6$ alkenyl" means straight or branched chain alkenyl groups having from two to about six carbon atoms and containing one or more double bonds. Such groups include ethenyl, propenyl, isopropenyl, 2-isobutenyl, 4-pentenyl. 5-hexenyl, and the like.

"$C_3$-$C_8$ cycloalkyl" means saturated monocyclic alkyl groups having from 3 to about 8 carbon atoms and includes such groups as cyclopropyl, cyclopentyl, cyclohexyl, and the like.

"$C_1$-$C_6$ alkoxy" means straight or branched chain alkoxy groups having from one to about six carbon atoms and includes such groups as methoxy, ethoxy, n-propoxy, isopropoxy, n-butoxy, isobutoxy, sec-butoxy, tert-butoxy, and the like.

"$C_1$-$C_6$ alkoxyalkyl" means straight or branched chain $C_1$-$C_6$ alkyl group which is further substituted at any available position with a straight or branched chain $C_1$-$C_6$ alkoxy group, which contains in total about six carbon atoms and includes such groups as methoxymethyl, ethoxymethyl, 2-methoxyethyl, n-butoxyethyl, i-propoxymethyl, 1-methoxypropyl, and the like.

"$C_1$-$C_6$ alkythio" means straight or branched chain alkylthio groups having from one to about six carbon atoms and includes such groups as methylthio, ethylthio, n-propylthio, isopropylthio, n-butylthio, isobutylthio, sec-butylthio, tert-butylthio, and the like.

"Halo" means fluoro, chloro, bromo, or iodo.

"Heteroaryl" means a 5- or 6-membered aromatic heterocyclic ring radical containing from 1 to 3 heteroatoms selected from 0-1 oxygen atoms, 0-1 sulfur atoms and 0-3 nitrogen atoms. Such groups include furyl, thienyl, pyrrolyl, oxazolyl, thiazolyl, imidazolyl, pyrazolyl, isoxazolyl, isothiazolyl, triazolyl, oxadiazolyl, thiadiazolyl, pyridyl, pyrimidinyl, pyrazinyl, and pyridazinyl groups, and the like.

When an alkyl, cycloalkyl, alkenyl, or alkoxy group is described as being substituted with fluoro, it may be substituted with one or more fluorine atoms at any available carbon atom up to the perfluoro level.

When an alkyl substituent is described as being substituted by oxo, it means substitution by a doubly bonded oxygen atom, which forms together with the carbon to which it is attached, a carbonyl group —(C=O)—.

When any moiety is described as being substituted, it can have one or more of the indicated substituents that may be located at any available position on the moiety. When there are two or more substituents on any moiety, each substituent may be defined independently of any other substituent and may, accordingly, be the same or different.

The term "optionally substituted" means that the moiety so modified may be unsubstituted or substituted with the identified substituent(s).

$R^2$ may be attached to the heterocyclic moiety of the compound of Formula (I) at either the 4 or 5 position (i.e., at either available carbon atom) and, accordingly, the remaining portion of the molecule will be attached at the remaining available carbon atom.

A salt of a compound of Formula (I) may be prepared in situ during the final isolation and purification of a compound or by separately reacting the purified compound in its free base form with a suitable organic or inorganic acid and isolating the salt thus formed. Likewise, when the compound of Formula (I) contains a carboxylic acid moiety, (e.g., R=H), a salt of said compound of Formula (I) may be prepared by separately reacting it with a suitable inorganic or organic base and isolating the salt thus formed. The term "pharmaceutically acceptable salt" refers to a relatively non-toxic, inorganic or organic acid addition salt of a compound of the present invention (see, e.g., Berge et al., J. Pharm. Sci. 66:1-19, 1977).

Representative salts of the compounds of Formula (I) include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, undecanoate, and the like.

Base salts include, for example, alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups in the conjugate base may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides; aralkyl halides like benzyl and phenethyl bromides, and the like.

The esters of Formula (I) in the present invention are non-toxic, pharmaceutically acceptable esters, for example, alkyl esters such as methyl, ethyl, propyl, isopropyl, butyl, isobutyl, or pentyl esters. Additional esters such as, for example, methyl ester or phenyl-$C_1$-$C_5$ alkyl may be used. The compound of Formula (I) may be esterified by a variety of conventional procedures including reacting the appropriate anhydride, carboxylic acid, or acid chloride with the alcohol group of the Formula (I) compound. The appropriate anhydride may be reacted with the alcohol in the presence of a base to facilitate acylation such as 1,8-bis[dimethylamino]naphthalene or N,N-dimethylaminopyridine. An appropriate carboxylic acid may be reacted with the alcohol in the presence of a dehydrating agent such as dicyclohexylcarbodiimide, 1-[3-dimethylaminopropyl]-3-ethylcarbodiimide, or other water soluble dehydrating agents which are used to drive the reaction by the removal of water, and optionally, an acylation catalyst. Esterification may also be effected using the appropriate carboxylic acid in the presence of trifluoroacetic anhydride and optionally, pyridine, or in the presence of N,N-carbonyldiimidazole with pyridine. Reaction of an acid chloride with the alcohol may be carried out with an acylation catalyst such as 4-DMAP or pyridine.

One skilled in the art would readily know how to successfully carry out these as well as other methods of esterification of alcohols.

Additionally, sensitive or reactive groups on the compound of Formula (I) may need to be protected and deprotected during any of the above methods for forming esters. Protecting groups in general may be added and removed by conventional methods well known in the art (see, e.g., T. W. Greene and P. G. M. Wuts, *Protective Groups in Organic Synthesis*; Wiley: New York, (1999)).

The compounds of Formula (I) may contain one or more asymmetric centers, depending upon the location and nature of the various substituents desired. Asymmetric carbon atoms may be present in the (R) or (S) configuration. Preferred isomers are those with the absolute configuration which produces the compound of Formula (I) with the more desirable biological activity. In certain instances, asymmetry may also be present due to restricted rotation about a given bond, for example, the central bond adjoining two aromatic rings of the specified compounds.

Substituents on a ring may also be present in either cis or trans form, and a substituent on a double bond may be present in either Z or E form.

It is intended that all isomers (including enantiomers and diastereomers), either by nature of asymmetric centers or by restricted rotation as described above, as separated, pure or partially purified isomers or racemic mixtures thereof, be included within the scope of the instant invention. The purification of said isomers and the separation of said isomeric mixtures may be accomplished by standard techniques known in the art.

The particular process to be utilized in the preparation of the compounds of this invention depends upon the specific compound desired. Such factors as the selection of the specific X moiety, and the specific substituents possible at various locations on the molecule, all play a role in the path to be followed in the preparation of the specific compounds of this invention. Those factors are readily recognized by one of ordinary skill in the art.

Compounds of the present invention may be made according to the following General Reaction Schemes 1-6. In these schemes, unless otherwise noted, R" is $C_1$-$C_6$ lower alkyl or benzyl; Z is halo, OTs, or OMs; and $R^1$-$R^7$ and X are as described above for Formula (I) compounds.

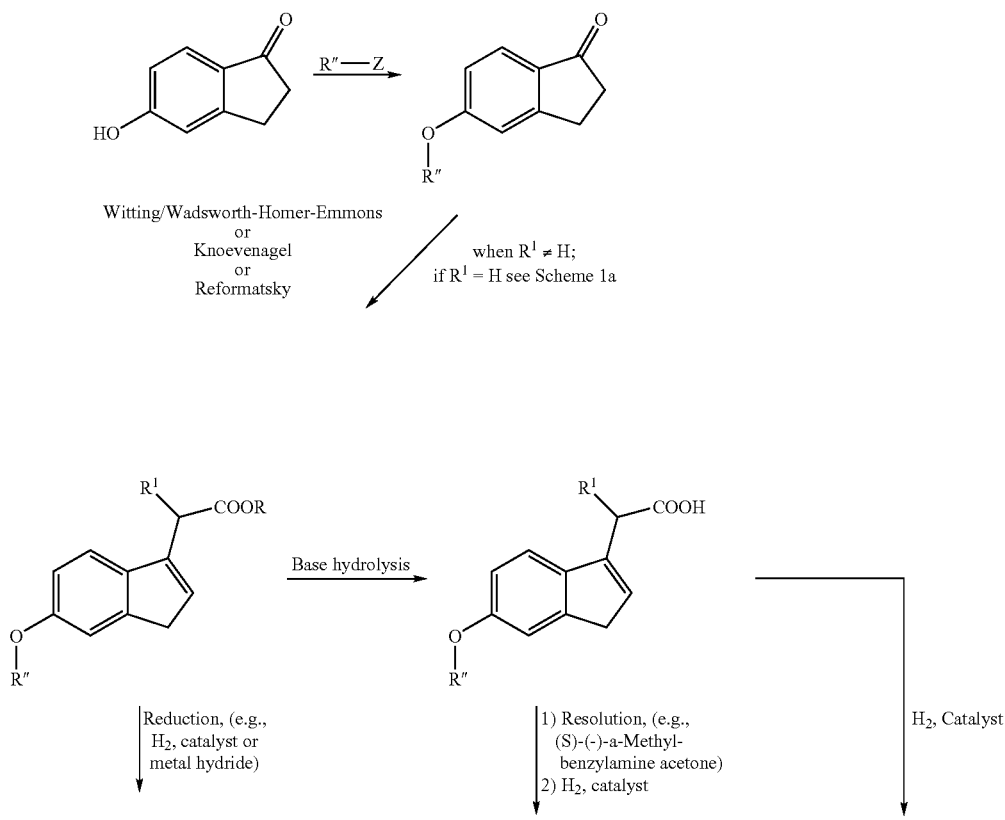

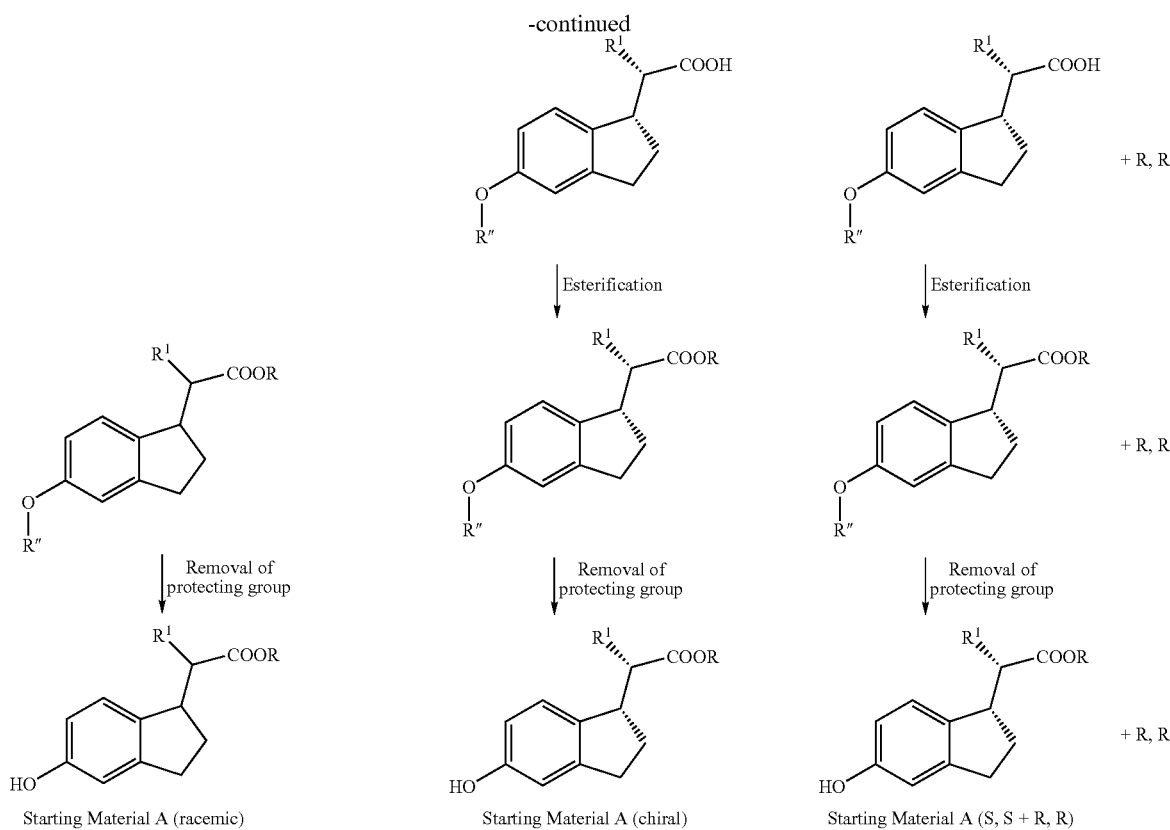
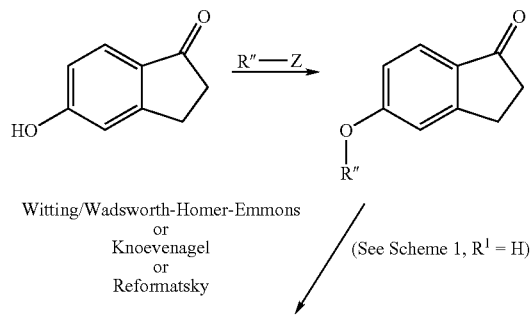
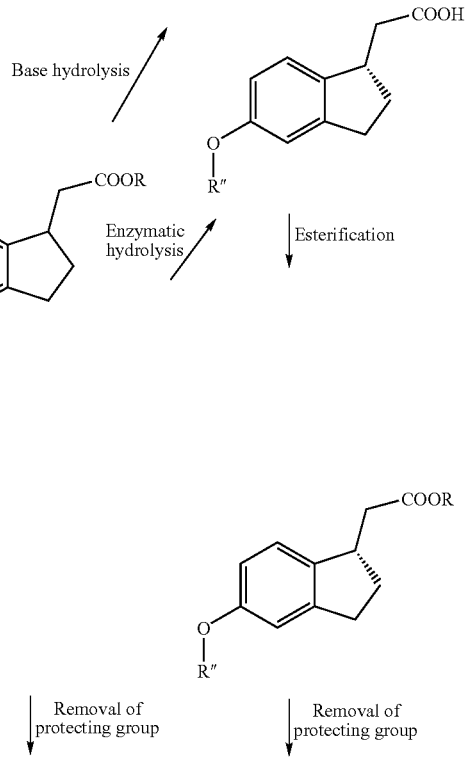

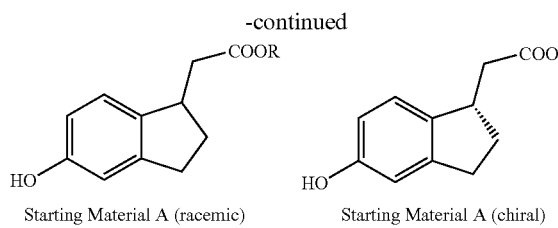

Starting Material A (racemic)　　Starting Material A (chiral)

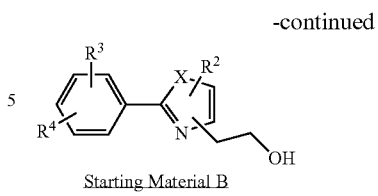

Starting Material B

Reaction Scheme 2
General Preparation of Oxazoles and Thiazole Starting Material B

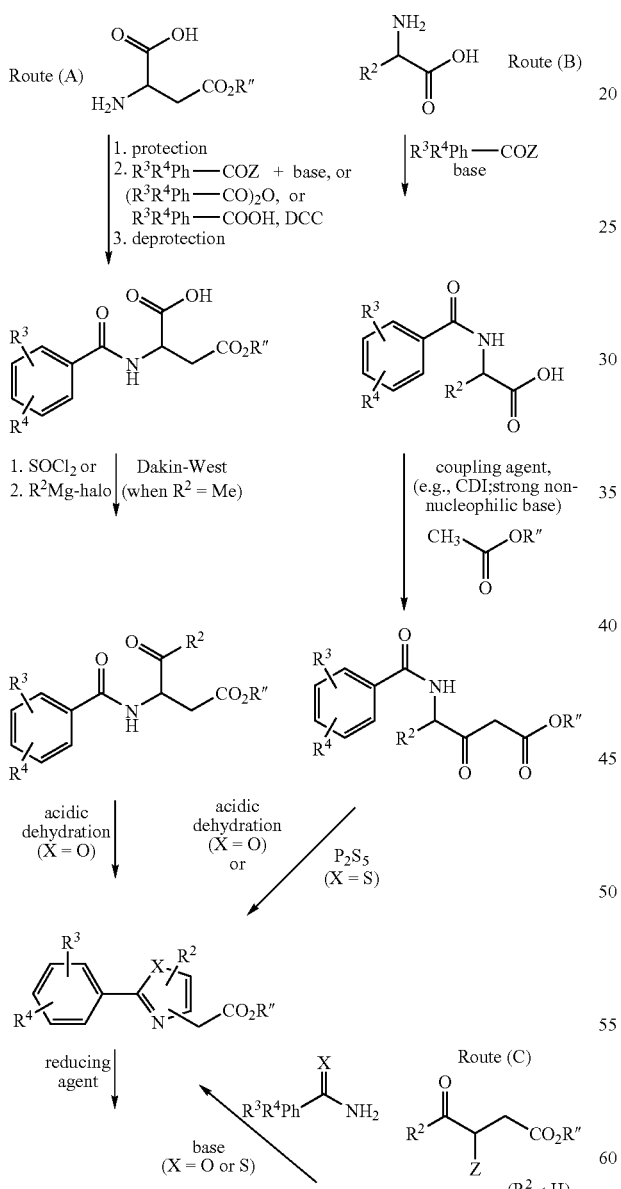

Reaction Scheme 3
General Preparation of Compounds of the Invention from Starting Materials A and B

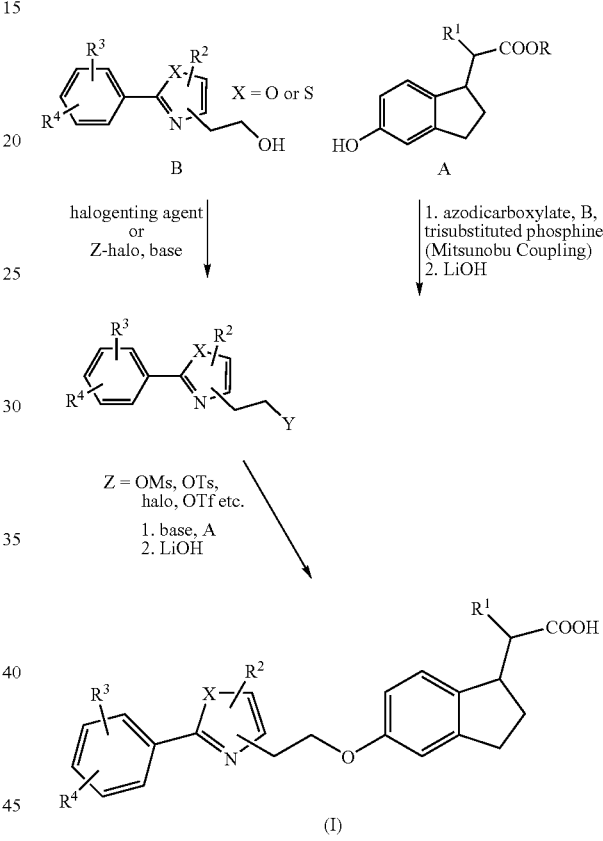

Specific compounds of Formula (I) containing amino, amido, and sulfonamido $R^4$ substituents and the like, can be prepared as shown in Reaction Schemes 4 and 5.

Reaction Scheme 4

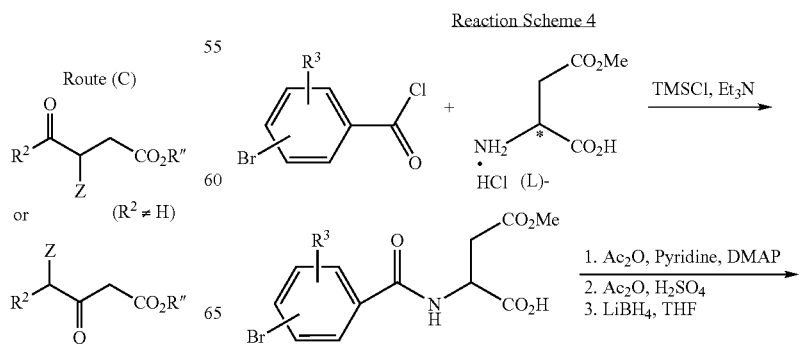

-continued

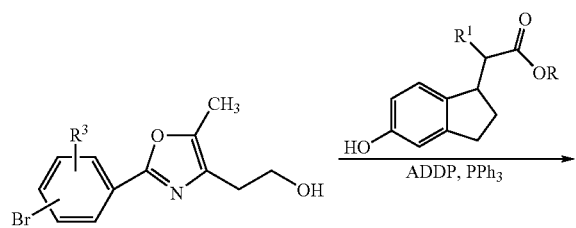
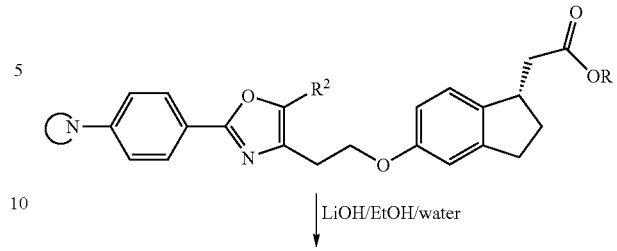

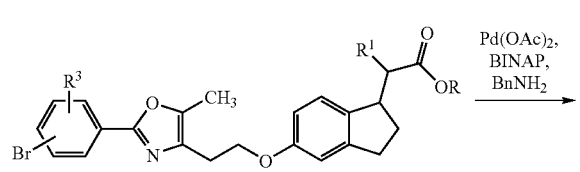
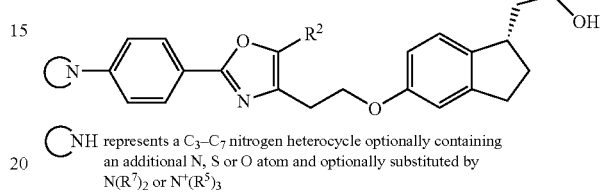

NH represents a $C_3$–$C_7$ nitrogen heterocycle optionally containing an additional N, S or O atom and optionally substituted by $N(R^7)_2$ or $N^+(R^5)_3$ Other compounds of Formula (I) in which $R^4$ is an alkenyl group can be prepared by the method outlined in Reaction Scheme 6.

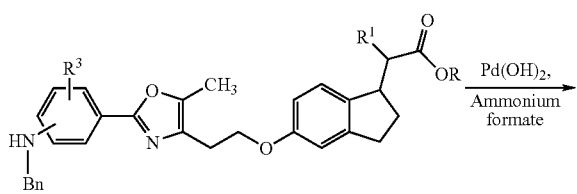

Reaction Scheme 6

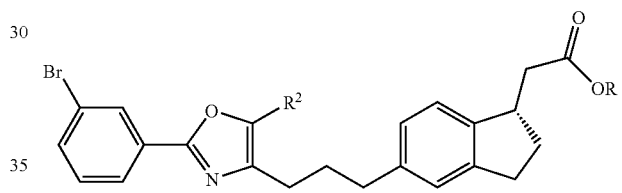

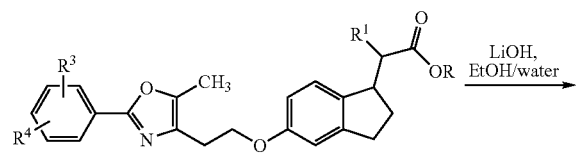
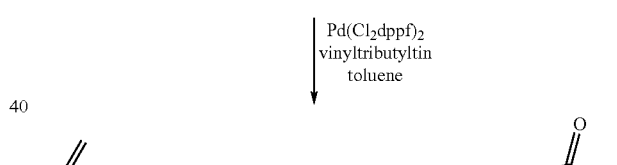

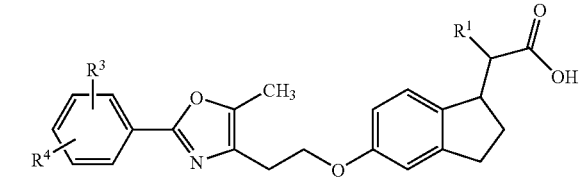
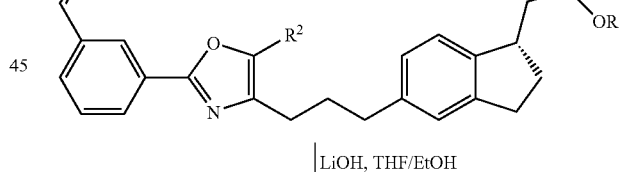

where $R^4$ = $NHR^6$, $NR^6R^6$, $NHCOR^7$, $NHSO_2R^7$, $NR^6COR^7$, or $NR^6SO_2R^7$

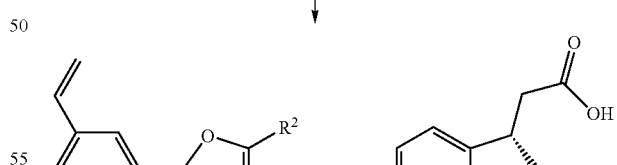

Reaction Scheme 5

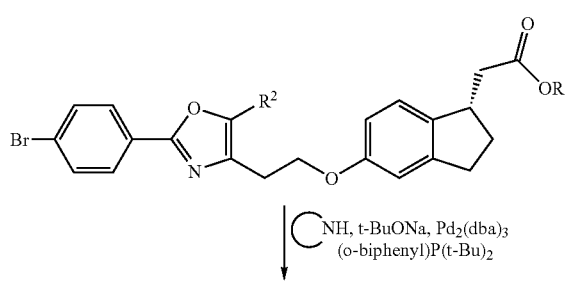

Experimental Procedures

In general, the compounds used in this invention may be prepared by standard techniques known in the art, by known processes analogous thereto, and/or by the processes described herein, using starting materials which are either commercially available or producible according to routine, conventional chemical methods. The following preparative methods are presented to aid the reader in the synthesis of the compounds of the present invention.

Air and moisture sensitive liquids and solutions were transferred via syringe or cannula, and introduced into reaction vessels through rubber septa. Commercial grade reagents and solvents were used without further purification. The term "concentration under reduced pressure" refers to use of a Buchi rotary evaporator at approximately 15 mm of Hg. All temperatures are reported uncorrected in degrees Celsius (° C). Thin layer chromatography (TLC) was performed on EM Science pre-coated glass-backed silica gel 60 A F-254 250 μm plates. Column chromatography (flash chromatography) was performed on a Biotage system using 32-63 micron, 60 A, silica gel pre-packed cartridges. Purification using preparative reversed-phase HPLC chromatography were accomplished using a Gilson 215 system, using a YMC Pro-C18 AS-342 (150×20 mm I.D.) column. Typically, the mobile phase used was a mixture of $H_2O$ (A) and MeCN (B). The water may be mixed with 0.1% TFA. A typical gradient was:

| Time [min] | A: % | B: % | Flow [mL/min] |
|---|---|---|---|
| 0.50 | 90.0 | 10.0 | 1.0 |
| 11.00 | 0.0 | 100.0 | 1.0 |
| 14.00 | 0.0 | 100.0 | 1.0 |
| 15.02 | 100.0 | 0.0 | 1.0 |

Chiral analytical HPLC experiments were performed using one the two following methods using a Varian Pro Star 1200:
  A: Column: Chiracel AD, 4.6 (I.D.)×250 mm
  Mobile Phase: A: 0.1% TFA in hexanes; B: 0.1% TFA in i-PrOH;
  Isocratic: 95%A (5%B), 20 min.
  Flow Rate: 1.5 mL/min
  Detector (UV): 284 nm
  B: Column: Chiracel AD, 4.6 (I.D.)×250 mm
  Mobile Phase: A: 0.1% TFA in hexanes; B: 0.1% TFA in i-PrOH
  Isocratic: 95% A (5% B), 25 min.
  Flow Rate: 1.0 mL/min
  Detector (UV): 284 nm Electron impact mass spectra (EI-MS or GC-MS) were obtained with a Hewlett Packard 5989A mass spectrometer equipped with a Hewlett Packard 5890 Gas Chromatograph with a J & W DB-5 column (0.25 uM coating; 30 m×0.25 mm). The ion source was maintained at 250° C. and spectra were scanned from 50-800 amu at 2 sec per scan. High pressure liquid chromatography-electrospray mass spectra (LC-MS) were obtained using a Hewlett-Packard 1100 HPLC equipped with a quaternary pump, a variable wavelength detector set at 254 nm, a YMC pro C-18 column (2×23 mm, 120A), and a Finnigan LCQ ion trap mass spectrometer with electrospray ionization. Spectra were scanned from 120-1200 amu using a variable ion time according to the number of ions in the source. The eluents were A: 2% acetonitrile in water with 0.02% TFA and B: 2% water in acetonitrile with 0.018% TFA. Gradient elution from 10% B to 95% over 3.5 minutes at a flowrate of 1.0 mL/min was used with an initial hold of 0.5 minutes and a final hold at 95% B of 0.5 minutes. Total run time was 6.5 minutes. For consistency in characterization data, the retention time (RT) is reported in minutes at the apex of the peak as detected by the UV-Vis detector set at 254 nm.

Routine one-dimensional NMR spectroscopy was performed on 300 or 400 MHz Varian Mercury-plus spectrometers. The samples were dissolved in deuterated solvents obtained from Cambridge Isotope Labs, and transferred to 5 mm ID Wilmad NMR tubes. The spectra were acquired at 293 K. The chemical shifts were recorded on the ppm scale and were referenced to the appropriate residual solvent signals, such as 2.49 ppm for DMSO-d6, 1.93 ppm for $CD_3CN$, 3.30 ppm for $CD_3OD$, 5.32 ppm for $CD_2Cl_2$, and 7.26 ppm for $CDCl_3$ for $^1H$ spectra, and 39.5 ppm for DMSO-d6, 1.3 ppm for $CD_3CN$, 49.0 ppm for $CD_3OD$, 53.8 ppm for $CD_2Cl_2$, and 77.0 ppm for $CDCl_3$ for $^{13}C$ spectra. General methods of preparation are illustrated in the reaction schemes, and by the specific preparative examples that follow.

Abbreviations and Acronyms

When the following abbreviations are used throughout the disclosure, they have the following meaning:
Ac acetyl
AcOH acetic acid
ADDP 1,1'-[azodicarbonyl]dipiperidine
BINAP 2,2'-Bis(diphenylphosphino)-1,1'-binaphthyl
Boc t-butoxycarbonyl
Bu butyl
$CDCl_3$ deuterochloroform
Celite® registered trademark of Celite Corp. brand of diatomaceous earth
CI chemical ionization
d doublet
dd doublet of doublet
ddd doublet of doublet of doublet
de diastereomeric excess
DAST (diethylamino) sulfur trifluoride
DEAD diethyl azodicarboxylate
DIA diisopropylamine
DIAD diisopropyl azodicarboxylate
DMAP 4-(N,N-dimethyl)amino pyridine
DME dimethoxyethane
DMF N,N-dimethyl formamide
DMSO dimethylsulfoxide
DMSO-$d_6$ dimethylsulfoxide-$d_6$
DOWEX® 66 Dowex hydroxide, weakly basic anion, macroporous, 25-50 mesh
dppf 1,1'-bis(diphenylphospino)ferrocene
Drierite® anhydrous calcium sulfate (W. A. Hammond Drierite Co.)
ee enantiomeric excess
EI electron impact ionization
EI-MS electron impact-mass spectrometry
Et ethyl
EtOH ethanol
EtOAc ethyl acetate
EtSH ethane thiol
g gram
GC-MS gas chromatography-mass spectrometry
h hour(s)
$^1H$ NMR proton nuclear magnetic resonance
Hex hexanes
HPLC high performance liquid chromatography
LC-MS liquid chromatography/mass spectroscopy
LDA lithium diisopropylamide
m mutiplet
M molar
m/z mass over charge Me methyl
MeCN acetonitrile
mg milligram
MHz megahertz
min minute(s)
mol mole
mmol millimole
MS mass spectrometry
N normal
NMR nuclear magnetic resonance
NaOAc sodium acetate
Pd/C palladium on carbon
$PdCl_2(dppf).CH_2Cl_2$ [1,1'-bis(diphenylphospino)ferrocene] dichloropalladium (II) complex with dicholoromethane (1:1)
Ph phenyl
$PPh_3$ triphenylphosphine
ppm parts per million
psi pounds per square inch
Pr propyl
q quartet
qt quintet
quant. quantitative
$R_f$ TLC retention factor
rt room temperature
RT retention time (HPLC)
s singlet
TBS tert-butydimethylsilyl
TBSCl tert-butydimethylsilyl chloride
TFA trifluoroacetic acid
THF tetrahydrofuran
TLC thin layer chromatography
TMAD $N^1,N^1, N^2, N^2$-tetramethyl-1,2-diazenedicarboxamide
TMS tetramethylsilane
v/v volume per unit volume
vol volume
w/w weight per unit weight

EXAMPLE 1

Preparation of ethyl (5-methoxy-2,3-dihydro-1H-inden-1-ylidene)ethanoate

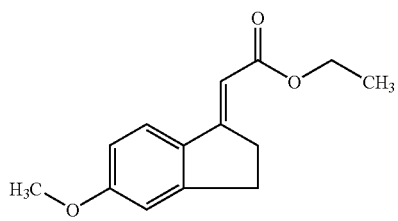

To a solution of 5-methoxyindanone (150 g, 0.91 mol) in anhydrous tetrahydrofuran (4.5 L), was added zinc (30 mesh, 103.64 g, 1.59 mol) and copper(I) chloride (4.53 g, 0.045 mol). The suspension was stirred under argon atmosphere and refluxed for 15 minutes; approximately a 25% portion of ethyl bromoacetate (133 mL, 1.18 mol) was added to the refluxing mixture in a slow dropwise fashion. After allowing to cool and stirring overnight at rt, TLC showed the presence of desired product, indicating the formation of reactive zinc species. The remainder of ethyl bromoacetate was added dropwise; an exotherm was observed (internal temperature increased to 35° C.). After 4 h, TLC showed complete reaction. After the solids settled to the bottom of the flask, the liquid was siphoned off leaving a small amount behind to cover the solids. The flask was re-charged with 5-methoxy-indanone (157.6 g, 1.86 mol), anhydrous tetrahydrofuran (4.5 L), and zinc (80.92 g, 2.73 mol). Ethyl bromoacetate (140 mL, 2.36 mol) was added dropwise. An exotherm was observed (internal temperature increased to 35° C.). When the stirred mixture cooled to rt, TLC showed the reaction to be complete. The solids were allowed to settle and the liquid was siphoned off. The combined reaction solutions were concentrated in vacuo to a volume of ~2 L. The liquid was then poured into sufficient 1N aqueous hydrochloric acid (cooled in ice water) to bring the pH to 1. The product was extracted with ethyl acetate (2×1 L, 1×500 mL). The combined extracts were washed with water, brine (1 L each), dried over sodium sulfate, filtered, and concentrated in vacuo to afford a dark red oil which solidified gradually (438.3 g; theoretical yield=432 g) $^1$H NMR ($CDCl_3$): δ 7.5 (d, 1H), 6.8 (m, 2H), 6.2 (t, 1H), 4.2 (q, 2H), 3.8 (s, 3H), 3.3 (m, 2H), 3.0 (t, 2H), 1.3 (t, 3H). MS (CI) m/z 233 $[M+H]^+$.

EXAMPLE 2

Preparation of ethyl (5-methoxy-2,3-dihydro-1H-inden-1-yl)acetate

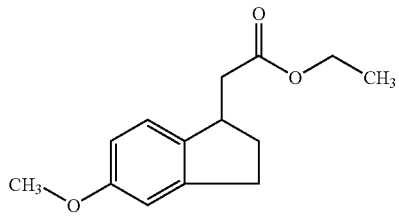

The crude product of Example 1 was dissolved in absolute ethanol (2.6 L) and hydrogenated at 40 psi of hydrogen over 10% palladium on carbon (21.6 g). Filtration through Celite and concentration of the filtrate afforded 433.3 g of brown oil (99% yield for 2 steps). $^1$H NMR ($CDCl_3$): δ 7.1 (dd, 1H), 6.8 (d, 1H), 6.7 (dd, 1H), 4.2 (q, 2H), 3.8 (s, 3H), 3.5 (m, 1H), 2.9 (m, 2H), 2.7 (dd, 1H), 2.4 (m, 2H), 1.7 (m, 1H), 1.3 (t, 3H). MS (CI) m/z 235 $[M+H]^+$.

EXAMPLE 3

Preparation of (5-methoxy-2,3-dihydro-1H-inden-1-yl)acetic acid

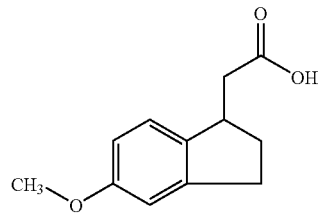

To a solution of the crude ester (416 g, 1.77 mol) prepared in Example 2 in 1 L EtOH, was added a solution of NaOH (142 g, 3.54 mol) in 1.5 L water. The cloudy reaction mixture was heated to reflux, during which time the color changed to dark red, and the reaction became homogeneous. After 1 h, the reaction was cooled to rt and the EtOH was removed under reduced pressure. The basic aqueous layer was washed with Et$_2$O (3×500 mL), then acidified with conc. HCl to pH ~4 upon which an oil residue formed. The mixture was extracted with Et$_2$O (4×500 mL). The combined extracts were washed with water (2×300 mL), brine, then dried over Na$_2$SO$_4$. Filtration and evaporation of solvent under reduced pressure gave the title compound (305 g, 83%) as a yellow solid after overnight drying under vacuum. $^1$H NMR (CDCl$_3$) δ 7.34(d, 1H), 6.71(s, 1H), 6.65(dd, 1H), 3.71(s, 3H), 3.47(m, 1H), 2.80(m, 3H), 2.35(m, 2H), 1.71(m, 1H). MS (CI) m/z 207 [M+H]$^+$.

EXAMPLE 4

Preparation of [(1S)-5-methoxy-2,3-dihydro-1H-inden-1-yl]acetic acid

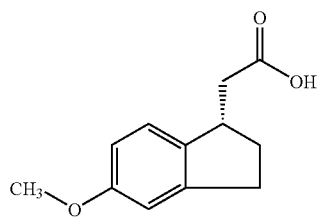

To a solution of the acid (341.0 g, 1.65 mol) prepared in Example 3 in 8.2 L reagent grade acetone, was added (S)-(–)-α-methylbenzylamine (223.8 mL, 1.74 mol) dropwise at rt with stirring. A thick white precipitate formed during the addition. An additional 500 mL acetone was added and stirring continued for 1 h. The solids were collected by filtration, washed with 300 mL acetone, and dried under suction. The solids were then suspended in acetone (8.2 L) and warmed to reflux until all solids dissolved. The solution was cooled slowly overnight, during which time a white precipitate formed. The suspension was cooled to 0° C., then filtered, and the solids were washed with 500 mL acetone. After drying under suction, a sample analyzed by analytical HPLC showed 95% ee. The recrystallization process was repeated as above using 6.7 L acetone. HPLC analysis showed 99% ee. After drying under suction, 192 g of salt were obtained. The salt was suspended in 2 L EtOAc and 1 L of 1N HCl solution and shaken in a separatory funnel, whereupon the salt dissolved. The organic layer was separated, washed with 1N HCl (500 mL), water (2×300 mL), and brine, then dried over Na$_2$SO$_4$. The solvent was evaporated under reduced pressure, giving an oil which soon solidified. The title product (120.5 g, 35%) was obtained as an off-white solid after vacuum drying. $^1$H NMR (CDCl$_3$) δ 7.10 (d, 1H), 6.79 (d, 1H), 6.73 (dd, 1H), 3.79 (s, 3H), 3.55 (m, 1H), 2.89 (m, 2H), 2.79 (dd, 1H), 2.46 (dd, 1H), 2.43 (m, 1H), 1.80 (m, 1H). MS (ESI) m/z 207 [M+H]$^+$.

EXAMPLE 5

Preparation of [(1S)-5-methoxy-2,3-dihydro-1H-inden-1-yl]acetic acid

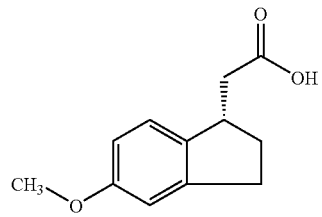

As an alternative to Example 4, the title compound may also be prepared via an enzymatic process. Thus, a cloudy mixture of the crude ester (500.0 g, 2.13 mol; 87% pure as determined by HPLC) prepared in Example 2, in 1 L reagent grade acetone, 2.5 L phosphate buffer (pH 7.0, 0.05 M) and 2.5 L deionized water was treated in one portion with Amano Lipase PS (150 g), and the mixture stirred efficiently at rt overnight. HPLC analysis of an aliquot (homogeneous aliquot prepared by dissolving aliquot in IPA followed by filtration) showed one peak corresponding to unreacted R-ester and another peak corresponding to desired S-acid. Trace amounts of S-ester and R-acid were noted. 2N HCl (500 mL, ensure a pH ~2) was added in one portion to the reaction and stirred for 20 minutes. The mixture was filtered and the solids were washed with EtOAc (2×500 mL), then water (500 mL). The combined filtrates were further diluted with 1 L EtOAc, and the layers stirred together vigorously. Stirring was stopped and the layers allowed to separate. Emulsions were noted, but could be broken with the addition of solid NaCl and stirring. The aqueous layer was removed, then extracted with EtOAc (3×1 L) in the same fashion. The combined organic extractions were washed with water 4×500 mL), then with brine. The resulting organic layer was extracted with a 5% Na$_2$CO$_3$ solution (8×500 mL). HPLC analysis of the organic layer showed that it contained none of the S-enantiomer acid. The combined Na$_2$CO$_3$ extracts were washed with EtOAc (2×1 L), then acidified to pH ~2 by the addition of 2N HCl. A white solid precipitated, accompanied by CO$_2$ evolution. The mixture was extracted with EtOAc (3×1 L). The combined extracts were washed with water (2×1 L) and brine, then dried over Na$_2$SO$_4$. HPLC analysis of this solution showed the material was 98% ee. The solvent was evaporated under reduced pressure, giving an oil which soon solidified. The title product (172.9 g) was obtained as an off-white solid after vacuum drying. This material was recrystallized from boiling hexanes (8.8 L). After overnight cooling, light yellow needles were collected via filtration, washed with hexanes (200 mL), and dried under suction. The title product (146.9 g, 38% from crude starting ester) was obtained as light yellow needles after vacuum drying. $^1$H NMR results as above.

EXAMPLE 6

Preparation of ethyl [(1S)-5-methoxy-2,3-dihydro-1H-inden-1-yl]acetate

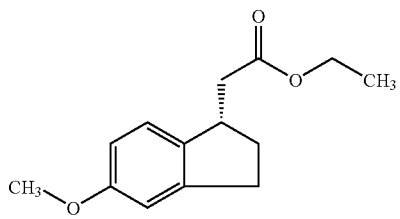

To a solution of the acid (305 g, 1.48 mol) prepared in either Example 4 or 5 in 4.8 L absolute EtOH at rt under argon, was added chlorotrimethylsilane (413 mL, 3.25 mol) dropwise. An approximate 5° C. rise in temperature was noted during the addition. The reaction was stirred overnight. EtOH was evaporated under reduced pressure, giving a bi-phasic liquid mixture. This was diluted in 500 mL ice-water, then extracted with EtOAc (2×750 mL). The combined extracts were washed with water (3×300 mL), then with saturated NaHCO$_3$ (200 mL). The organic was washed once more with water (300 mL), then brine, and dried over Na$_2$SO$_4$. The title compound (354 g, 102%) was obtained as a light yellow oil after solvent removal and vacuum drying. $^1$H NMR (CDCl$_3$) δ 7.07 (d, 1H), 6.78 (d, 1H), 6.71 (dd, 1H), 4.18 (q, 2H), 3.78 (s, 3H), 3.52 (m, 1H), 2.89 (m, 2H), 2.72 (dd, 1H), 2.37 (o, 2H), 1.74 (m, 1H), 1.28 (t, 3H). MS (CI) m/z 235 [M+H]$^+$.

EXAMPLE 7

Preparation of ethyl [(1S)-5-hydroxy-2,3-dihydro-1H-inden-1-yl]acetate

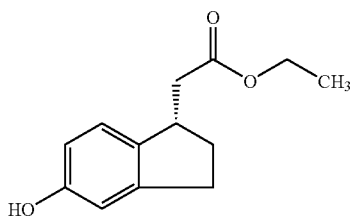

To a cold solution (ice water bath) of the compound (346 g, 1.48 mol) prepared in Example 6 in 4.2 L CH$_2$Cl$_2$, was added AlCl$_3$ (984.6 g, 7.38 mol) portionwise under argon such that the reaction temperature was maintained below 10° C. The light brown suspension was stirred 10 minutes, then EtSH (546 mL, 7.38 mol) was added dropwise at such a rate that the reaction temperature was maintained below 5° C. After 2.5 h of stirring below 10° C., the reaction mixture was slowly poured into 6 L of ice water with strong agitation. The organic layer was separated, and the aqueous layer was extracted with CH$_2$Cl$_2$ (3×1 L). The combined CH$_2$Cl$_2$ layers were washed with water (2×1 L), then dried over Na$_2$SO$_4$. The solvent was removed under reduced pressure, giving a brown oil, which was filtered through a pad of silica gel (eluted with 0-10% EtOAc/Hexanes). Fractions were collected and the title compound (314 g, 96%) was obtained as a thick yellow oil after solvent removal and vacuum drying. $^1$H NMR (CDCl$_3$) δ 6.92 (d, 1H), 6.62 (d, 1H), 6.55 (dd, 1H), 4.10 (q, 2H), 3.43 (q, 1H), 2.75 (m, 2H), 2.64 (dd, 1H), 2.31 (dd, 1H), 2.29 (m, 1H), 1.67 (m, 1H), 1.20 (t, 3H). MS (CI) m/z 221 [M+H]$^+$.

EXAMPLE 8

Preparation of methyl 2-(6-methoxy-1H-inden-3-yl)propanoate

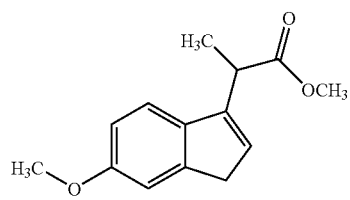

In an oven dried 3-neck 5.0 L flask fitted with a condenser, a thermometer, and an addition funnel was charged under argon, 5-methoxy-1-indanone (86.73 g, 0.52 mol) and THF (2.13 L). The mixture was stirred at rt and became an orange-colored solution. To this were added zinc granules (59.96 g, 0.92 mol, 30 mesh). The mixture was heated to ~50° C. with simultaneous addition of a solution of methyl-2-bromopropionate (88.80 g, 0.79 mol) in THF (393 mL). The reaction mixture was heated for a period of 20 h, after which heating was stopped and the reaction mixture cooled to rt followed by cooling on an ice bath. The mixture was then slowly quenched with HCl (3.3 L, 1 N aqueous solution) maintaining the internal temperature at ~18° C. The aqueous layer was extracted with EtOAc (3×500 mL). The organic layer was then washed with water (4×500 mL, a pH of ~4.5 achieved), brine (500 mL), and dried over Na$_2$SO$_4$. The solvent was removed under vacuum to give a dark brown colored oil. The crude product was purified by silica gel chromatography (1-8% EtOAc/hexane gradient) to give 54.09 g (52%) of the title compound as a dark brown oil. $^1$H NMR (400 MHz, DMSO-d6): δ 7.25 (1H, d), 7.09 (1H, s), 6.87 (1H, dd), 6.24 (1H, s), 3.82 (1H, q), 3.75 (3H, s), 3.58 (3H, s), 3.30 (2H, s), 1.21 (3H, d); LC-MS: RT=3.00 min, M+H$^+$: 233.0.

EXAMPLE 9

Preparation of 2-(6-methoxy-1H-inden-3-yl)propanoic acid

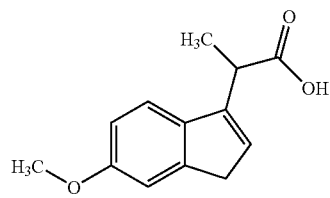

In a 1 L three-neck flask charged with NaOH (18.57 g, 0.464 mol) and water (216 mL), was slowly added (over 15-20 minutes) a solution of methyl 2-(6-methoxy-1H-inden-3-yl)propanoate (Example 8) (53.92 g, 0.232 mol) in MeOH (215 mL). During the addition, the reaction temperature increased to 38° C. To this mixture was added THF (108 mL), and then the mixture was heated to 40-45° C. for a period of 8 h and subsequently stirred at rt for 17 h. The solvent was removed under vacuum and the resulting aqueous mixture was extracted with CH₂Cl₂ (3×100 mL). The aqueous layer was acidified with HCl (38 mL, 37% aqueous solution) to pH ~2.5 and extracted with EtOAc (3×100 mL). The combined organic layers were washed with water (4×150 mL) and brine (50 mL), dried over Na₂SO₄, and filtered. The solvent was evaporated under vacuum and the resulting oil was dried under vacuum at 40-45° C for 16-18 h to give 45.71 g (90%) of the title compound. ¹H NMR (400 MHz, DMSO-d6): δ 7.25 (1H, d), 7.05 (1H, s), 6.83 (1H, dd), 6.19 (1H, s), 3.73 (3H, s), 3.68 (1H, q), 3.30 (2H, s), 1.39 (3H, d); LC-MS: RT=2.43 min, (M+H)⁺: 219.1.

EXAMPLE 10

Preparation of (2S)-2-[(1S)-5-methoxy-2,3-dihydro-1H-inden-1-yl]propanoic acid

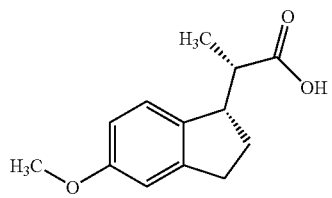

In a 1 L single neck flask was charged the racemic 2-(6-methoxy-1H-inden-3-yl)propanoic acid (Example 9) (41.88 g, 0.192 mol) and acetonitrile (629 mL). To this dark orange colored solution was added under stirring (R)-(+)-α-methyl-benzylamine (25.91 mL, 0.201 mol) slowly over a period of 10 minutes. The dark orange colored solution was then stirred at rt for 16-18 h. The resulting suspension was concentrated to dryness under vacuum to give 61.32 g of the 1:1 diastereomeric salt mixture. Under argon, ethanol (19 mL) was added to chlorotris(triphenylphosphine)rhodium(I) (2.0 g, 2.2 mmol). To this suspension was added a solution of the above 1:1 diastereomeric salt mixture (15.0 g, 0.044 mol) in a mixture of EtOH (116 mL) and THF (15 mL). This mixture was hydrogenated in a Parr apparatus under 60 psi at rt over a period of 17 h. The resulting suspension was cooled to 0-5° C. over a period of 30 minutes. The precipitate was filtered off and dried under vacuum at 40-45° C. for a period of 16-18 h to give the diastereomerically enriched salt (6.79 g, 45%) containing mainly the (S,S)-enantiomer of its anionic component [84% ee, chiral analytical HPLC, Method B]. The assignment of the absolute configuration is described in the following part. This crude salt was recrystallized by dissolution in MeCN (238 mL) under reflux condition. The resulting solution was cooled over 2 h and the precipitate filtered off, washed with MeCN (13 mL) and dried under vacuum at 40-45° C. to give the desired salt (5.19 g, 76% of mass recovered) having a ee of 98.14% (chiral analytical HPLC, Method B] reflecting the identical enantiomeric purity of the (S,S)-enantiomer of its anionic component. ¹H NMR (of the salt) (400 MHz, DMSO-d6): δ 7.35 (2H, d), 7.30 (2H, t), 7.19 (1H, m), 7.05 (1H, d), 6.73 (1H, s), 6.65 (1H, dd), 4.07 (1H, q), 3.70 (3H, s), 3.40 (1H, q), 2.77 (2H, m), 2.58 (1H, q), 2.05 (1H, m), 1.75 (1H, m), 1.35 (3H, d), 0.87 (3H, d); Quattro Micro (Micromass)(−esi) (M−H)⁻: 219 (free acid). The absolute stereochemistry of the title compound was determined to be (1S,2S) by single crystal x-ray crystallography of the (R)-(+)-α-methyl benzylamine salt. A dichloromethane solution of the diastereomerically pure salt was acidified by washing with 1N HCl followed by washing the organic layer with water. The organic layer was dried with Na₂SO₄ and concentrated to dryness to give the enantiomerically pure free acid, (2S)-2-[(1S)-5-methoxy-2,3-dihydro-1H-inden-1-yl]propanoic acid.

EXAMPLE 11

Preparation of methyl (2S)-2-[(1S)-5-methoxy-2,3-dihydro-1H-inden-1yl]propanoate

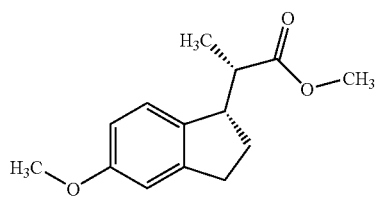

A suspension of (2S)-2-[(1S)-5-methoxy-2,3-dihydro-1H-inden-1-yl]propanoic acid (Example 10) (6.45 g, 0.029 mol), sodium bicarbonate (7.380 g, 0.088 mol), and iodomethane (5.5 mL, 0.088 mol) in DMF (60 mL) was stirred at rt for a period of 17 h. The completion of the reaction was achieved by addition of an additional amount of iodomethane (0.93 mL, 0.015 mol) and stirring for another 3 h at rt. The reaction mixture was poured into water (200 mL) and the aqueous layer was extracted with EtOAc (2×100 mL). The combined organic layers were washed with NaOH (1 N aqueous solution), water and brine, dried (Na₂SO₄), filtered, and concentrated to dryness under vacuum to give 5.70 g (84%) of the title compound. ¹H NMR (400 MHz, DMSO-d6) δ 6.96 (d, 1H), 6.77 (d, 1H), 6.67 (dd, 1H), 3.70 (s, 3H), 3.63 (s, 3H), 3.38 (q, 1H), 2.78 (m, 3H), 2.08 (m, 1H), 1.78 (m, 1H); LC-MS RT=3.10 min; (M+H)⁺ 234.9.

EXAMPLE 12

Preparation of methyl (2S)-2-[(1S)-5-hydroxy-2,3-dihydro-1H-inden-1-yl]propanoate

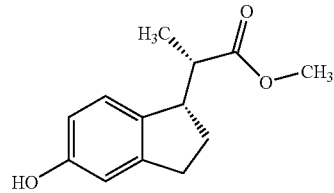

A solution of methyl (2S)-2-[(1S)-5methoxy-2,3-dihydro-1H-inden-1yl]propanoate (Example 11) (5.70 g, 0.024 mol) in CH₂Cl₂ (70 mL), under argon, was cooled to 0-5° C. and AlCl₃ (16.22 g, 0.122 mol) was added portion-wise while maintaining the temperature below 10° C. To this mixture was added EtSH (9.0 mL, 0.122 mol) and the resulting mixture was stirred at 0-5° C. for 4 h. The reaction mixture was then slowly poured into vigorously stirred ice-water (200 mL) and the aqueous layer was extracted with $CH_2Cl_2$. The combined organic layers were washed with water, brine, dried ($Na_2SO_4$), filtered, and concentrated to dryness under vacuum. The resulting crude product was purified by silica gel flash chromatography (gradient of 10-40% ethyl acetate/hexanes) to give 4:2 g (80%) of the title compound. $^1$H NMR (400 MHz, $CDCl_3$): δ 6.93 (d, 1H), 6.70 (s, 1H), 6.63 (dd, 1H), 3.72 (s, 3H), 3.50 (q, 1H), 2.83 (m, 3H), 2.19 (m, 1H), 1.90 (m, 1H), 1.08 (d, 3H); LC-MS: RT=8.60 min, $(M+H)^+$ 220.

EXAMPLE 13

Preparation of (2S)-2-[(1S)-5-methoxy-2,3-dihydro-1H-inden-1-yl]propanoic acid and (2R)-2-[(1R)-5-methoxy-2,3-dihydro-1H-inden-1-yl]propanoic acid

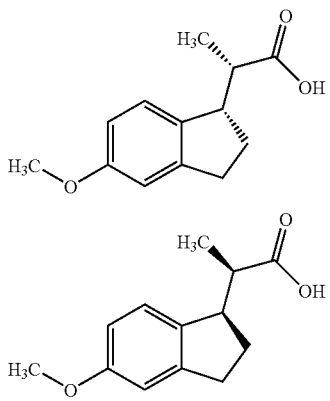

The starting acid (Example 9) was reacted under Wilkinson's hydrogenation conditions (60 psi) using 4.5 g starting material, 1.04 g catalyst, and 4.5 mL triethylamine in 45 mL ethanol and 5 mL THF (analogous procedure as for Example 10). The standard extractive workup gave 3.22 g product. $^1$H NMR (400 MHz, DMSO-d6) 0.87 (d, 3H), 1.75 (m, 1H), 2.04 (m, 1H), 3.66 (s, 3H), 6.65 (m, 1H), 6.76 (s, 1H), 7.04 (d, 1H) 12.18 (bs, 1H); LC-MS RT 2.41 min.

EXAMPLE 14

Preparation of methyl (2S)-2-[(1S)-5-methoxy-2,3-dihydro-1H-inden-1-yl]propanoate and methyl (2R)-2-[(1R)-5-methoxy-2,3-dihydro-1H-inden-1-yl]propanoate

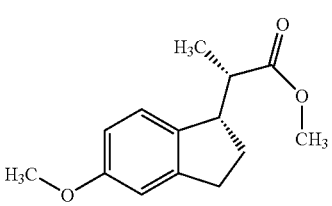

-continued

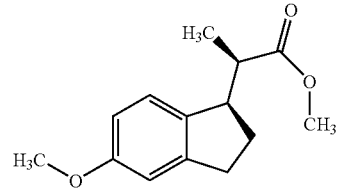

The compound was prepared by the reaction of 1.5 g starting acid (Example 13), 0.93 mL iodomethane, and 1.75 g sodium bicarbonate in 10 mL methanol under the esterification conditions as described in Example 11. Workup gave 1.53 g, 96%. $^1$H NMR (400 MHz), ($CD_2Cl_2$): δ 1.05 (d, 3H), 1.88 (m, 1H), 2.19 (m, 1H), 3.44 (m, 1H), 3.68 (s, 3H), 3.77 (s, 3H).

EXAMPLE 15

Preparation of methyl (2S)-2-[(1S)-5-hydroxy-2,3-dihydro-1H-inden-1-yl]propanoate and methyl (2R)-2-[(1R)-5-hydroxy-2,3-dihydro-1H-inden-1-yl]propanoate

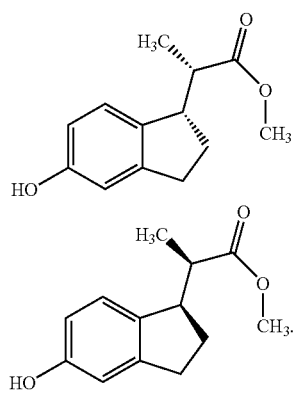

Using the demethylation conditions described in Example 14, and starting with Example 16 (1.53 g), $AlCl_3$ (4.35 g) and EtSH (2.4 mL) in $CH_2Cl_2$ (20 mL), 1.21 g of product (84%) were obtained. $^1$H NMR ($CD_2Cl_2$): δ 1.05 (d, 3H), 1.88 (m, 1H), 2.18 (m, 1H), 3.45 (m, 1H), 3.67 (s, 3H), 6.60 (m, 1H, aryl), 6.69 (s, 1H), 6.93 (d, 1H).

EXAMPLE 16

Preparation of methyl 2-(6-methoxy-1H-inden-3-yl)butanoate

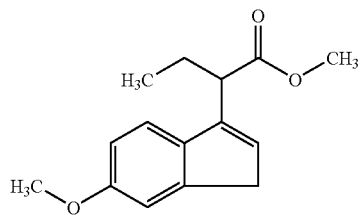

An oven dried 5-L four-necked round-bottomed flask was fitted with a thermometer, a condenser, an addition funnel, and a mechanical stirrer. Under an argon atmosphere, a suspension of 5-methoxy-1-indanone (80.0 g, 494 mmol), Zn powder (Lancaster, 56.2 g, 865 mmol) in THF (2 L, anhydrous) was stirred at 60° C. (internal temperature), while a solution of methyl bromobutyrate (134.1 g, 741 mmol) in THF (400 mL, anhydrous) was added slowly using an addition funnel. After completion of the addition, the reaction mixture was stirred at 60° C. (internal temperature) for 1 h. The reaction was followed by TLC analysis of aliquots following 1 N aqueous HCl workup. After the reaction was completed, it was cooled in an ice-water bath followed by slow addition HCl (3 L, 1 N aqueous solution). The internal temperature was kept below 20° C. The mixture was then extracted with EtOAc (1 L). The organic layer was washed with water until pH 6.0-7.0, then with brine, dried over $Na_2SO_4$, and then filtered. The product (127 g, >99%), a yellow oil, was obtained after solvent removal and drying under vacuum. $^1$H NMR (300 MHz), (DMSO-d6) δ 7.28 (d, 1H), 7.05 (d, 1H), 6.82 (dd, 1H), 6.22 (s, 1H), 3.72 (s, 3H), 3.60 (m, 1H), 3.58 (s, 3H), 3.28 (s, 2H), 1.95 (m, 1H), 1.80 (m, 1H), 0.88 (t, 3H).

EXAMPLE 17

Preparation of 2-(6-methoxy-1H-inden-3-yl) butanoic acid

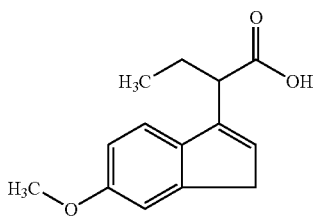

To a solution of the ester prepared in Example 16 (200.0 g, 813 mmol) in MeOH (2 L), was added a solution of KOH (91.0 g, 1.63 mol) in water (200 mL). The reaction mixture was stirred at 60° C. (internal temperature) for 2 h. TLC showed 70% conversion. A solution of KOH (45.0 g, 0.81 mol) in water (100 mL) was then slowly added to the reaction mixture. The reaction was complete in 1 h, after which the mixture was cooled to rt, and then the solvents were removed at under reduced pressure. The residue was dissolved in water (3 L), and then washed with EtOAc (2×1 L). The aqueous layer was cooled in an ice-water bath, acidified with HCl (37% aqueous solution) to pH<3.0 and extracted with $CH_2Cl_2$ (3 L). The organic phase was washed with water (2×1 L), dried over $Na_2SO_4$, filtered, and then the filtrate was stirred with 30.0 g charcoal for 2 h. The charcoal was removed by filtration through a pad of Celite® to provide the title compound (175 g, 93%) as a light brown solid after solvent removal and drying under reduced pressure. $^1$H NMR (300 MHz), (DMSO-d6) δ 12.20 (b, 1H), 7.30 (d, 1H), 7.06 (d, 1H), 6.82 (dd, 1H), 6.22 (s, 1H), 3.75 (s, 3H), 3.45 (t, 1H), 3.30 (s, 2H), 1.90 (m, 1H), 1.78 (m, 1H), 0.90 (t, 3H).

EXAMPLE 18

Preparation of (2S)-2-(6-methoxy-1H-inden-3-yl) butanoic acid

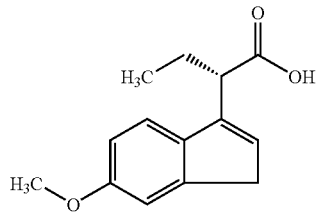

To a solution of the racemic indene acid prepared in Example 17 (300 g, 1.29 mol) in $CH_3CN$ (4.5 L), was added quinine (324 g, 1.0 mol) at rt. The mixture was stirred for 1 h, and became a homogeneous solution. A small amount of the insoluble particles were removed by filtration through a microfiber filter under vacuum. The filtrate was then mechanically stirred under argon for 24 h, a precipitate formed, after which a small sample of the solid was taken and analyzed by chiral analytical HPLC (Method A), showing 76% ee. The agitation was continued for two additional days, after which the suspension was filtered. The solid collected was washed with $CH_3CN$ (3×200 mL), and then dried under vacuum at 40° C. for 3 h. This solid was stirred with $CH_3CN$ (4.5 L) at 70° C. until all solids went into solution. Heat was shut off, and the solution was allowed to cool to rt slowly. The resulting suspension was stirred at rt for 24 h and then filtered. The filter cake was washed with $CH_3CN$ (3×250 mL) and dried under vacuum at 40° C. for 24 h. This quinine salt was collected as a white solid (254.6 g, 35.4% yield, 96.8% ee for the acid).

The quinine salt (544.3 g, 0.98 mol) was dissolved in $CH_2Cl_2$ (4.0 L) to obtain a clear solution. This solution was stirred vigorously with HCl (4.0 L of a 2N aqueous solution) in a 22-L round-bottomed flask with a bottom valve. After 30 minutes, the mixture was allowed to settle, the organic layer was separated, and the aqueous layer was extracted with $CH_2Cl_2$ (1 L). The combined organic layers were washed with water (3×2.0 L) until pH 5.0-6.0, and then dried over $Na_2SO_4$. The product (230.8 g, 99%, 96.8% ee) was obtained as an offwhite solid after solvent removal and vacuum drying. The $^1$H NMR spectrum was identical to that of the racemic material described in Example 17.

Treatment of the mother liquor in similar fashion gave the enriched R-isomer. Alternatively, the mother liquor could be subjected to aqueous basic conditions in order to effect racemization and recovery of racemic starting material.

The absolute configuration was determined after the following step (Example 19).

EXAMPLE 19

Preparation of (2S)-2-[(1S)-5-methoxy-2,3-dihydro-1H-inden-1-yl]butanoic acid

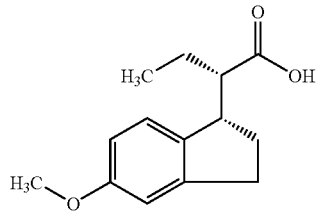

A solution of the product obtained in Example 18 (105 g, 453 mmol), ClRh(PPh₃)₃ (21.0 g, 22.7 mmol), and Et₃N (68.8 g, 679.5 mmol) in EtOH (945 mL) and THF (105 mL) was shaken in a 2-L pressure bottle under H₂ (60 psi) for 16 h. The solvents were removed under reduced pressure and the residue was taken up in a mixture of HCl (1.5 L, 1 N aqueous solution) and CH₂Cl₂ (1.5 L) and stirred. The aqueous layer was extracted with CH₂Cl₂ (2×250 mL). The combined organic layers were washed with HCl (1 L, 1 N aqueous solution) and stirred with NaOH (1 L, 1 N aqueous solution). The organic layer was extracted with NaOH (2×0.5 L, 1 N aqueous solution). The combined aqueous layer was washed with CH₂Cl₂ (2×250 mL), and acidified (pH 2.0-3.0) by a slow addition of HCl (37% aqueous solution) maintaining the temperature below 15° C. The acidic-mixture was extracted with CH₂Cl₂ (2×1.5 L). The combined organic phases were washed with water (2×0.5 L) until pH 5.0-6.0 and brine, dried over Na₂SO₄, filtered, and then concentrated under reduced pressure. The product (101.0 g, 95% yield, 96.8% ee) was obtained as a light yellow oil. The absolute configuration of the title compound was determined by single crystal x-ray crystallography of the corresponding (R)-(+)-methyl benzylamine salt. ¹H NMR (300 MHz), (DMSO-d6) δ 12.20 (s, 1H), 7.04 (d, 1H), 6.78 (d, 1H), 6.66 (dd, 1H), 3.70 (s, 3H), 3.28 (m, 1H), 2.72 (m, 2H), 2.32 (m, 1H), 2.06 (m, 1H), 1.80 (m, 1H), 1.50 (m, 1H), 1.36 (m, 1H), 0.82 (t, 3H).

EXAMPLE 20

Preparation of methyl (2S)-2-[(1S)-5-methoxy-2,3-dihydro-1H-inden-1-yl]butanoate

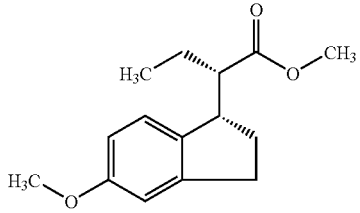

A suspension of the acid prepared in Example 19 (220.0 g, 0.94 mol), NaHCO₃ (237.0 g, 2.82 mol), CH₃I (200 g, 1.41 mol) in DMF (2.0 L) was stirred under argon at rt for 18 h. Adding additional CH₃I (100 g, 0.71 mol) and stirring for an additional 24 h at rt caused completion of the reaction. The reaction mixture was poured into 4.0 L water, and extracted with EtOAc (2×2 L). The combined organic layers were sequentially washed with water (2×1 L), NaOH (1 L, 1 N aqueous solution), water (2×1 L), and brine (0.5 L). The organic phase was dried over Na₂SO₄, filtered, and concentrated under reduced pressure to afford the title compound (233 g, 99%) as a light yellow. ¹H NMR (300 MHz, DMSO-d6) δ 6.90 (d, 1H), 6.78 (d, 1H), 6.66 (dd, 1H), 3.70 (s, 3H), 3.60 (s, 3H), 3.20 (m, 1H), 2.80 (m, 2H), 2.40 (m, 1H), 2.08 (m, 1H), 1.80 (m, 1H), 1.58 (m, 1H), 1.40 (m, 1H), 0.80 (t, 3H).

EXAMPLE 21

Preparation of methyl (2S)-2-[(1S)-5-hydroxy-2,3-dihydro-1H-inden-1-yl]butanoate

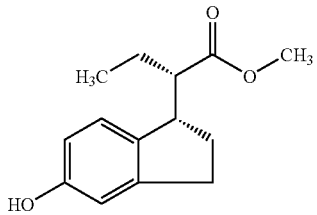

To a cold solution (ice water bath) of the compound prepared in Example 20 (233 g, 0.94 mol) in CH₂Cl₂ (2.5 L), was added AlCl₃ (630 g, 4.7 mol) slowly under argon. The internal temperature was kept below 20° C., and the color of the reaction turned purple. EtSH (345 mL, 4.7 mol) was added slowly via an addition funnel maintaining the internal temperature was below 15° C. After 2 h of stirring at below 20° C., the reaction was completed and was slowly poured into ice-water (2.5 L) with strong agitation. The organic phase was separated, and the aqueous phases was extracted with CH₂Cl₂ (1 L). The combined organic phases were washed with water (4×1 L) until pH 6.0-7.0, and then dried over Na₂SO₄, filtered, concentrated under reduced pressure, and then dried under vacuum to provide the title compound (216 g, 98%) as a white solid. ¹H NMR (300 MHz), (DMSO-d6) δ 9.10 (s, 1H), 6.78 (d, 1H), 6.58 (d, 1H), 6.50 (dd, 1H), 3.60 (s, 3H), 3.20 (q, 1H), 2.70 (m, 2H), 2.40 (m, 1H), 2.08 (m, 1H), 1.80 (m, 1H), 1.50 (m, 2H), 0.80 (t, 3H).

EXAMPLE 22

Preparation of methyl 4-bromo-3-oxopentanoate

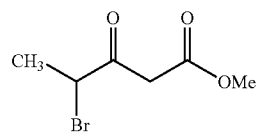

A dry three neck flask under an argon atmosphere was charged with a solution of methyl propionylacetate (20 g, 154 mmol) in CHCl₃ (100 mL). Using an addition funnel, bromine (7.9 mL, 24.6 g, 154 mmol) was added dropwise over a period of 2 h at 0° C. The reaction was then allowed to warm slowly to rt, and the reaction mixture was stirred overnight. A saturated solution of Na₂CO₃ (40 mL) was slowly added, and after stirring the reaction mixture for an additional 15 minutes, the solvents layers were separated and the aqueous layer was extracted with CH₂Cl₂ (50 mL). The combined organic layers were dried (Na₂SO₄), filtered, and concentrated under reduced pressure. The residue was then purified by silica gel flash chromatography (10:1 hexanes/EtOAc) to give the desired bromide as a yellow oil (25 g, 78%). ¹H NMR (CDCl₃): δ 1.80 (d, 3H), 3.64-3.92 (m, 2H), 3.78 (s, 3H), 4.61 (q, 1H).

EXAMPLE 23

Preparation of methyl (2-amino-5-methyl-1,3-thiazol-4-yl)acetate

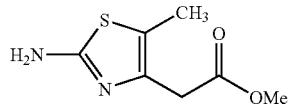

To a solution of bromide of Example 22 (18 g, 86 mmol) in toluene (100 mL) was added thiourea (10.5 g, 138 mmol). The reaction mixture was heated to 100° C. for 1 h, cooled to rt, and the solvent removed under reduced pressure. The residue was dissolved in CH$_2$Cl$_2$ (100 mL), a saturated solution NaHCO$_3$ (75 mL) added, and the mixture was vigorously stirred for 10 minutes. The organic layer was separated, dried (Na$_2$SO$_4$), filtered, and concentrated under reduced pressure. The residue was then recrystallized from CH$_2$Cl$_2$/hexanes to provide the product (10 g, 63%) as a white solid. (C$_7$H$_{10}$N$_2$O$_2$S): LC-MS, RT 0.76 min, M+H 187.0; $^1$H NMR (CDCl$_3$): δ 2.23 (s, 3H), 3.70 (s, 2H), 3.75 (s, 3H), 4.83-4.95 (broad s, 2H).

EXAMPLE 24

Preparation of methyl (2-bromo-5-methyl-1,3-thiazol-4-yl)acetate

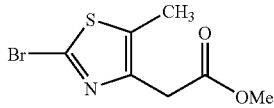

To a solution of CuBr$_2$ (4.03 g, 18.1 mmol) and t-butyl nitrite (2.82 mL, 23.8 mmol) in MeCN (210 mL) was added the compound of Example 23 (2.95 g, 15.9 mmol) at −20° C. The reaction mixture was slowly warmed to 15° C., at which point the evolution of N$_2$ was observed. After stirring for an additional 2 h at 15° C., the reaction mixture was diluted with Et$_2$O (400 mL) and washed with a 10% solution of HCl (200 mL). The solvent layers were separated, the aqueous layer re-extracted with Et$_2$O (2×300 mL), and the combined organic layers dried (MgSO$_4$), filtered, and concentrated under reduced pressure. The residue was then purified by silica gel flash chromatography (98:2, hexanes/EtOAc) to afford the title compound (1.6 g, 40%) as a colorless oil that solidified upon standing. (C$_7$H$_8$BrNO$_2$S): LC-MS, RT 2.56 min, M+H 250.3; $^1$H NMR (CDCl$_3$): δ 2.26 (s, 3H), 3.60 (s, 2H), 3.61 (s, 3H).

EXAMPLE 25

Preparation of 2-(2-bromo-5-methyl-1,3-thiazol-4-yl)ethanol

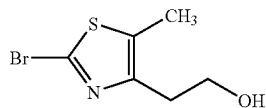

To a solution of ester prepared in Example 24 (3.80 g, 15.2 mmol) in CH$_2$Cl$_2$ (100 mL) was added DIBAL-H (33.4 mL, 33.4 mmol of a 1.0 M solution in toluene) at −78° C. After 15 minutes, the solution was warmed to 0° C. and stirred for an additional 90 minutes. An aqueous solution of 2N HCl (50 mL) was then added dropwise to quench the excess DIBAL-H. The solvent layers were separated and the aqueous layer extracted with CH$_2$Cl$_2$ (2×200 mL). The combined organic layers were dried (MgSO$_4$), filtered, and concentrated under reduced pressure. The residue was purified by silica gel flash chromatography (5:2 hexanes/EtOAc) to yield the title compound (2.5 g, 74%) as a yellowish oil that solidified upon standing. (C$_6$H$_8$BrNOS): LC-MS, RT 1.38 min, M+H 221.0; $^1$H NMR (CDCl$_3$): δ 2.31 (s, 3H), 2.82 (t, 2H), 2.90-3.00 (broad s, 1H), 3.89 (t, 2H).

EXAMPLE 26

Preparation of ethyl {(1S)-5-[2-(2-bromo-5-methyl-1,3-thiazol-4-yl)ethoxyl-2,3-dihydro-1H-inden-1-yl]acetate

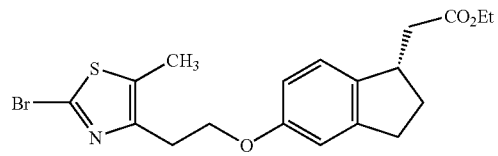

To a solution of Example 25 (975 mg, 4.39 mmol) and ethyl [(1S)-5-hydroxy-2,3-dihydro-1H-inden-1-yl]acetate (1.06 g, 4.83 mmol) in THF (20 mL) were added Ph$_3$P (1.88 g, 7.46 mmol) and ADDP (1.96 g, 7.46 mmol). The mixture was vigorously stirred at rt for 72 h, the solvent removed under reduced pressure, and the residue purified by silica gel flash chromatography (6:1 hexanes/EtOAc) to yield the product (1.4 g, 76%) as a colorless oil that solidified upon standing. (C$_{19}$H$_{22}$BrNO$_3$S): LC-MS, RT 3.92 min, M+H 424.5; $^1$H NMR (CDCl$_3$): δ 1.26 (t, 3H), 1.65-1.81 (m, 1H), 2.28-2.45 (m, 2H), 2.37 (s, 3H), 2.69 (dd, 1H), 2.75-2.93 (m, 2H), 3.07 (t, 2H), 3.44-3.56 (m, 1H), 4.15 (t, 2H), 4.18 (q, 2H), 6.67 (dd, 1H), 6.73 (d, 1H), 7.03 (d, 1H).

EXAMPLE 27

Preparation of ethyl ((1S)-5-{2-[2-(4-isopropylphenyl)-5-methyl-1,3-thiazol-4-yl]ethoxy}-2,3-dihydro-1H-inden-1-yl)acetate

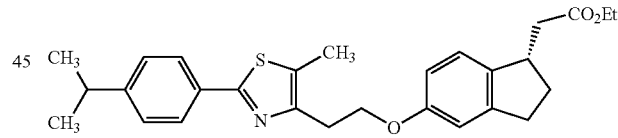

To a mixture of toluene (15 mL) and 1,4-dioxane (3 mL) were added Example 26 (300 mg, 0.708 mmol), 4-isopropylbenzene boronic acid (464 mg, 2.83 mmol), and PdCl$_2$ (dppf).CH$_2$Cl$_2$ (52 mg, 0.071 mmol). A flow of argon was passed through the mixture for 30 minutes, then a 2N solution of Na$_2$CO$_3$ (3.7 mL, 7.08 mmol) was added and the reaction was stirred at 75° C. for 18 h. The reaction mixture was then cooled to rt, diluted with EtOAc (200 mL), and washed with a saturated solution of NaHCO$_3$ (50 mL). The organic layer was dried (Na$_2$SO$_4$), filtered, and concentrated under reduced pressure. The residue was purified by silica gel flash chromatography (8:1 hexanes/EtOAc), to provide the product (305 mg, 93%) as a colorless oil. (C$_{28}$H$_{33}$NO$_3$S): LC-MS, RT 5.17 min, M+H 464.5; $^1$H NMR (CDCl$_3$): δ 1.17-1.31 (m, 3H), 1.26 (s, 3H), 1.27 (s, 3H), 1.65-1.82 (m, 1H), 2.30-2.43 (m, 2H), 2.46 (s, 3H), 2.72 (dd, 1H), 2.78-3.00 (m, 3H), 3.17 (t, 2H), 3.46-3.57 (m, 1H), 4.17 (q, 2H), 4.27 (t, 2H), 6.71 (d, 1H), 6.78 (s, 1H), 7.04 (d, 1H), 7.55 (AB quartet, 4H).

EXAMPLE 28

Preparation of ((1S)-5-{2-[2-(4-isopropylphenyl)-5-methyl-1,3-thiazol-4-yl]ethoxy}-2,3-dihydro-1H-inden-1-yl)acetic acid

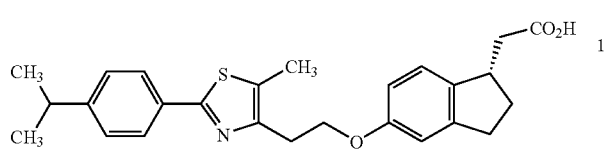

To a solution of Example 27 (305 mg, 0.657 mmol) in a mixture of THF (8 mL), water (8 mL), and EtOH (4 mL), was added LiOH (63 mg, 2.63 mmol). The reaction mixture was vigorously stirred for 24 h, diluted with water (20 mL), and washed with Et$_2$O (10 mL). The aqueous phase was then acidified to pH ~1 using 1N HCl, and then extracted with CH$_2$Cl$_2$ (4×50 mL). The combined organic layers were dried (Na$_2$SO$_4$), filtered, and concentrated under reduced pressure. The residue was then purified by silica gel flash chromatography (95:5 CH$_2$Cl$_2$/MeOH) to afford product (189 mg, 66%) as a white solid. (C$_{26}$H$_{29}$NO$_3$S): LC-MS, RT 3.95 min, M+H 436.4; $^1$H NMR (CDCl$_3$): δ 1.25 (s, 3H), 1.28 (s, 3H), 1.70-1.82 (m, 1H), 2.32-2.43 (m, 2H), 2.45 (s, 3H), 2.74-2.98 (m, 4H), 3.18 (t, 2H), 3.47-3.54 (m, 1H), 4.28 (t, 2H), 6.72 (dd, 1H), 6.78 (s, 1H), 7.08 (d, 1H), 7.51 (AB quartet, 4H).

EXAMPLE 29

Preparation of methyl [5-methyl-2-(4-methylphenyl)-1,3-thiazol-4-yl]acetate

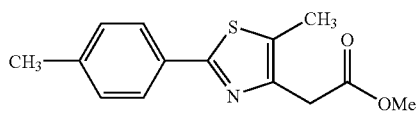

To a solution of bromide of Example 22 (1.15 g, 5.52 mmol) in toluene (20 mL) was added 4-methyl thiobenzamide (1.0 g, 6.6 mmol). The reaction mixture was heated to reflux for 15 h, cooled to rt, diluted with EtOAc (150 mL), and washed with a saturated solution of NaHCO$_3$ (50 mL), then with a saturated solution of NH$_4$Cl (50 mL). The organic layer was dried (Na$_2$SO$_4$), filtered, and concentrated under reduced pressure. The residue was then purified by silica gel flash chromatography (9:1 hexanes/EtOAc) to afford the product as a pinkish oil that solidified upon standing (1.14 g, 62%). $^1$H NMR (CDCl$_3$): δ 2.38 (s, 3H), 3.45 (s, 3H), 3.74 (s, 3H), 3.80 (s, 2H), 7.49 (AB quartet, 4H); R$_f$ (0.4, eluant 9:1 hexanes/EtOAc).

EXAMPLE 30

Preparation of 2-[5-methyl-2-(4-methylphenyl)-1,3-thiazol-4-yl]ethanol

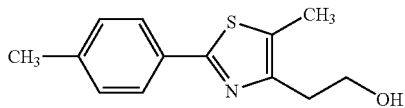

To a solution of the thiazole of Example 29 (1.14 g, 4.37 mmol) in THF (60 mL) at 0° C., was added portion-wise LiAlH$_4$ (663 mg, 17.5 mmol). After 30 minutes, the reaction mixture was warmed to rt and stirred for an additional 60 minutes. The reaction mixture was then cooled to 0° C., and the excess LiAlH$_4$ was quenched by dropwise addition of H$_2$O (5 mL), 1N NaOH (10 mL), and H$_2$O (5 mL) sequentially. The mixture was then diluted with a saturated solution of Rochelle's salt and extracted with EtOAc (4×75 mL). The combined organic phases were dried (Na$_2$SO$_4$), filtered, and concentrated under reduced pressure. The residue was purified by silica gel flash chromatography (3:2 hexanes/EtOAc) to afford the product as a white solid (830 mg, 82%). (C$_{13}$H$_{15}$NOS): LC-MS, RT 2.50 min, M+H 234.2; $^1$H NMR (CDCl$_3$): δ 2.34 (s, 3H), 2.37 (s, 3H), 2.83 (t, 2H), 3.92-4.01 (broad t, 2H), 4.04-4.15 (broad s, 1H), 7.45 (AB quartet, 4H).

The following compounds were synthesized using the procedures of Examples 22-30 described above.

EXAMPLE 31

{(1S)-5-[2-(5-Methyl-2-phenyl-1,3-thiazol-4-yl)ethoxy]-2,3-dihydro-1H-inden-1-yl}acetic acid

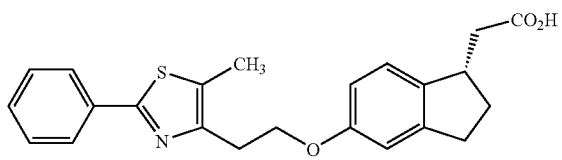

(C$_{23}$H$_{23}$NO$_3$S): LC-MS R.T. 3.56 min, M+H 394.2; $^1$H NMR (CDCl$_3$): δ 1.61-1.78 (m, 1H), 2.19-2.50 (m, 2H), 2.30 (s, 3H), 2.62-2.91 (m, 3H), 3.12 (t, 2H), 3.17-3.26 (m, 1H), 4.12 (t, 2H), 6.70 (1H, d), 6.79 (s, 1H), 6.98 (d, 1H), 7.21-7.40 (m, 3H), 7.74-7.83 (m, 2H).

EXAMPLE 32

((1S)-5-{2-[5-Methyl-2-(4-methylphenyl)-1,3-thiazol-4-yl]ethoxy}-2,3-dihydro-1H-inden-1-yl)acetic acid

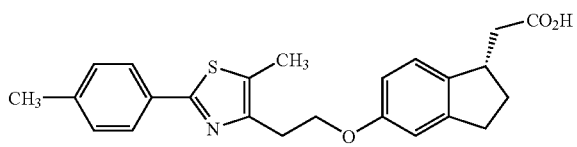

(C$_{24}$H$_{25}$NO$_3$S): LC-MS, RT 3.57 min, M+H 408.5; $^1$H NMR (CDCl$_3$): δ 1.61-1.68 (m, 1H), 2.29 (s, 3H), 2.36 (s, 3H), 2.25-2.37[hidden] (m, 2H), 2.63-2.79 (m, 3H), 3.09 (t, 2H), 3.35-3.47 (m, 1H), 4.18 (t, 2H), 6.60 (dd, 1H), 6.68 (s, 1H), 6.97 (d, 1H), 7.42 (AB quartet, 4H), 7.81-8.30 (br, 1H).

EXAMPLE 33

((1S)-5-{2-[2-(1,3-Benzodioxol-5-yl)-5-methyl-1,3-thiazol-4-yl]ethoxy}-2,3-dihydro-1H-inden-1-yl)acetic acid

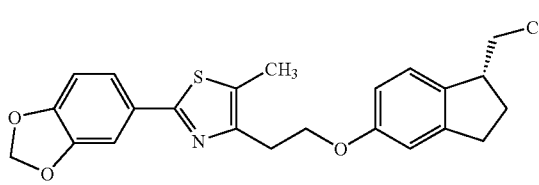

(C$_{24}$H$_{23}$NO$_5$S): LC-MS, RT 4.04 min, M+H 438.5; $^1$H NMR (CDCl$_3$): δ 1.71-1.83 (m, 1H), 2.36-2.51 (m, 2H), 2.45 (s, 3H), 2.76-2.96 (m, 3H), 3.15 (t, 2H), 3.48-3.58 (m, 1H), 4.29 (t, 2H), 6.00 (s, 2H), 6.72 (dd, 1H), 6.78 (s, 1H), 6.82 (d, 1H), 7.07 (d, 1H), 7.32-7.40 (m, 2H).

EXAMPLE 34

((1S)-5-{2-[2-(4-Methoxyphenyl)-5-methyl-1,3-thiazol-4-yl]ethoxy}-2,3-dihydro-1H-inden-1-yl)acetic acid

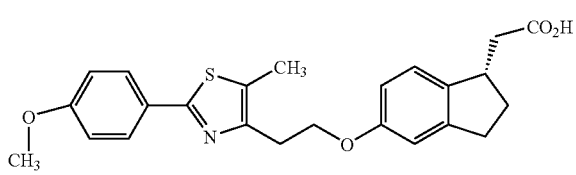

(C$_{24}$H$_{25}$NO$_4$S): LC-MS, RT 4.01 min, M+H 424.5; $^1$H NMR (CDCl$_3$): δ 1.67-1.82 (m, 1H), 2.43 (s, 3H), 2.34-2.47 (m, 2H), 2.72-2.95 (m, 3H), 3.09 (t, 2H), 3.42-3.57 (m, 1H), 3.84 (s, 3H), 4.13 (t, 2H), 6.72 (d, 1H), 6.79 (s, 1H), 7.12 (d, 1H), 7.37 (AB quartet, 4H).

EXAMPLE 35

[(1S)-5-(2-{5-Methyl-2-[4-(trifluoromethyl)phenyl]-1,3-thiazol-4-yl}-ethoxy)-2,3-dihydro-1H-inden-1-yl]acetic acid

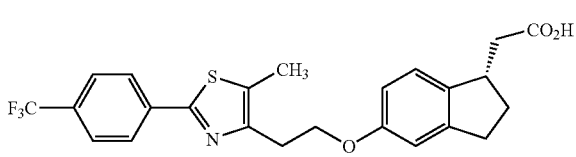

(C$_{24}$H$_{22}$F$_3$NO$_3$S): LC-MS, RT 4.47 min, M+H 462.4; $^1$H NMR (DMSO$_{d6}$): δ 1.63-1.81 (m, 1H), 2.28-2.43 (m, 2H), 2.50 (s, 3H), 2.69 (dd, 1H), 2.74-2.95 (m, 2H), 3.19 (t, 2H), 3.31-3.36 (m, 1H), 4.31 (t, 2H), 6.71 (dd, 1H), 6.78 (s, 1H), 7.08 (d, 1H), 7.87 (AB quartet, 4H).

EXAMPLE 36

((1S)-5-{2-[2-(4-Cyanophenyl)-5-methyl-1,3-thiazol-4-yl]ethoxy}-2,3-dihydro-1H-inden-1-yl)acetic acid

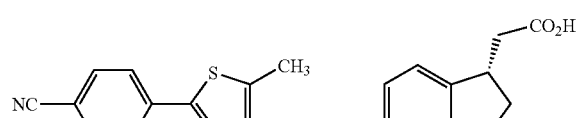

(C$_{24}$H$_{22}$N$_2$O$_3$S): LC-MS, RT 3.43 min, M+H 419.6; $^1$H NMR (CDCl$_3$): δ 1.68-1.85 (m, 1H), 2.31-2.49 (m, 2H), 2.51 (s, 3H), 2.77 (dd, 1H), 2.83-2.94 (m, 2H), 3.18 (t, 2H), 3.43-3.56 (m, 1H), 4.31 (t, 2H), 6.71 (dd, 1H), 6.79 (s, 1H), 7.10 (d, 1H), 7.86 (AB quartet, 4H).

EXAMPLE 37

((1S)-5-{2-[2-(4-Isopropylphenyl)-5-methyl-1,3-thiazol-4-yl]ethoxy}-2,3-dihydro-1H-inden-1-yl)acetic acid

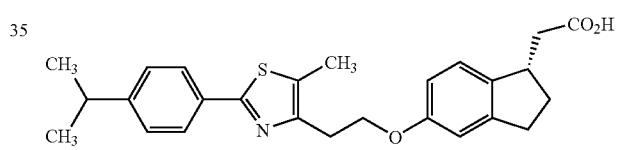

(C$_{26}$H$_{29}$NO$_3$S): LC-MS, RT 3.95 min, M+H 436.4; $^1$H NMR (CDCl$_3$): δ 1.25 (s, 3H), 1.28 (s, 3H), 1.70-1.82 (m, 1H), 2.32-2.43 (m, 2H), 2.45 (s, 3H), 2.74-2.98 (m, 4H), 3.18 (t, 2H), 3.47-3.54 (m, 1H), 4.28 (t, 2H), 6.72 (dd, 1H), 6.78 (s, 1H), 7.08 (d, 1H), 7.51 (AB quartet, 4H).

EXAMPLE 38

((1S)-5-{2-[2-(3-Chloro-4-fluorophenyl)-5-methyl-1,3-thiazol-4-yl]ethoxy}-2,3-dihydro-1H-inden-1-yl)acetic acid

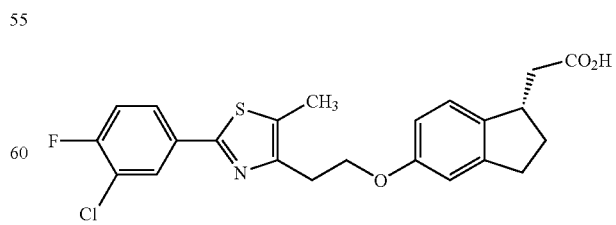

(C$_{23}$H$_{21}$ClFNO$_3$S): LC-MS, RT 3.89 min, M+H 446.4; $^1$H NMR (CDCl$_3$): δ 1.68-1.86 (m, 1H), 2.32-2.46 (m, 2H), 2.50 (s, 3H), 2.80 (dd, 1H), 2.84-2.96 (m, 2H), 3.18 (t, 2H), 3.47-

3.59 (m, 1H), 4.32 (t, 2H), 6.72 (d, 1H), 6.82 (s, 1H), 7.12 (d, 1H), 7.23 (t, 1H), 7.72-7.82 (m, 1H), 7.97-8.04 (m, 1H).

EXAMPLE 39

((1S)-5-{2-[2-(3,4-Dichlorophenyl)-5-methyl-1,3-thiazol-4-yl]ethoxy}-2,3-dihydro-1H-inden-1-yl)acetic acid

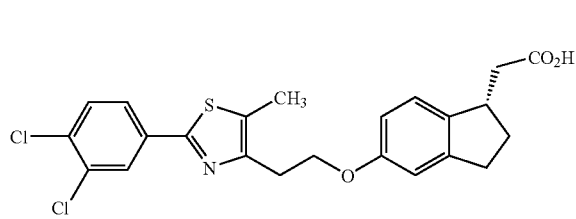

($C_{23}H_{21}Cl_2NO_3S$): LC-MS, RT 4.12 min, M+H 462.0; $^1$H NMR (CDCl$_3$): δ 1.74-1.88 (m, 1H), 2.36-2.48 (m, 2H), 2.50 (s, 3H), 2.73-2.93 (m, 3H), 3.19 (t, 2H), 3.48-3.55 (m, 1H), 4.30 (t, 2H), 6.71 (d, 1H), 6.79 (s, 1H), 7.09 (d, 1H), 7.52 (d, 1H), 7.61 (dd, 1H), 8.02 (d, 1H).

EXAMPLE 40

((1S)-5-{2-[2-(4-Fluorophenyl)-5-methyl-1,3-thiazol-4-yl]ethoxy}-2,3-dihydro-1H-inden-1-yl)acetic acid

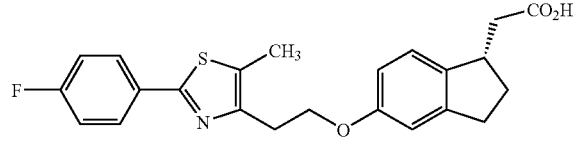

($C_{23}H_{22}FNO_3S$): LC-MS, RT 3.58 min, M+H 412.4; $^1$H NMR (CDCl$_3$): δ 1.70-1.77 (m, 1H), 2.37-2.45 (m, 1H), 2.44 (s, 3H), 2.70-2.90 (m, 4H), 3.16 (t, 2H), 3.47-3.52 (m, 1H), 4.27 (t, 2H), 6.70 (d, 1H), 6.76 (s, 1H), 7.00-7.10 (m, 3H), 7.82-7.87 (m, 2H).

EXAMPLE 41

((1S)-5-{2-[2-(3,4-Dimethylphenyl)-5-methyl-1,3-thiazol-4-yl]ethoxy}-2,3-dihydro-1H-inden-1-yl)acetic acid

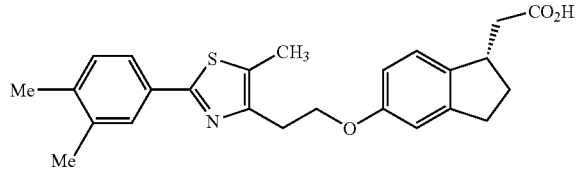

($C_{25}H_{27}NO_3S$): LC-MS, RT 4.39 min, M+H 422.3; $^1$H NMR (CDCl$_3$): δ 1.70-1.83 (m, 1H), 2.29 (s, 3H), 2.32 (s, 3H), 2.37-2.50 [hidden] (m, 2H), 2.46 (s, 3H), 2.70.-2.90 (m, 3H), 3.32 (t, 2H), 3.45-3.60 (m, 1H), 4.30 (t, 2H), 6.73 (d, 1H), 6.79 (s, 1H), 7.07 (d, 1H), 7.17 (d, 1H), 7.59 (d, 1H). 7.68 (s, 1H).

EXAMPLE 42

((1S)-5-{2-[2-(4-Acetylphenyl)-5-methyl-1,3-thiazol-4-yl]ethoxy}-2,3-dihydro-1H-inden-1-yl)acetic acid

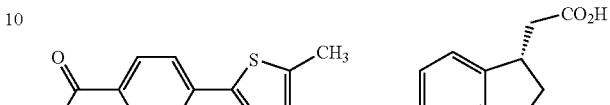

($C_{25}H_{25}NO_4S$): LC-MS, RT 4.01 min, M+H 436.3; $^1$H NMR (CDCl$_3$): δ 1.70-1.82 (m, 1H), 2.37-2.49 (m, 2H), 2.50 (s, 3H), 2.63 (s, 3H), 2.70-2.90 (m, 3H), 3.20 (t, 2H), 3.45-3.60 (m, 1H), 4.30 (t, 2H), 6.72 (d, 1H), 6.78 (s, 1H), 7.08 (d, 1H), 7.95-8.03 (m, 4H).

EXAMPLE 43

[(1S)-5-(2-{2-[4-(Dimethylamino)phenyl]-5-methyl-1,3-thiazol-4-yl}ethoxy)-2,3-dihydro-1H-inden-1-yl]acetic acid

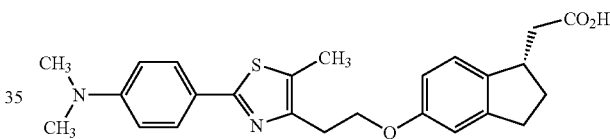

($C_{25}H_{28}N_2O_3S$): LC-MS, RT 2.95 min, M+H 437.2; $^1$H NMR (DMSO$_{d6}$): δ 1.53-1.65 (m, 1H), 2.12-2.24 (m, 2H), 2.36 (s, 3H), 2.63-2.84 (m, 3H), 2.94 (s, 6H), 3.03 (t, 2H), 3.27-3.38 (m, 1H), 4.18 (t, 2H), 6.65 (d, 1H), 6.75 (s, 1H), 7.08 (d, 1H), 7.17 (AB quartet, 4H).

EXAMPLE 44

((1S)-5-{2-[2-(3-Amino-4-methylphenyl)-5-methyl-1,3-thiazol-4yl]ethoxy}-2,3-dihydro-1H-inden-1-yl)acetic acid

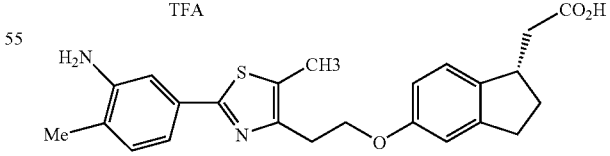

$C_{24}H_{26}N_2O_3S.C_2F_3O_2$): LC-MS, RT 3.50 min, M+H 423.3; $^1$H NMR (CD$_3$OD): δ 1.67-1.82 (m, 1H), 2.25-2.37 (m, 2H), 2.38 (s, 3H), 2.50 (s, 3H), 2.67-2.90 (m, 3H), 3.20 (t, 2H), 3.41-3.56 (m, 1H), 4.32 (t, 2H), 6.71 (d, 1H), 6.79 (s, 1H), 7.09 (d, 1H), 7.42 (d, 1H), 7.69 (dd, 1H), 7.77 (d, 1H).

EXAMPLE 45

((1S)-5-{2-[2-(2-Fluorophenyl)-5-methyl-1,3-thiazol-4-yl]ethoxy}-2,3-dihydro-1H-inden-1-yl)acetic acid

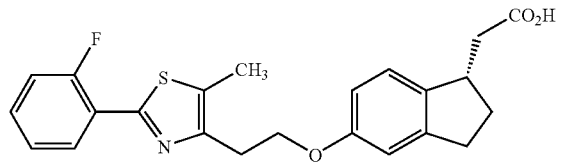

($C_{23}H_{22}FNO_3S$): LC-MS, RT 4.25 min, M+H 412.2; $^1$H NMR (CDCl$_3$): δ 1.70-1.82 (m, 1H), 2.37-2.48 (m, 2H), 2.49 (s, 3H), 2.74-2.94 (m, 3H), 3.21 (t, 2H), 3.42-3.60 (m, 1H), 4.31 (t, 2H), 6.72 (d, 1H), 6.79 (s, 1H), 7.06-7.35 (m, 4H), 8.21(t, 1H).

EXAMPLE 46

((1S)-5-{2-[2-(4-Chlorophenyl)-5-methyl-1,3-thiazol-4-yl]ethoxy}-2,3-dihydro-1H-inden-1-yl)acetic acid

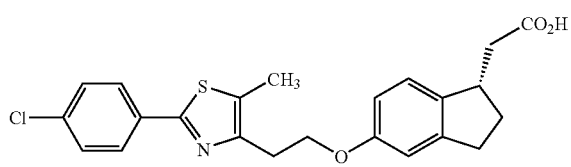

($C_{23}H_{22}ClNO_3S$): LC-MS, RT 4.44 min, M+H 428.2; $^1$H NMR (CDCl$_3$): δ 1.70-1.81 (m, 1H), 2.35-2.45 (m, 2H), 2.46 (s, 3H), 2.74-2.89 (m, 3H), 3.17 (t, 2H), 3.42-3.60 (m, 1H), 4.28 (t, 2H), 6.71 (d, 1H), 6.77 (s, 1H), 7.07 (d, 1H), 7.36 (d, 2H), 7.79 (d, 2H).

EXAMPLE 47

((1S)-5-{2-[2-(4-Ethoxyphenyl)-5-methyl-1,3-thiazol-4-yl]ethoxy}-2,3-dihydro-1H-inden-1-yl)acetic acid

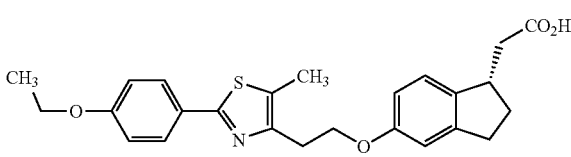

($C_{25}H_{27}NO_4S$): LC-MS, RT 3.55 min, M+H 438.5; $^1$H NMR (CDCl$_3$): δ 1.40 (t, 3H), 1.70-1.82 (m, 1H), 2.35-2.47 (m, 2H), 2.45 (s, 3H), 2.74-2.89 (m, 3H), 3.20 (t, 2H), 3.42-3.59 (m, 1H), 4.07 (q, 2H), 4.29 (t, 2H), 6.71 (d, 1H), 6.76 (s, 1H), 6.91 (d, 1H), 7.06 (d, 2H), 7.82 (d, 2H).

EXAMPLE 48

((1S)-5-{2-[2-(3,4-Dimethoxyphenyl)-5-methyl-1,3-thiazol-4-yl]ethoxy}-2,3-dihydro-1H-inden-1-yl) acetic acid

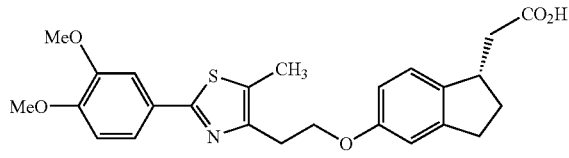

($C_{25}H_{27}NO_5S$): LC-MS, RT 3.86 min, M+H 454.2; $^1$H NMR (CDCl$_3$): δ 1.67-1.82 (m, 1H), 2.37-2.48 (m, 2H), 2.49 (s, 3H), 2.71-2.87 (m, 3H), 3.27 (t, 2H), 3.42-3.57 (m, 1H), 3.93 (s, 3H), 3.96 (s, 3H), 4.29 (t, 2H), 6.35-6.64 (broad s, 1H), 6.67 (d, 1H), 6.75 (s, 1H), 6.89 (d, 1H), 7.05 (d, 1H), 7.39 (d, 1H), 7.56 (s, 1H).

EXAMPLE 49

((1S)-5-{2-[5-Methyl-2-(3-methylphenyl)-1,3-thiazol-4-yl]ethoxy}-2,3-dihydro-1H-inden-1-yl)acetic acid

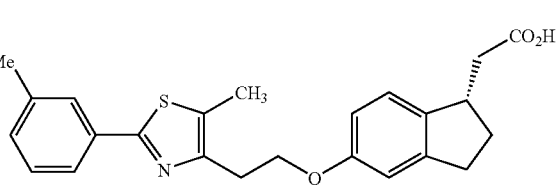

($C_{24}H_{25}NO_3S$): LC-MS, RT 3.71 min, M+H 408.2; $^1$H NMR (CDCl$_3$): δ 1.70-1.82 (m, 1H), 2.38-2.52 (m, 2H), 2.40 (s, 3H), 2.47 (s, 3H), 2.75-2.87 (m, 3H), 3.19 (t, 2H), 3.45-3.60 (m, 1H), 4.29 (t, 2H), 6.72 (d, 1H), 6.78 (s, 1H), 7.07 (d, 1H), 7.19 (d, 1H), 7.30 (t, 1H), 7.64 (d, 1H), 7.75 (s, 1H).

EXAMPLE 50

[(1S)-5-(2-{5-Methyl-2-[3-(trifluoromethyl)phenyl]-1,3-thiazol-4-yl}ethoxy)-2,3-dihydro-1H-inden-1-yl) acetic acid

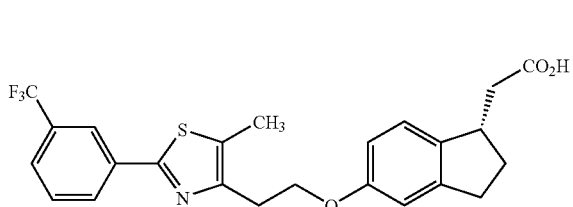

($C_{24}H_{22}F_3NO_3S$): LC-MS, RT 3.90 min, M+H 462.1; $^1$H NMR (CDCl$_3$): δ 1.70-1.82 (m, 1H), 2.38-2.48 (m, 2H), 2.49 (s, 3H), 2.75-2.87 (m, 3H), 3.19 (t, 2H), 3.44-3.59 (m, 1H), 4.30 (t, 2H), 6.72 (d, 1H), 6.79 (s, 1H), 7.07 (d, 1H), 7.52 (t, 1H), 7.61 (d, 1H), 8.01 (d, 1H), 8.13 (s, 1H).

EXAMPLE 51

((1S)-5-{2-[2-(3-Fluorophenyl)-5-methyl-1,3-thiazol-4-yl]ethoxy}-2,3-dihydro-1H-inden-1-yl)acetic acid

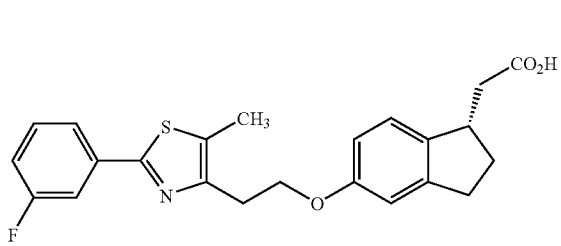

($C_{23}H_{22}FNO_3S$): LC-MS, RT 3.66 min, M+H 412.1; $^1$H NMR (CDCl$_3$): δ 1.70-1.82 (m, 1H), 2.39-2.47 (m, 2H), 2.48 (s, 3H), 2.76-2.87 (m, 3H), 3.18 (t, 2H), 3.45-3.60 (m, 1H), 4.30 (t, 2H), 6.72 (d, 1H), 6.78 (s, 1H), 7.04-7.09 (m, 2H), 7.36-7.42 (m, 1H), 7.58-7.62 (m, 2H).

EXAMPLE 52

((1S)-5-{2-[2-(3,5-Dimethylphenyl)-5-methyl-1,3-thiazol-4-yl]ethoxy}-2,3-dihydro-1H-inden-1-yl) acetic acid

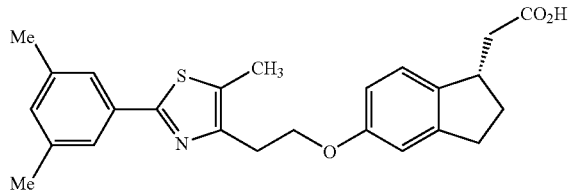

($C_{25}H_{27}NO_3S$): LC-MS, RT 3.88 min, M+H 422.2; $^1$H NMR (CDCl$_3$): δ 1.72-1.84 (m, 1H), 2.36 (s, 6H), 2.37-2.45 (m, 2H), 2.46 (s, 3H), 2.75-2.87 (m, 3H), 3.19 (t, 2H), 3.45-3.60 (m, 1H), 4.28 (t, 2H), 6.72 (d, 1H), 6.79 (s, 1H), 7.01 (s, 1H), 7.07 (d, 1H), 7.48 (s, 2H).

EXAMPLE 53

[(1S)-5-(2-{5-Methyl-2-[4-(trifluoromethoxy)phenyl]-1,3-thiazol-4-yl}ethoxy)-2,3-dihydro-1H-inden-1-yl]acetic acid

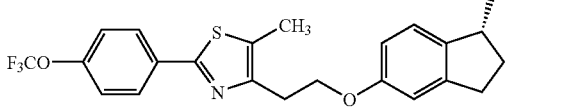

($C_{24}H_{22}F_3NO_4S$): LC-MS, RT 3.95 min, M+H 478.1; $^1$H NMR (CDCl$_3$): δ 1.72-1.84 (m, 1H), 2.38-2.46 (m, 2H), 2.47 (s, 3H), 2.75-2.87 (m, 3H), 3.18 (t, 2H), 3.45-3.60 (m, 1H), 4.29 (t, 2H), 6.72 (d, 1H), 6.77 (s, 1H), 7.07 (d, 1H), 7.24 (d, 2H), 7.88 (d, 2H).

EXAMPLE 54

((1S)-5-{2-[2-(3-Methoxyphenyl)-5-methyl-1,3-thiazol-4-yl]ethoxy}-2,3-dihydro-1H-inden-1-yl) acetic acid

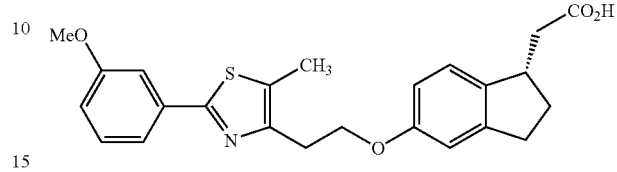

($C_{24}H_{25}NO_4S$): LC-MS, RT 3.56 min, M+H 424.2; $^1$H NMR (CDCl$_3$): δ 1.70-1.82 (m, 1H), 2.37-2.52 (m, 2H), 2.49 (s, 3H), 2.75-2.87 (m, 3H), 3.19 (t, 2H), 3.45-3.57 (m, 1H), 3.87 (s, 3H), 4.30 (t, 2H), 6.72 (d, 1H), 6.79 (s, 1H), 6.95 (d, 1H), 7.10 (d, 1H), 7.32 (t, 1H), 7.40-7.45 (m, 2H).

EXAMPLE 55

((1S)-5-{2-[2-(1,1'-Biphenyl-4-yl)-5-methyl-1,3-thiazol-4-yl]ethoxy}-2,3-dihydro-1H-inden-1-yl) acetic acid

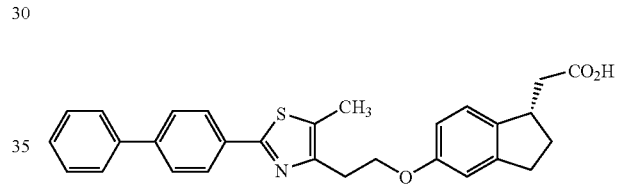

($C_{29}H_{27}NO_3S$): LC-MS, RT 3.96 min, M+H 470.3; $^1$H NMR (CDCl$_3$): δ 1.70-1.81 (m, 1H), 2.38-2.48 (m, 2H), 2.49 (s, 3H), 2.75-2.87 (m, 3H), 3.20 (t, 2H), 3.43-3.59 (m, 1H), 4.31 (t, 2H), 6.72 (d, 1H), 6.79 (s, 1H), 7.08 (d, 1H), 7.36 (t, 1H), 7.45 (t, 2H), 7.61-7.65 (m, 4H), 7.93 (d, 2H).

EXAMPLE 56

Preparation of N-benzoylalanine

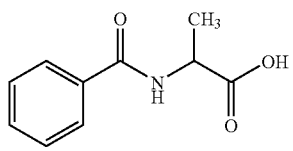

To a solution of sodium hydroxide (8.98 g, 224.49 mmol) in water (112.25 mL), DL-Alanine (10 g, 112.25 mmol) was added at rt. The resulting solution was heated at 75° C. and the benzoyl chloride (15.77 g, 112.25 mmol) was slowly added. The reaction was heated for 30 min, and cooled to 0° C. with an ice bath. Conc. HCl was added to adjust the pH to 1, then the white solid was filtrated through a fritted glass funnel and vacuum dried with P$_2$O$_5$ overnight. No purification was needed. Gave N-benzoylalanine (19.6 g, 90.4% yield) as white solid. $^1$H NMR (DMSO-d$_6$) δ 12.61 (s br, 1H), 8.64 (d, 1H), 7.87-7.85 (m, 2H), 7.52-7.43 (m, 3H), 4.40 (q, 1H), 1.39 (d, 3H).

EXAMPLE 57

Preparation of ethyl 4-(benzoylamino)-3-oxopentanoate

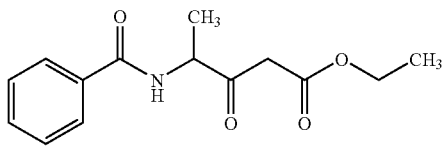

In the first flask, N-benzoylalanine (2 g, 10.35 mmol) was dissolved in THF (20 mL) and carbonyl diimidazole (CDI) (1.84 g, 11.39 mmol) was added. The resulting mixture was stirred 1 h at rt and cooled down to −78° C. Into a second flask, ethyl acetate (3.83 g, 43.48 mmol) in THF (40 mL) was cooled down to −78° C. and LDA (2M in THF, 24.3 mL, 48.51 mmol) pre-cooled to −78° C. was added. The resulting solution was stirred 30 minutes at −78° C. and the lithium enolate generated was cannulated into the first flask. The resulting white slurry was stirred 30 minutes at −78° C. and warmed up to −10° C. The reaction was quenched with a saturated aqueous solution of NH$_4$Cl. Phases were separated and the organics were dried over MgSO$_4$ and solvents removed under reduced pressure. The crude product was carried on to the next step without purification. Gave ethyl 4-(benzoylamino)-3-oxopentanoate (2.6 g, 95.5% yield) as a white solid. ES-MS m/z 263.4 ((MH)$^+$); HPLC RT (min) 1.53; $^1$H NMR (Acetone-d$_6$) δ 8.13 (s br, 1H), 7.93-7.91 (m, 2H), 7.58-7.43 (m, 3H), 4.72 (m, 1H), 4.19-4.01 (q, 2H), 3.67 (s, 2H), 1.47 (d, 3H), 1.15 (t, 3H).

EXAMPLE 58

Preparation of ethyl (4-methyl-2-phenyl-1,3-oxazol-5-yl)acetate

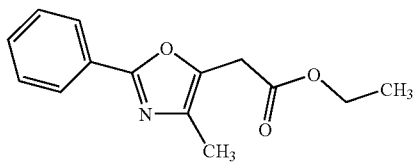

To a crude mixture of ethyl 4-(benzoylamino)-3-oxopentanoate (0.6 g, 2.28 mmol) in DMF (4 mL) at rt was added POCl$_3$ (1.04 g, 6.84 mmol). The resulting solution was heated at 90° C. for 1 h, then cooled down to rt, and poured into ice for 30 minutes. The aqueous solution was carefully added to a saturated aqueous solution of NaHCO$_3$. Phases were separated with EtOAc and the combined organic extracts were dried over MgSO$_4$, and the solvent removed under reduced pressure. The crude material was purified on Biotage small column using a solvent gradient of 0 to 50% EtOAc/Hexane. Gave ethyl (4-methyl-2-phenyl-1,3-oxazol-5-yl)acetate (0.269 g 48% yield) as yellowish oil. ES-MS m/z 246.2 ((MH)$^+$); HPLC RT (min) 2.77; $^1$H NMR (CDCl$_3$) δ 8.01-7.98 (m, 2H), 7.45-7.41 (m, 3H), 4.20 (q, 2H), 3.71 (s, 2H), 2.21 (s, 3H), 1.28 (t, 3H).

EXAMPLE 59

Preparation of 2-(4-methyl-2-phenyl-1,3-oxazol-5-yl)ethanol

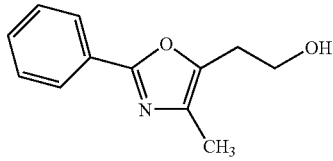

Ethyl (4-methyl-2-phenyl-1,3-oxazol-5-yl)acetate (0.922 g, 3.76 mmol) in THF (6 mL) at rt was added LiBH$_4$ (2M/THF, 9.41 mL, 4.70 mmol). The reaction was stirred overnight at rt, then treated with 2N HCl until pH 7. The solvent THF was removed under reduced pressure, EtOAc was added, and phases separated. The combined organics extracts were dried over MgSO$_4$ and solvent concentrated in vacuo. The crude material was purified by Biotage using a gradient of 10 to 100% EtOAc/Hexane as solvent mixture. Gave 2-(4-methyl-2-phenyl-1,3-oxazol-5-yl)ethanol (0.193 g, 25% yield) as colorless oil. ES-MS m/z 204.2 (MH)$^+$); HPLC RT (min) 2.02; $^1$H NMR (Acetone-d$_6$) δ 7.98-7.95 (m, 2H), 7.52-7.42 (m, 3H), 3.95 (s br, 1H), 3.82 (t, 2H)m, 2.90 (t, 2H), 2.13 (s, 3H).

EXAMPLE 60

Preparation of ethyl {(1S)-5-[2-(4-methyl-2-phenyl-1,3-oxazol-5-yl)ethoxy]-2,3-dihydro-1H-inden-1-yl}acetate

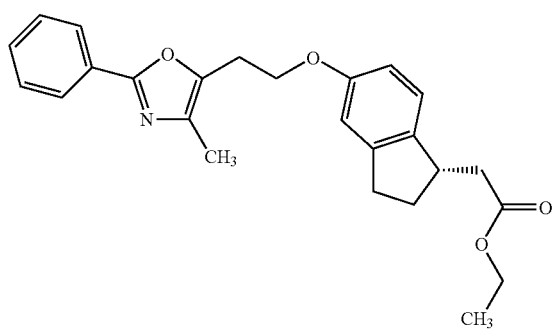

ADDP (0.205 g, 0.81 mmol) was added to a mixture of PPh$_3$ (0.212 g, 0.81 mmol), ethyl [(1S)-5-hydroxy-2,3-dihydro-1H-inden-1-yl]acetate (0.107 g, 0.49 mmol), and 2-(4-methyl-2-phenyl-1,3-oxazol-5-yl)ethanol (0.110 g, 0.54 mmol) in THF (5 mL). The reaction was stirred overnight at rt, and additional ADDP (0.136 g, 0.54 mmol) and PPh$_3$ (0.141 g 0.54 mmol) were added with CH$_2$Cl$_2$ (5 mL). The solution was stirred for 24h at rt and filtered. The filtrate was evaporated and the resulting mixture was purified by Biotage using a gradient 0 to 50% EtOAc/hexane. Gave ethyl {(1S)-5-[2-(4-methyl-2-phenyl-1,3-oxazol-5-yl)ethoxy]-2,3-dihydro-1H-inden-1-yl}acetate (0.145g, 66% yield) as yellowish oil. ES-MS m/z 406.2 ((MH)$^+$); HPLC RT (min) 3.89; $^1$H NMR (Acetone-d$_6$) δ 7.85-7.82 (m, 2H), 7.36-7.30 (m, 3H), 6.94 (d, 1H), 6.65 (s, 1H), 6.60-6.55 (m, 1H), 4.10 (t, 2H), 3.98 (q, 2H), 3.31-3.27 (m, 1H), 3.03 (t, 2H), 3.27-2.51 (m, 3H), 2.24-2.14 (m, 2H), 2.18 (s, 3H), 1.58-1.53 (m, 1H), 1.08 (t, 3H).

EXAMPLE 61

Preparation of {(1S)-5-[2-(4-methyl-2-phenyl-1,3-oxazol-5-yl)ethoxy]-2,3-dihydro-1H-inden-1-yl}acetic acid

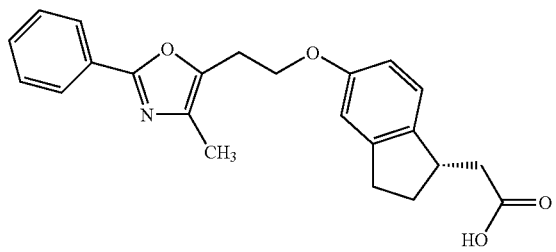

Ethyl {(1S)-5-[2-(4-methyl-2-phenyl-1,3-oxazol-5-yl)ethoxy]-2,3-dihydro-1H-inden-1-yl}acetate (0.135 g, 0.33 mmol) was dissolved in EtOH (6 mL), and LiOH (0.024 g, 1.0 mmol) was added. Water was added (3 mL) and THF was added until the cloudy solution became clear. The resulting mixture was stirred overnight at rt. HCl (2N) was added to adjust the pH to 2, then extracted three times with ethyl acetate. The organic layers were combined, dried, and concentrated to give the {(1S)-5-[2-(4-methyl-2-phenyl-1,3-oxazol-5-yl)ethoxy]-2,3-dihydro-1H-inden-1-yl}acetic acid (0.039 g, 30.6% yield) as colorless oil. ES-MS m/z 378.2 ((MH)$^+$); HPLC RT (min) 3.22; $^1$H NMR (Acetone-d$_6$) δ 8.1 (s br 1H) 8.0-7.95 (m, 2H), 7.52-7.43 (m, 3H), 7.15(d, 1H), 6.81 (s, 1H), 6.73 (d, 1H), 4.27 (t, 2H) 3.47-3.40 (m, 1H), 3.18 (t, 2H), 2.90-2.68 (m, 3H), 2.41-2.29 (m, 2H), 2.18 (s, 3H), 1.77-1.68 (m, 1H).

By using the procedure described above for Examples 56-61 and substituting the appropriate starting materials, the following compounds were similarly prepared and characterized.

EXAMPLE 62

N-(4-methylbenzoyl)alanine

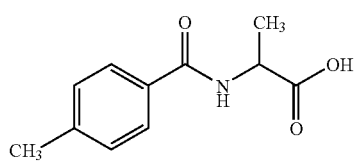

$^1$H NMR (DMSO-d$_6$) δ 12.60 (s br, 1H), 8.57 (d, 1H), 7.81 (d, 2H), 7.28 (d, 2H), 4.38 (q, 1H), 2.35 (s, 3H), 1.38 (d, 3H).

EXAMPLE 63

N-(3-fluoro-4-methylbenzoyl)alanine

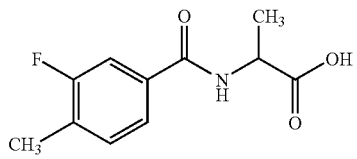

$^1$H NMR (DMSO-d$_6$) δ 12.54 (s br, 1H), 8.67 (d, 1H), 7.65-7.62 (m, 2H), 7.39 (t, 1H), 4.38 (q, 1H), 2.27 (s, 3H), 1.38 (d, 3H).

EXAMPLE 64

N-[4-(trifluoromethyl)benzoyl]alanine

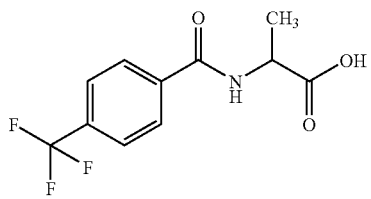

$^1$H NMR (DMSO-d$_6$) δ 12.64 (s br, 1H), 8.91 (d, 1H), 8.08 (d, 2H), 7.85 (d, 2H), 4.42 (q, 1H), 1.40 (d, 3H).

EXAMPLE 65

Ethyl 4-[(4-methylbenzoyl)amino]-3-oxopentanoate

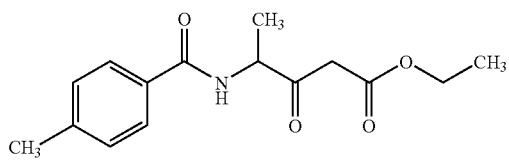

ES-MS m/z 278.38 ((MH)$^+$); HPLC RT (min) 2.04. $^1$H NMR (Acetone-d$_6$) δ 8.08 (s br, 1H), 7.90 (d, 2H), 7.28 (d, 2H), 4.72-4.67 (m, 1H), 4.13 (q, 2H), 3.66 (s, 2H), 2.40 (s, 3H), 1.41 (d, 3H), 1.12 (t, 3H).

EXAMPLE 66

Ethyl 4-[(3-fluoro-4-methylbenzoyl)amino]-3-oxo-pentanoate

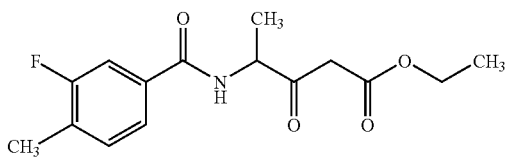

ES-MS m/z 296.4 ((MH)$^+$); HPLC RT (min) 2.26. $^1$H NMR (Acetone-$d_6$) δ 7.75-7.60 (m, 2H), 7.38 (t, 1H), 4.20 (q, 2H), 3.65 (s, 2H), 2.23 (s, 3H), 1.45 (d, 3H), 1.20 (t, 3H).

EXAMPLE 67

Ethyl 3-oxo-4-{[4-(trifluoromethyl)benzoyl]amino}pentanoate

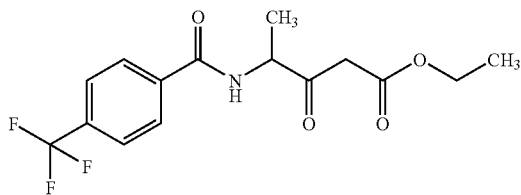

ES-MS m/z 332.4 ((MH)$^+$); HPLC RT (min) 2.45. $^1$H NMR (Acetone-$d_6$) δ 8.14 (d, 2H), 7.84 (d, 2H), 4.80-4.74 (m, 2H), 4.20 (q, 2H), 3.70 (s, 2H), 1.48 (d, 3H), 1.21 (t, 3H).

EXAMPLE 68

Ethyl [4-methyl-2-(4-methylphenyl)-1,3-oxazol-5-yl]acetate

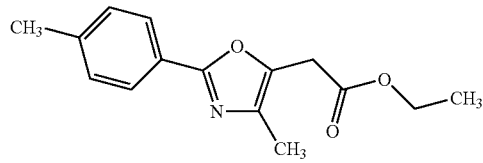

ES-MS m/z 260.2 ((MH)$^+$); HPLC RT (min) 2.96. $^1$H NMR (Acetone-$d_6$) δ 7.86 (d, 2H), 7.30 (d, 2H), 4.15 (q, 2H), 3.81 (s, 2H), 2.37 (s, 3H), 2.14 (s, 3H), 1.24 (t, 3H).

EXAMPLE 69

Ethyl [2-(3-fluoro-4-methylphenyl)-4-methyl-1,3-oxazol-5-yl]acetate

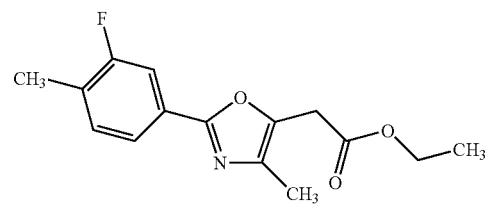

ES-MS m/z 278.3 ((MH)$^+$); HPLC RT (min) 2.89. $^1$H NMR (Acetone-$d_6$) δ 7.69 (d, 1H), 7.60 (d, 1H), 7.37 (t, 1H), 4.15 (q, 2H), 3.83 (s, 2H), 2.31 (s, 3H), 2.15 (s, 3H), 1.23 (t, 3H).

EXAMPLE 70

Ethyl {4-methyl-2-[4-(trifluoromethyl)phenyl]-1,3-oxazol-5-yl}acetate

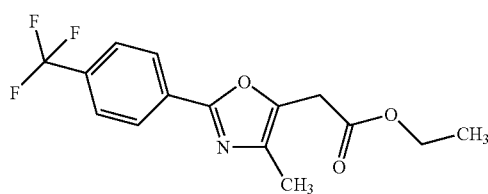

ES-MS m/z 314.3 ((MH)$^+$); HPLC RT (min) 3.27. $^1$H NMR (Acetone-$d_6$) δ 8.18 (d, 2H), 7.84 (d, 2H), 4.17 (q, 2H), 3.88 (s, 2H), 2.20 (s, 3H), 1.23 (t, 3H).

EXAMPLE 71

2-[4-Methyl-2-(4-methylphenyl)-1,3-oxazol-5-yl]ethanol

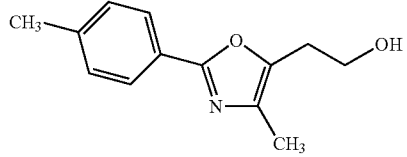

ES-MS m/z 218.2 ((MH)$^+$); HPLC RT (min) 2.35. $^1$H NMR (Acetone $d_6$) δ 7.85 (d, 2H), 7.27 (d, 2H), 3.99 (s br, 1H), 3.83 (t, 2H), 2.90 (t, 2H), 2.37 (s, 3H), 2.12 (s, 3H).

Example 72

2-[2-(3-Fluoro-4-methylphenyl)-4-methyl-1,3-oxazol-5-yl]ethanol

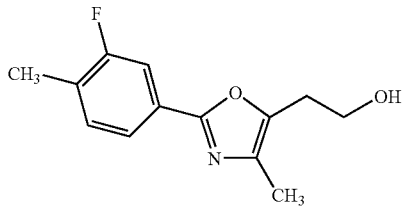

ES-MS m/z 236.2 ((MH)+); HPLC RT (min) 2.46. ¹H NMR (CDCl₃) δ 7.54 (d, 1H), 7.43 (d, 1H), 7.17 (t, 1H), 3.91 (d, 2H), 3.09 (s br, 1H), 2.88 (t, 2H), 2.29 (s, 3H), 2.13 (s, 3H).

EXAMPLE 73

2-{4-Methyl-2-[4-(trifluoromethyl)phenyl]-1,3-oxazol-5-yl}ethanol

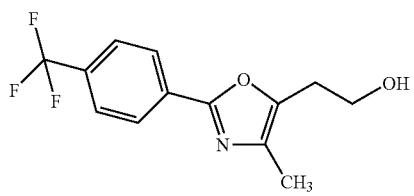

ES-MS m/z 272.2 ((MH)+); HPLC RT (min) 2.71. ¹H NMR (CDCl₃) δ 8.03 (2, 2H), 7.66 (d, 2H), 3.95 (t, 2H), 2.96 (t, 2H), 2.21 (s, 3H), 1.97 (s br, 1H).

EXAMPLE 74

Ethyl [(1S)-5-(2-{4-methyl-2-[4-(trifluoromethyl)phenyl]-1,3-oxazol-5-yl}ethoxy)-2,3-dihydro-1H-inden-1-yl]acetate

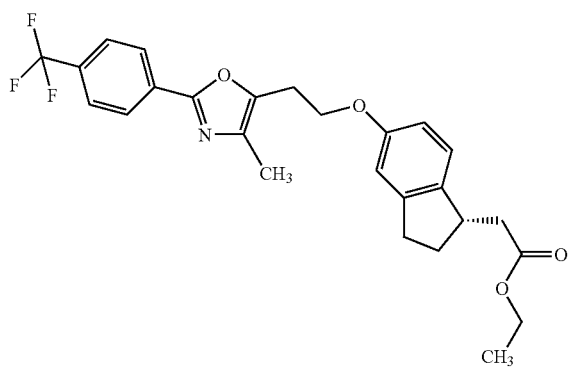

ES-MS m/z 474.5 ((MH)+); HPLC RT (min) 4.10. ¹H NMR (Acetone-d₆) δ 8.16 (d, 2H), 7.83 (d, 2H), 7.09 (d, 1H), 6.80 (s, 1H), 6.72 (dd, 1H), 4.28 (t, 2H), 4.12 (q, 2H), 3.46-3.41 (m, 1H), 3.21 (t, 2H), 2.86-2.65 (m, 3H), 2.39-2.26 (m, 2H), 2.20 (s, 3H), 1.75-1.63 (m, 1H), 1.22 (t, 3H).

EXAMPLE 75

Ethyl [(1S)-5-{2-[4-methyl-2-(4-methylphenyl)-1,3-oxazol-5-yl]ethoxy}-2,3-dihydro-1H-inden-1-yl)acetate

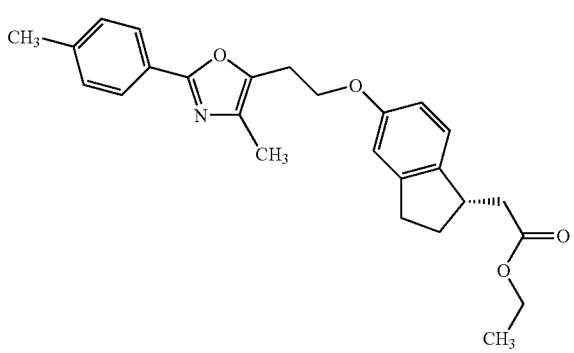

TCL Rf=0.22 Hexane/EtOAc 4:1

EXAMPLE 76

Ethyl ((1S)-5-{2-[2-(3-fluoro-4-methylphenyl)-4-methyl-1,3-oxazol-5-yl]ethoxy}-2,3-dihydro-1H-inden-1-yl)acetate

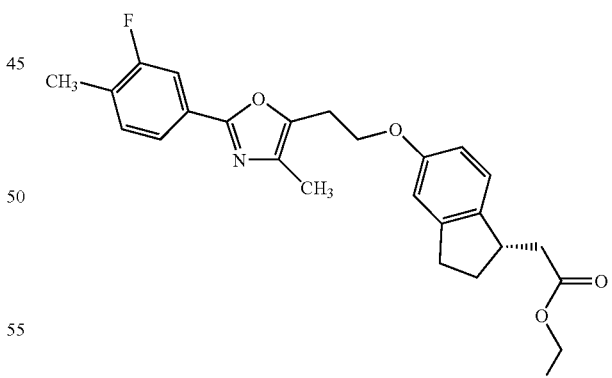

ES-MS m/z 438.2 ((MH)+); HPLC RT (min) 4.18. ¹H NMR (Acetone-d₆) δ 6.67 (dd, 1H), 7.59 (dd, 1H), 7.37 (t, 1H), 7.08 (d, 1H), 6.80 (s, 1H), 6.72 (dd, 1H), 4.26 (t, 2H), 4.12 (q, 2H), 3.46-3.38 (m, 1H), 3.17 (t, 2H), 2.89-2.65 (m, 3H), 2.39-2.23 (m, 5H), 2.17 (s, 3H), 1.75-1.63 (m, 1H), 1.23 (t, 3H).

EXAMPLE 77

((1S)-5-{2-[4-Methyl-2-(4-methylphenyl)-1,3-ox-azol-5-yl]ethoxy}-2,3-dihydro-1H-inden-1-yl)acetic acid

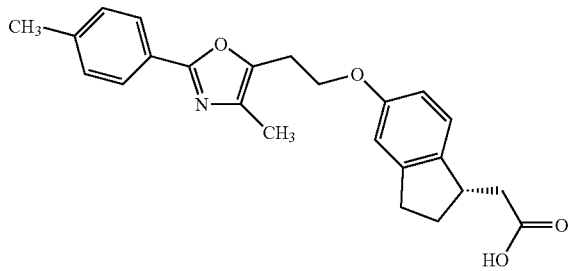

ES-MS m/z 392.2 ((MH)+); HPLC RT (min) 3.36. ¹H NMR (Acetone-d₆) δ 7.72 (d, 2H), 7.15 (d, 2H). 6.99 (d, 1H), 6.67 (s, 1H), 6.59 (dd, 1H), 4.12 (t, 2H), 3.33-3.28 (m, 1H), 3.03 (t, 2H), 2.73-2.54 (m, 3H), 2.27-2.21 (m, 5H), 2.02 (s, 3H), 1.64-1.54 (m, 1H).

EXAMPLE 78

((1S)-5-{2-[2-(3-Fluoro-4-methylphenyl)-4-methyl-1,3-oxazol-5-yl]ethoxy}-2,3-dihydro-11-inden-1-yl) acetic acid

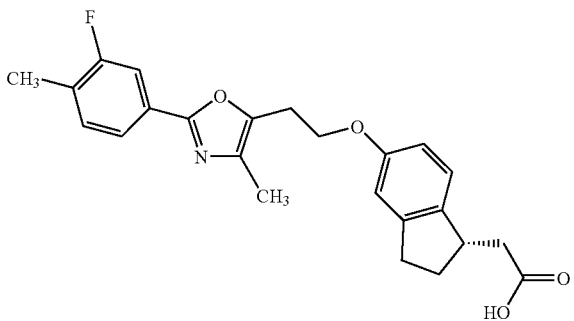

ES-MS m/z 410.2 ((MH)+); HPLC RT (min) 3.49. ¹H NMR (Acetone-d₆) δ 7.68 (dd, 1H), 7.59 (dd, 1H), 7.36 (t, 1H), 7.12 (d, 1H), 6.80 (s, 1H), 6.72 (dd, 1H), 4.26 (t, 2H), 3.47-3.41 (m, 1H, 3.18 (t, 2H), 2.86-2.67 (m, 3H), 2.40-2.28 (m, 5H), 2.17 (s, 3H), 1.18-1.65 (m, 1H).

EXAMPLE 79

[(1S)-5-(2-{4-Methyl-2-[4-(trifluoromethyl)phenyl]-1,3-oxazol-5-yl}ethoxy)-2,3-dihydro-1H-inden-1-yl] acetic acid

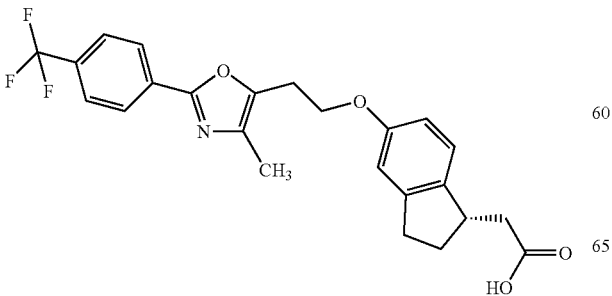

ES-MS m/z 446.5 ((MH)+); HPLC RT (min) 3.47. ¹H NMR (Acetone-d₆) δ 8.17 (d, 2H), 7.84 (d, 2H), 7.13 (s, 1H), 6.80 (s, 1H), 6.72 (dd, 1H), 4.28 (t, 2H), 3.46-3.41 (m, 1H), 3.21 (t, 2H), 2.86-2.67 (m, 3H), 2.40-2.28 (m, 2H), 2.20 (s, 3H), 1.77-1.67 (m, 1H).

EXAMPLE 80

Preparation of methyl 3-[(3-bromo-4-methylbenzoyl)amino]-4-oxopentanoate

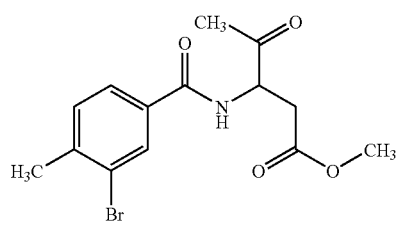

To a suspension of L-aspartic acid β-methyl ester hydrochloride (Sigma, 5.0 g, 27.23 mmol) in chilled (<5° C.) CH₂Cl₂ (150 mL) was added Et₃N (8.33 g, 81.70 mmol) in a steady flow followed by a slow addition of Me₃SiCl (6.51 g, 59.92 mmol). The mixture was warmed to 25° C. and stirred for 1 h, cooled again (<10° C.), and 3-bromo4-methylbenzoyl chloride (6.36 g, 27.23 mmol) was added dropwise. The mixture was allowed to warm to ambient temperature slowly with stirring for 16 h. The reaction mixture was then diluted with CH₂Cl₂ (150 mL) and washed with 1N HCl (50 mL), brine (50 mL), and dried over Na₂SO₄. The resultant amide product (8.9 g, 95%), a white solid, was obtained after solvent removal and drying under vacuum. It was then dissolved in pyridine (50 mL) and DMAP (0.17 g, 1.38 mmol) was added. Acetic anhydride (26 mL) was added slowly and then the reaction was heated at 90° C. for 2 h. The cooled solution was poured into 200 mL ice water and extracted with EtOAc. The organic layer was washed with 2N HCl (3×100 mL) and 1N NaOH (100 mL), dried over MgSO₄, and concentrated to afford the title compound as a off white solid which was taken to the next step (Example 81).

EXAMPLE 81

Preparation of methyl [2-(3-bromo-4-methylphenyl)-5-methyl-1,3-oxazol-4-yl]acetate

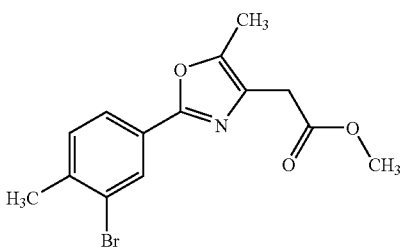

The total crude material prepared in Example 80 was dissolved in acetic anhydride (25 mL) followed by slow addition of conc. $H_2SO_4$ (1 mL). The pot temperature reached 90° C. The reaction was then held at 90° C. for 1 h, cooled, and the acetic anhydride removed in vacuo. The residue was poured into ice water (250 mL) and extracted with EtOAc (300 mL total). The organic layer was then extracted with 1 N HCl (100 mL), saturated $NaHCO_3$ (100 mL) and brine, separated, then dried with $NaSO_4$ and concentrated to afford the title ester (4.6 g). The crude product used in the next step (Example 82).

EXAMPLE 82

Preparation of 2-[2-(3-bromo-4-methylphenyl)-5-methyl-1,3-oxazol-4-yl]ethanol

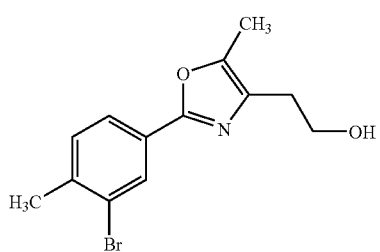

The oxazole ester prepared in Example 81 (4.7 g, 14.5 mmol) was dissolved in THF (20 mL), and $LiBH_4$ (10.15 mL, 20.3 mmol, 2M solution in THF) was added slowly while maintaining the temperature below 45° C. Upon completion the solvent was reduced to half the volume and then the reaction mixture was poured into ice water (200 mL). The mixture was then acidified by slowly adding 1 N HCl and the aqueous phase, extracted with ethyl acetate. The organic phase was dried ($Na_2SO_4$) and filtered and the solvents were evaporated under vacuum and the residue was purified by Biotage to obtain desired oxazole alcohol (3.8 g, 87%).

EXAMPLE 83

Preparation of ethyl ((1S)-5-{2-[2-(3-bromo-4-methylphenyl)-5-methyl-1,3-oxazol-4-yl]ethoxy}-2,3-dihydro-1H-inden-1-yl)acetate

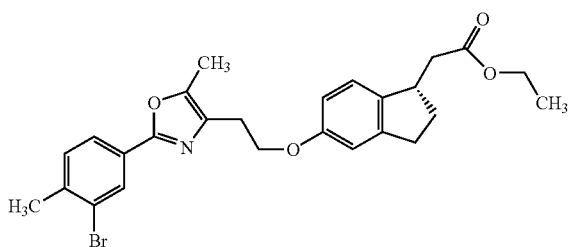

A suspension of ethyl [(1S)-5-hydroxy-2,3-dihydro-1H-inden-1-yl]acetate (0.60 g, 2.72 mmol), Example 82 (0.81 g, 2.72 mmol), ADDP (1.03 g, 4.09 mmol), and $Ph_3P$ (1.07 g, 4.09 mol) in 10 mL anhydrous dichloromethane was stirred at rt under argon for 16 h. After solids were removed by filtration, dichloromethane was removed under reduced pressure. The residue was purified by Biotage to obtain ethyl ((1S)5-{2-[2-(3-bromo-4-methylphenyl)-5-methyl-1,3-oxazol4-yl]ethoxy}-2,3-dihydro-1 H-inden-1-yl)acetate (1.35 g, 99%). $^1$H NMR ($CDCl_3$-$d_2$) δ 8.15(s, 1H), 7.80 (d, 1H), 7.27 (d, 1H), 7.04 (d, 1H), 6.77 (s, 1H), 6.70 (d, 1H), 4.13-4.23 (m, 4H), 3.51 (qr, 1H), 2.96 (t, 2H), 2.67-2.89 (m, 3H), 2.43(s, 3H), 2.33-2.40 (m, 5H), 1.70-1.77 (m, 1H), 1.30 (m, 3H). EI-LCMS(rel abundance), m/z 500 (M+H, 100%).

EXAMPLE 84

Preparation of ethyl [(1S)-5-(2-{2-[3-(benzylamino)-4-methylphenyl]-5-methvl-1,3-oxazol-4-yl}ethoxy)-2,3-dihydro-1H-inden-1-yl]acetate

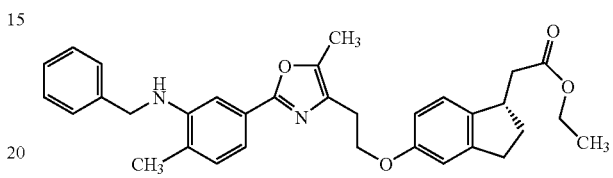

A dried flask was charged with palladium acetate (25.2 mg, 0.11 mmol, 5 mol %), BINAP (104.9 mg, 0.17 mmol, 7.5 mol %), and cesium carbonate (1.46 g, 4.49 mmol). To this mixture was added a solution of ethyl ((1S)-5-{2-[2-(3-bromo-4-methylphenyl)-5-methyl-1,3-oxazol-4-yl]ethoxy}-2,3-dihydro-1H-inden-1-yl)acetate (1.12 g, 2.25 mmol) and benzyl amine (0.48 g, 4.49 mmol) in toluene (50 mL) using an addition funnel. The first 15 mL was added quickly (5 minutes) and the remainder added over a period of 1 h. The mixture warmed to 85° C. after the first 30% portion was added. The reaction mixture was stirred at 85° C. for 16 h. The crude was cooled to rt, diluted with ethyl acetate, and then filtered through a Celite® plug. The filtrate was then concentrated under reduced pressure and the residue purified by silica gel flash chromatography (10-20% ethyl acetate in hexanes) to afford 1.1 g (93.3% yield) of desired product. $^1$H NMR (300 MHz/$CDCl_3$) δ 7.28-7.44 (m, 7H), 7.12 (d, 1H), 7.03 (d, 1H), 6.77 (s, 1H), 6.71 (d, 1H), 4.44 (s, 2H), 4.13-4.22 (m, 4H), 3.82 (br, 1H), 3.51 (qr, 1H), 2.96 (t, 2H), 2.77-2.92 (m, 2H), 2.71 (dd, 1H), 2.31-2.43 (m, 5H), 2.17 (s, 3H), 1.61-1.79 (m, 1H), 1.26 (t, 3H). EI-LCMS(rel abundance), m/z 525.4 (MH+, 100%).

EXAMPLE 85

Preparation ethyl ((1S)-5-{2-[2-3-amino-4-methylphenyl)-5-methyl-1,3-oxazol-4-yl]ethoxy}-2,3-dihydro-1H-inden-1-yl)acetate

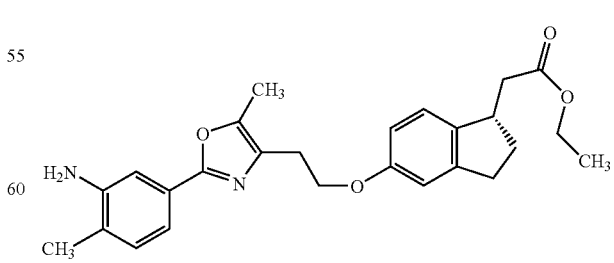

Ethyl [(1S)-5-(2-{2-[3-(benzylamino)-4-methylphenyl]-5-methyl-1,3-oxazol-4-yl}ethoxy)-2,3-dihydro-1H-inden-1-yl]acetate (Example 84, 0.5 g, 0.95 mmol) was dissolved in a mixture of methanol (5 mL) and ethyl acetate (5 mL). Then, Pd(OH)₂ (334 mg, 20% wt. on carbon, wet) and NH₄HCO₂ (601 mg, 9.53 mmol) was added and the mixture was heated to reflux. After 2 h, the reaction mixture was cooled to rt, filtered through a plug of Celite®. The filtrate was concentrated under reduced pressure and the residue was purified by flash chromatography (10% to 20% ethyl acetate in hexanes) to afford 410 mg (99% yield) of the desired product. ¹H NMR (300 MHz/CD₂Cl₂) δ 7.38 (s, 1H), 7.31 (d, 1H), 7.15 (d, 1H), 7.04 (d, 1H), 6.77 (s, 1H), 6.67 (d, 1H), 5.33 (s, 2H), 5.03 (br, 2H), 4.11-4.22 (m, 4H), 3.48 (qr, 1H), 2.77-2.88 (m, 2H), 2.68 (dd, 1H), 2.29-2.42 (m, 5H), 2.21 (s, 3H), 1.66-1.79 (m, 1H), 1.26 (t, 3H). EI-LCMS(rel abundance), m/z 435.4 (MH+, 100%).

EXAMPLE 86

Preparation of ethyl [(1)-5-(2-{2-[3-(dimethylamino)-4-methylphenyl]-5-methyl-1,3-oxazol-4-yl}ethoxy)-2,3-dihydro-1H-inden-1-yl]acetate

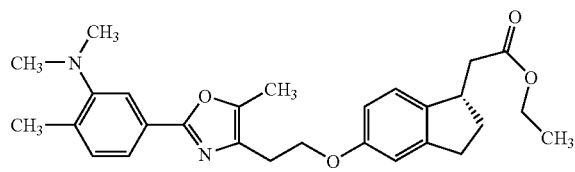

To a solution of ethyl ((1 S)-5-{2-[2-(3-amino-4-methylphenyl)-5-methyl-1,3-oxazol-4-yl]ethoxy}-2,3-dihydro-1H-inden-1-yl)acetate (250 mg, 0.58 mmol) in DMF (2 mL) at rt was added cesium carbonate (562.4 mg, 1.73 mmol). The reaction mixture was stirred for 30 minutes followed by addition of methyl iodide (163.3 mg, 1.15 mmol). The reaction mixture was stirred at rt for 68 h, diluted with ethyl acetate (100 mL), and the solid was filtered off. The combined organic layer was washed with water and brine. The organic layer was dried over Na₂SO₄, filtered and concentrated under reduced pressure. The crude was redissolved in methanol and filtered through a C₈-Silica plug before preparative HPLC purification with 30-100% acetonitrile in water to obtain 178 mg (67% yield) of the desired dimethylated product and 40 mg (15.5% yield) of the monomethylation product. ¹H NMR (300 MHz/CDCl₃) δ 7.72 (s, 1H), 7.61 (d, 1H), 7.25 (d, 1H), 7.03 (d, 1H), 6.77 (s, 1H), 6.68 (d, 1H), 4.09-4.22 (m, 4H), 2.42-3.53 (qr, 1H), 2.93 (t, 2H), 2.71-2.90 (m, 8 H), 2.67 (dd, 1H), 2.28-2.47 (m, 8 H), 1.66-1.80 (m, 1H), 1.25 (t, 3H). EI-LCMS(rel abundance), m/z 463.4 (MH+, 100%).

EXAMPLE 87

Preparation of ethyl [(1S)-5-(2-{5-methyl-2-[4-methyl-3-(methylamino)phenyl]-1,3-oxazol-4-yl}ethoxy)-2,3-dihydro-1H-inden-1-yl]acetate

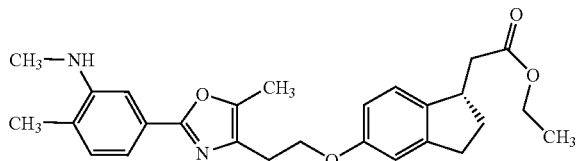

This compound was the second product isolated from the reaction described for Example 86. ¹H NMR (300 MHz/CDCl₃) δ 7.32 (d, 1H), 7.31 (s, 1H), 7.15 (d, 1H), 7.03 (d, 1H), 6.77 (s, 1H), 6.68 (d, 1H), 4.22 (t, 2H), 4.13 (q, 2H), 3.47 (qr, 1H), 3.06 (t, 2H), 2.96 (s, 3H), 2.79-2.88 (m, 2H), 2.67 (dd, 1H), 2.41 (s, 3H), 2.28-2.40 (m, 2H), 2.19 (s, 3H), 1.65-1.78 (m, 1H), 1.25 (t, 3H). EI-LCMS(rel abundance), m/z 449.4 (MH+, 100%).

EXAMPLE 88

Preparation of ethyl [(1S)-5-(2-{2-[3-(acetylamino)phenyl]-5-methyl-1,3-oxazol-4-yl}ethoxy)-2,3-dihydro-1H-inden-1-yl]acetate

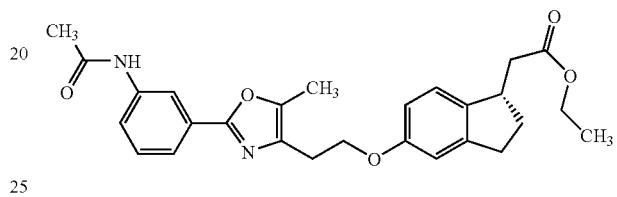

To a solution of DMAP (1.0 mg) and acetyl chloride (9.3 mg, 0.12 mmol) in 1 mL dichloromethane was added a solution of ethyl ((1S)-5-{2-[2-(3-aminophenyl)-5-methyl-1,3-oxazol-4-yl]ethoxy}-2,3-dihydro-1H-inden-1-yl)acetate (25 mg, 0.06 mmol) in dichloromethane (1 mL). Then, triethylamine (0.5 mL) was added and the reaction mixture was stirred for 16 h. The reaction mixture was concentrated under reduced pressure and redissolved in acetonitrile/methanol. The solution was filtered through a C₈-Silica plug before preparative HPLC purification using 10 to 80% acetonitrile in water gradient to afford 15.3 mg (55.6%) of the desired product. ¹H NMR (300 MHz/CDCl₃) δ 7.97 (s, 1H), 7.70 (d, 2H), 7.49 (s, 1H), 7.37 (t, 1H), 7.03 (d, 1H), 6.76 (s, 1H), 6.69 (d, 1H), 4.11-4.22 (m, 4H), 3.48 (qr, 1H), 2.92 (t, 2H), 2.72-2.88 (m, 2H), 2.68 (dd, 1H), 2.27-2.40 (m, 5H), 2.16 (s, 3H), 1.64-1.76 (m, 1H), 1.24 (t, 3H). EI-LCMS(rel abundance), m/z 463.4 (MH+, 100%).

EXAMPLE 89

Preparation of ethyl {(1S)-5-[2-(2-{3-[bis(methylsulfonyl)amino]phenyl}-5-methyl-1,3-oxazol-4-yl)ethoxy]-2,3-dihydro-1H-inden-1-yl}acetate

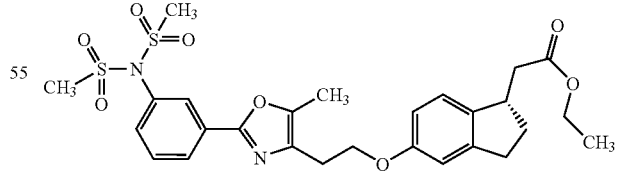

This compound was prepared using the same procedure as Example 88. ¹H NMR (300 MHz/CDCl₃) δ 8.09 (d, 1H), 7.97 (s, 1H), 7.53 (t, 1H), 7.38 (d, 1H), 7.05 (d, 1H), 6.77 (s, 1H), 6.70 (d, 1H), 4.13-4.22 (m, 4H), 3.51 (qr, 1H), 3.45 (s, 6 H), 2.97 (t, 2H), 2.79-2.88 (m, 2H), 2.69 (dd, 1H), 2.33-2.43 (m, 5H), 1.67-1.79 (m, 1H), 1.27 (t, 3H). EI-LCMS(rel abundance), m/z 577.3 (MH+, 100%).

EXAMPLE 90

Preparation of ethyl {(1S)-5-[2-(2-{3-[acetyl(methyl)amino]phenyl}-5-methyl-1,3-oxazol-4-yl)ethoxy]-2,3-dihydro-1H-inden-1-yl}acetate

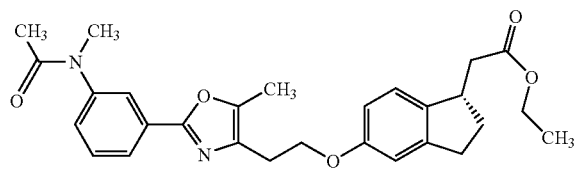

This compound was prepared using the same procedure as Example 88 using the appropriate amide as starting material. $^1$H NMR (300 MHz/CDCl$_3$) δ 7.96 (d, 1H), 7.83 (s, 1H), 7.51 (t, 1H), 7.25 (d, 1H), 7.04 (d, 1H), 6.76 (s, 1H), 6.69 (d, 1H), 4.13-4.23 (m, 4H), 3.51 (qr, 1H), 3.31 (s, 3H), 3.00 (t, 2H), 2.77-2.89 (m, 2H), 2.69 (dd, 1H), 2.42 (s, 3H), 2.32-2.41 (m, 2H), 1.94 (s, 3H), 1.65-1.78 (m, 1H), 1.27 (t, 3H). EI-LCMS (rel abundance), m/z 477.5 (MH+, 100%).

EXAMPLE 91

Preparation of [(1S)-5-(2-{2-[3-(dimethylamino)-4-methylphenyl]-5-methyl-1,3-oxazol-4-yl}ethoxy)-2,3-dihydro-1H-inden-1-yl]acetic acid

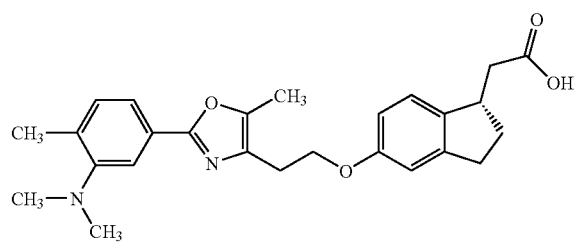

To a solution of ethyl [(1S)-5-(2-{2-[3-(dimethylamino)-4-methylphenyl]-5-methyl-1,3-oxazol-4-yl}ethoxy)-2,3-dihydro-1H-inden-1-yl]acetate (175.0 mg, 0.38 mmol) in ethanol (1 mL) and THF (1 mL) was added LiOH (159 mg) followed by addition of 1 mL water. The reaction mixture was then stirred at rt for 4 h. The reaction mixture was then acidified to pH 5-6 and the solvent was removed by reduced pressure. The residue was redissolved in methanol, filtered through a plug of C$_8$-Silica plug before preparative HPLC purification using 10 to 70% acetonitrile in water to afford desired product 156 mg (95% yield). $^1$H NMR (300 MHz/CD$_2$Cl$_2$) δ 7.96 (s, 1H), 7.80 (d, 1H), 7.35 (d, 1H), 7.06 (d, 1H), 6.77 (s, 1H), 6.67 (d, 1H), 4.21 (t, 2H), 3.47 (qr, 1H), 3.11 (s, 6H), 2.97 (t, 2H), 2.75-2.90 (m, 2H), 2.70 (dd, 1H), 2.54 (s, 3H), 2.29-2.46 (m, 5H), 1.65-1.78 (m, 1H). EI-LCMS (rel abundance), m/z 435.4 (MH+, 100%). HPLC RT: 3.52 min.

Examples 92 through Examples 100 were made using the procedure for Example 91.

EXAMPLE 92

[(1S)-5-(2-{5-Methyl-2-[4-methyl-3-(methylamino)phenyl]-1,3-oxazol-4-yl}ethoxy)-2,3-dihydro-1H-inden-1-yl]acetic acid

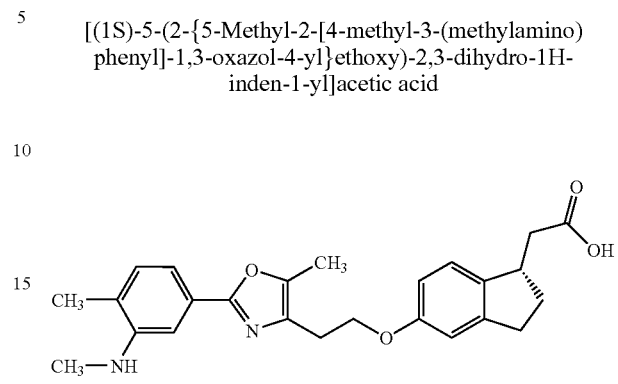

$^1$H NMR (300 MHz/CD$_2$Cl$_2$) δ 8.17 (d, 1H), 7.25 (d, 1H), 7.22 (s, 1H), 7.06-7.11 (m, 2H), 6.79 (s, 1H), 6.70 (d, 1H), 4.20 (t, 2H), 3.49 (qr, 1H), 2.96 (t, 2H), 2.95 (s, 3H), 2.70-2.89 (m, 3H), 2.32-2.49 (m, 5H), 2.16 (s, 3H), 1.68-1.82 (m, 1H). LC-MS [M+H]+ 421.4, RT 3.45 min.

EXAMPLE 93

[(1S)-5-(2-{2-[3-(Acetylamino)phenyl]-5-methyl-1,3-oxazol-4-yl}ethoxy)-2,3-dihydro-1H-inden-1-yl]acetic acid

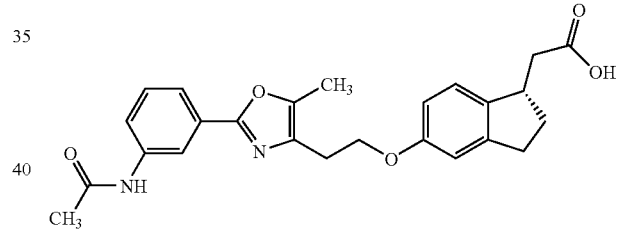

$^1$H NMR (300 MHz/CD$_3$OD) δ 8.18 (s, 1H), 7.68 (d, 1H), 7.63 (d, 1H), 7.41 (t, 1H), 7.06 (d, 1H), 6.77 (s, 1H), 6.79 (d, 1H), 7.88 (t, 1H), 4.20 (t, 2H), 3.43 (qr, 1H), 2.94 (t, 2H), 2.72-2.86 (m, 2H), 2.66 (dd, 1H), 2.36 (s, 3H), 2.25-2.37 (m, 2H), 2.14 (s, 3H), 1.67-174 (m, 1H).

EXAMPLE 94

{(1S)-5-[2-(5-Methyl-2-{3-[(methylsulfonyl)amino]phenyl}-1,3-oxazol-4-yl)ethoxy]-2,3-dihydro-1H-inden-1-yl}acetic acid

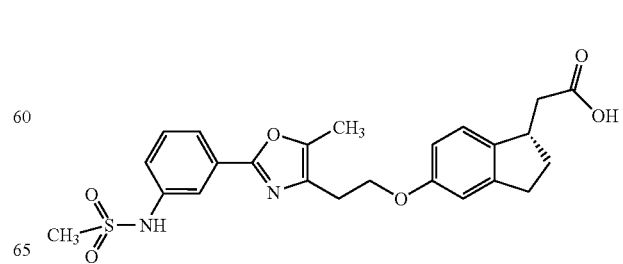

¹H NMR (300 MHz/CD₃OD) δ 7.83 (t, 1H), 7.72 (d, 1H), 7.44 (t, 1H), 7.33 (d, 1H), 7.06 (d, 1H), 6.76 (s, 1H), 6.68 (d, 1H), 4.20 (t, 2H), 3.42 (qr, 1H), 3.00 (s, 3H), 2.95 (t, 2H), 2.73-2.90 (m, 2H), 2.66 (dd, 1H), 2.37 (s, 3H), 2.27-2.36 (m, 2H), 1.63-176 (m, 1H).

EXAMPLE 95

{(1S)-5-[2-(2-{3-[Acetyl(methyl)amino]phenyl}-5-methyl-1,3-oxazol-4-yl)ethoxy]-2,3-dihydro-1H-inden-1-yl}acetic acid

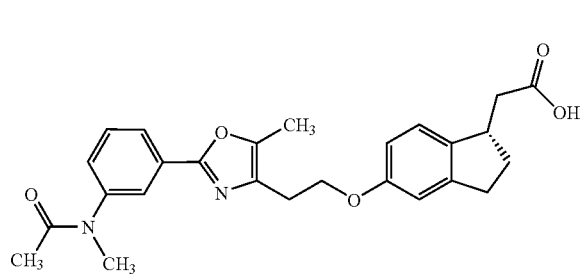

¹H NMR (300 MHz/CD₃OD) δ 7.96 (d, 1H), 7.87 (s, 1H), 7.58 (t, 1H), 7.39 (d, 1H), 7.05 (d, 1H), 6.75 (s, 1H), 6.66 (d, 1H), 4.20 (t, 2H), 3.42 (qr, 1H), 3.27 (s, 3H), 2.95 (t, 2H), 2.72-2.85 (m, 2H), 2.65 (dd, 1H), 2.37 (s, 3H), 2.24-2.36 (m, 2H), 1.88 (s, 3H), 1.64-175 (m, 1H).

EXAMPLE 96

{(1S)-5-[2-(5-Methyl-2-{3-[methyl(methylsulfonyl)amino]phenyl}-1,3-oxazol-4-yl)ethoxy]-2,3-dihydro-1H-inden-1-yl}acetic acid

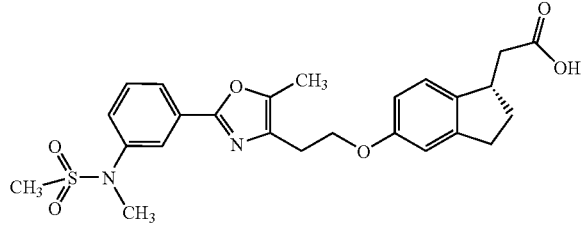

¹H NMR (300 MHz/CD₃OD) δ 8.01 (s, 1H), 7.87-7.91 (m, 1H), 7.51-7.54 (m, 2H), 7.06 (d, 1H), 6.77 (s, 1H), 6.69 (d, 1H), 4.21 (t, 2H), 3.41 (qr, 1H), 3.36 (s, 3H), 2.96 (t, 2H), 2.93 (s, 3H), 2.72-2.87 (m, 2H), 2.67 (dd, 1H), 2.38 (s, 3H), 2.28-2.36 (m, 2H), 1.63-176 (m, 1H).

EXAMPLE 97

[(1S)-5-(2-{2-[4-(Dimethylamino)phenyl]-5-methyl-1,3-oxazol-4-yl}ethoxy)-2,3-dihydro-1H-inden-1-yl]acetic acid

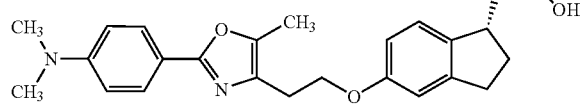

¹H NMR (CD₃)₂CO) δ 1.7 (m, 1H), 2.3 (m, 5H), 2.8 (m, 5H), 3.1 (s, 6H), 3.5 (m, 1H), 4.3 (t, 2H), 6.8 (m, 4H), 7.1 (d, 1H), 7.8 (d, 2H).

EXAMPLE 98

[(1S)-5-(2-{2-[4-(Ethylamino)-2-methylphenyl]-5-methyl-1,3-oxazol-4-yl}ethoxy)-2,3-dihydro-1H-inden-1-yl]acetic acid

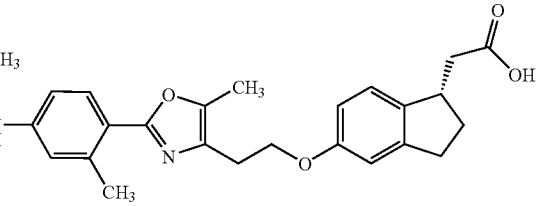

¹H NMR (CD₂Cl₂) δ 1.3 (t, 3H), 1.7 (m, 1H), 2.1 (s, 3H), 2.5 (m, 5H), 2.8 (m, 3H), 3.1 (t, 2H), 3.3 (q, 2H), 3.5.(t, 1H), 4.2 (t, 2H), 6.7 (m, 3H), 7.1 (d, 1H), 7.7 (s, 1H), 7.9 (d, 1H).

EXAMPLE 99

[(1S)-5-(2-{2-[4-(diethylamino)-2-methylphenyl]-5-methyl-1,3-oxazol-4-yl}ethoxy)-2,3-dihydro-1H-inden-1-yl]acetic acid

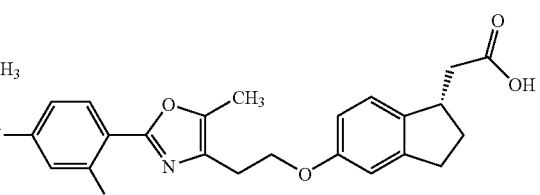

¹H NMR (CD₂Cl₂) δ 1.2 (t, 6H), 1.7 (m, 1H), 2.4 (m, 5H), 2.8 (m, 6H), 3.1 (t, 2H), 3.5 (m, 5H), 4.2 (t, 2H), 6.7 (m, 1H), 6.8 (s, 1H), 6.9 (m, 2H), 7.1 (d, 1H), 8.0 (d, 1H).

EXAMPLE 100

[(1S)-5-(2-{2-[4-(dimethylamino)-3-methylphenyl]-5-methyl-1,3-oxazol-4-yl}ethoxy)-2,3-dihydro-1H-inden-1-yl]acetic acid

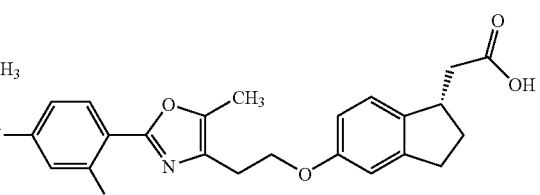

¹H NMR (CD₂Cl₂) δ 1.7 (m, 1H), 2.4 (m, 5H), 2.6 (s, 3H), 2.8 (m, 3H), 3.1 (i, 2H), 3.3 (s, 6H), 3.5 (m, 1H), 4.2 (t, 2H), 6.7 (m, 1H),6.8 (s, 1H), 7.1 (d, 1H), 7.5 (d, 1H), 8.0 (m, 2H).

EXAMPLE 101

Preparation of ethyl [(1S)-5-(2-{5-methyl-2-[4-(4-morpholinyl)phenyl]-1,3-oxazol-4-yl}ethoxy)-2,3-dihydro-1H-inden-1-yl]acetate

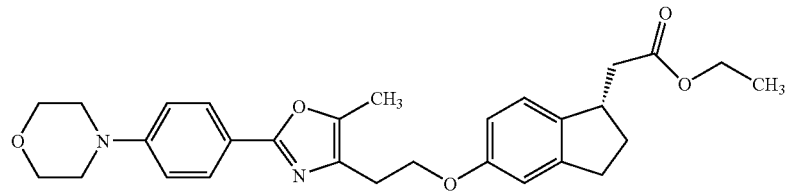

To a vacuum dried flask charged with argon were added ethyl ((1 S)-5-{2-[2-(4-bromophenyl)-5-methyl-1,3-oxazol-4-yl]ethoxy}-2,3-dihydro-1H-inden-1-yl )acetate (0.1 g, 0.2 mmol), sodium t-butoxide (0.03 g, 0.3 mmol), 1,1'-biphenyl-2-yl[di(tert-butyl)]phosphine (0.012 g, 0.04 mmol), morpholine (0.022 g, 0.25 mmol), Pd$_2$(dba)$_3$ (0.019 g, 0.02 mmol), and toluene (1 mL). The reaction was degassed by bubbling argon through the flask for 15 minutes. The reaction was stirred at 80° C. for 16 h, then was cooled to rt and filtered through a silica gel plug. The filtrate was evaporated under vacuum and the residue was purified by HPLC to obtain ethyl [(1S)-5-(2-{5-methyl-2-[4-(4-morpholinyl)phenyl]-1,3-oxazol-4-yl}ethoxy)-2,3-dihydro-1H-inden-1-yl]acetate (0.06 g, 0.1 mmol) in 60% yield. $^1$H NMR ( CDCl$_3$) δ 1.3 (m, 3H), 1.7 (m, 1H), 2.4 (m, 5H), 2.8 (m, 3H), 3.0 (m, 2H), 3.3 (m, 4H), 3.5 (m, 1H), 3.9 (m, 4H), 4.2 (m, 4H), 6.7 (m, 2H), 6.9 (d, 2H), 7.1 (d, 1H), 7.9 (m, 2H); MS (ES) 491 (M+1)$^+$.

EXAMPLE 102

Preparation of [(1S)-5-(2-{5-methyl-2-[4-(4-morpholinyl)phenyl]-1,3-oxazol-4-yl}ethoxy)-2,3-dihydro-1H-inden-1-yl]acetic acid

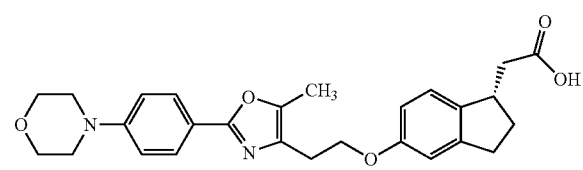

Ethyl [(1S)-5-(2-{5-methyl-2-[4-(4-morpholinyl)phenyl]-1,3-oxazol-4-yl}ethoxy)-2,3-dihydro-1H-inden-1-yl]acetate (0.058 g, 0.12 mmol) was dissolved in EtOH (1 mL), and LiOH.H$_2$O (0.025 g, 0.6 mmol) was added. Water (1 mL) was added, followed by THF was added until the cloudy solution became clear. The resulting mixture was stirred overnight at rt. HCl (2 N) was added to adjust the pH to 2, and the mixture was extracted three times with ethyl acetate. The combined organic layers were dried, filtered and evaporated. The residue was purified by preparative HPLC to obtain [(1S)-5-(2-{5-methyl-2-[4-(4-morpholinyl)phenyl]-1,3-oxazol-4-yl}ethoxy)-2,3-dihydro-1 H-inden-1-yl]acetic acid (0.038 g, 0.08 mmol) in 70% yield. $^1$H NMR ((CDCl$_3$) δ 1.8 (m, 1H), 2.4 (m, 3H), 3.0 (t, 2H), 3.3 (m, 4H), 3.5 (m, 1H), 3.9 (m, 4H), 4.2 (t, 2H), 6.7 (m, 1H), 6.8 (s, 1H), 6.9 (d, 2H), 7.1 (d, 1H), 7.9 (d, 2H); MS (ES) 463 (M+1)$^+$.

Using the methods described above and the appropriate starting materials, the compounds in Table 1 may be prepared. The corresponding IUPAC names for the compounds in Table 1 may be found on Table 2.

TABLE 1

| Example No. | Structure | HPLC RT (min) | EI-MS [M + H]$^+$ |
|---|---|---|---|
| 103 | (chiral structure with oxazole, methyl, benzyl amine) | 4.16 | 483.4 |

TABLE 1-continued

| Example No. | Structure | HPLC RT (min) | EI-MS [M + H]+ |
|---|---|---|---|
| 104 | 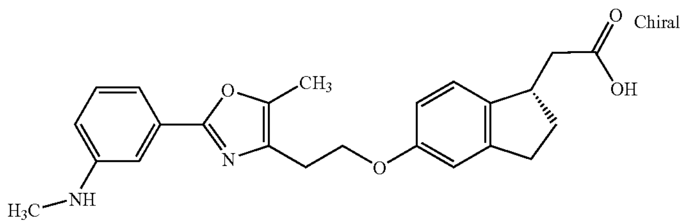 | 3.39 | 407.4 |
| 105 | 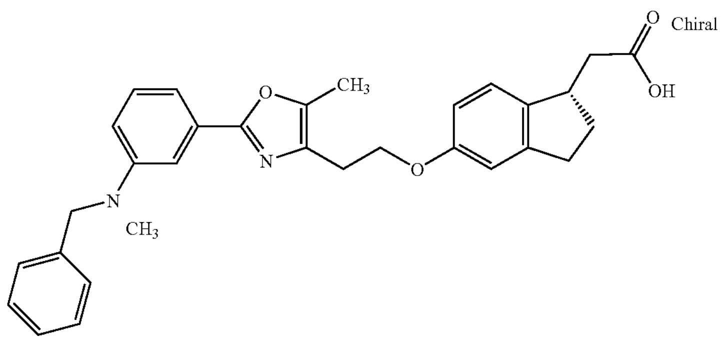 | 4.35 | 497.4 |
| 106 | 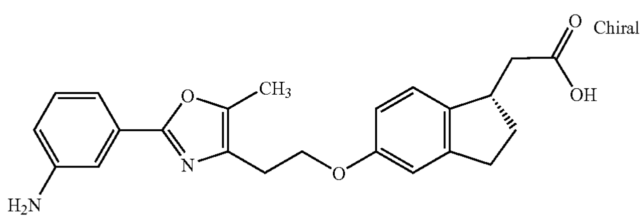 | 3.19 | 393.4 |
| 107 | 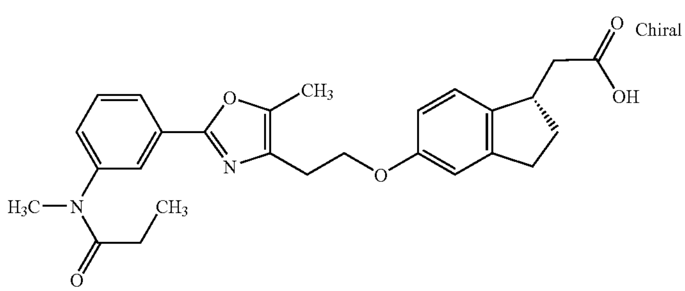 | 3.65 | 463.3 |
| 108 | 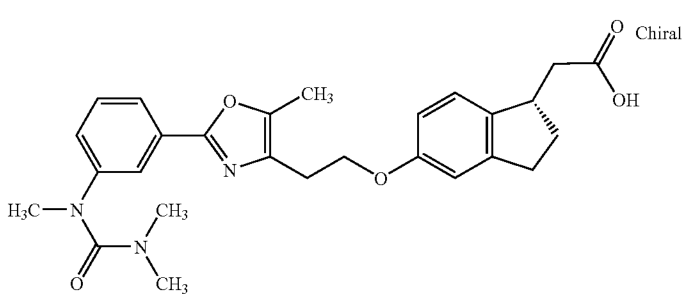 | 3.59 | 478.3 |

TABLE 1-continued

| Example No. | Structure | HPLC RT (min) | EI-MS [M + H]+ |
|---|---|---|---|
| 109 | 3-propionamidophenyl-5-methyloxazole-indane acetic acid derivative (Chiral) | 3.62 | 449.3 |
| 110 | 3-(3,3-dimethylureido)phenyl-5-methyloxazole-indane acetic acid derivative (Chiral) | 3.48 | 464.2 |
| 111 | 3-(ethylsulfonamido)phenyl-5-methyloxazole-indane acetic acid derivative (Chiral) | 3.66 | 485.3 |
| 112 | 3-(isopropylsulfonamido)phenyl-5-methyloxazole-indane acetic acid derivative (Chiral) | 3.77 | 499.3 |
| 113 | 3-(N,N-dimethylsulfamoylamino)phenyl-5-methyloxazole-indane acetic acid derivative (Chiral) | 3.72 | 500.2 |

TABLE 1-continued

| Example No. | Structure | HPLC RT (min) | EI-MS [M + H]+ |
|---|---|---|---|
| 114 | 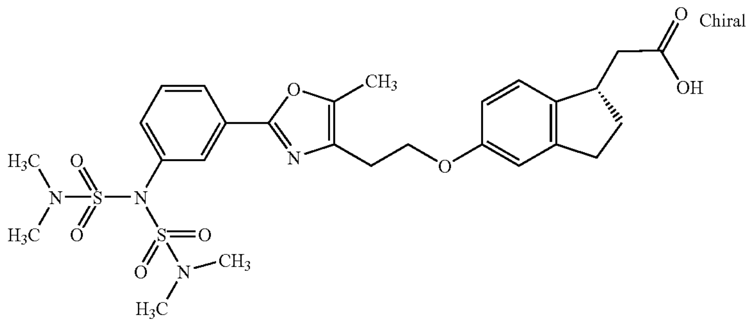 | 3.91 | 607.2 |
| 115 | 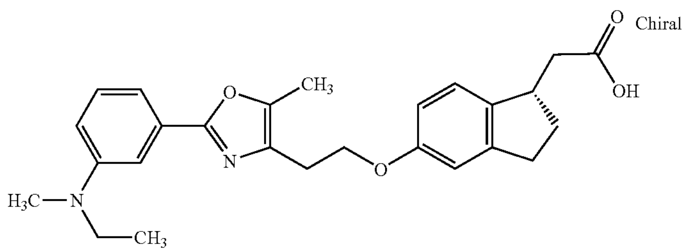 | 3.38 | 435.3 |
| 116 | 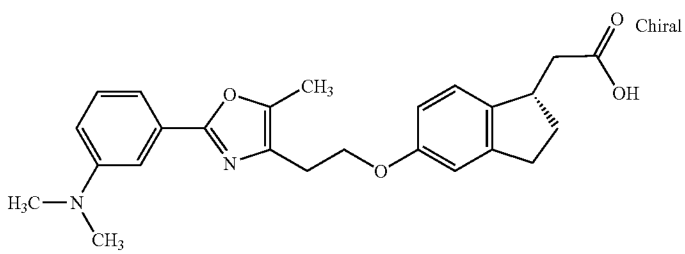 | 3.54 | 421.4 |
| 117 | 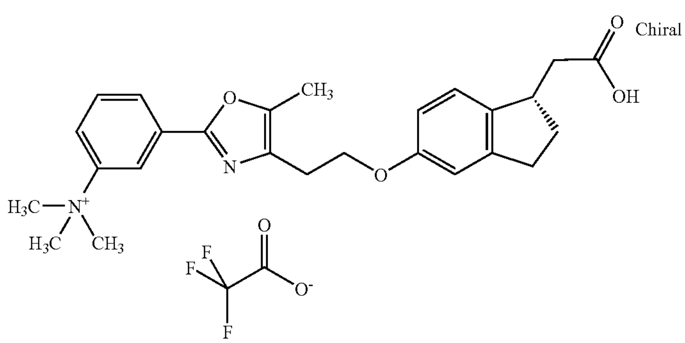 | 2.84 | 435.4 |
| 118 | 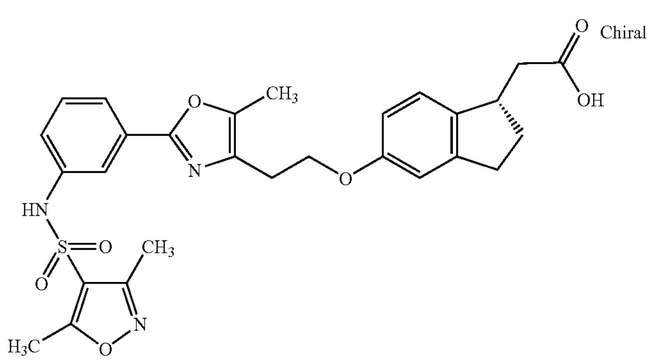 | 3.88 | 552.3 |

TABLE 1-continued

| Example No. | Structure | HPLC RT (min) | EI-MS [M + H]+ |
|---|---|---|---|
| 119 | 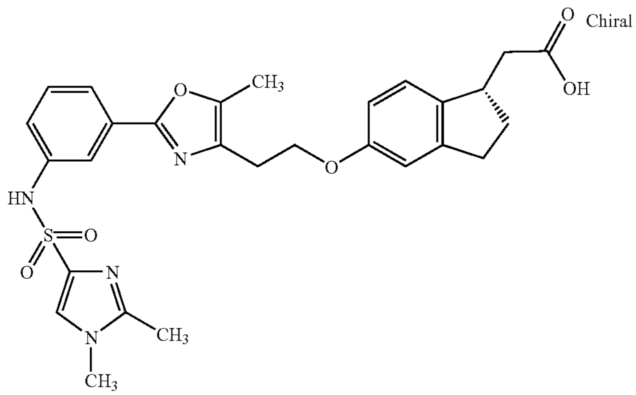 | 3.26 | 551.4 |
| 120 | 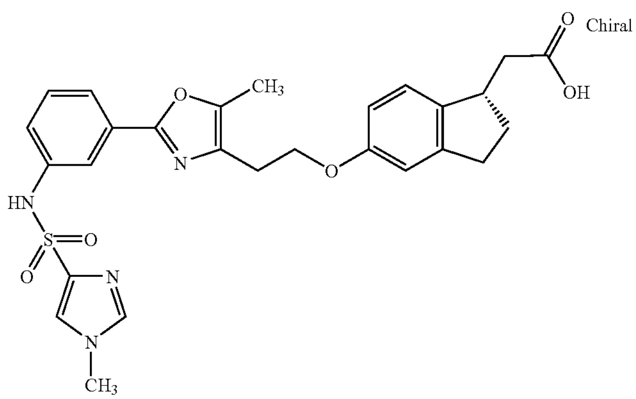 | 3.25 | 537.4 |
| 121 | 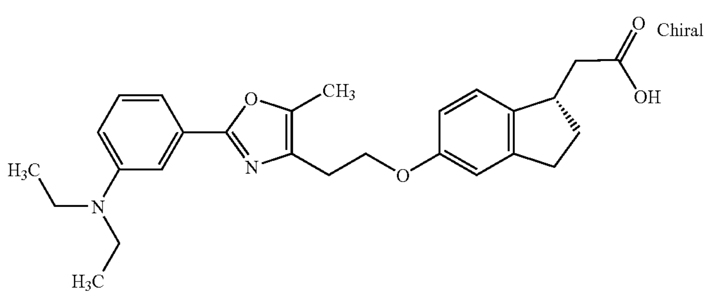 | 3 | 449.4 |
| 122 | 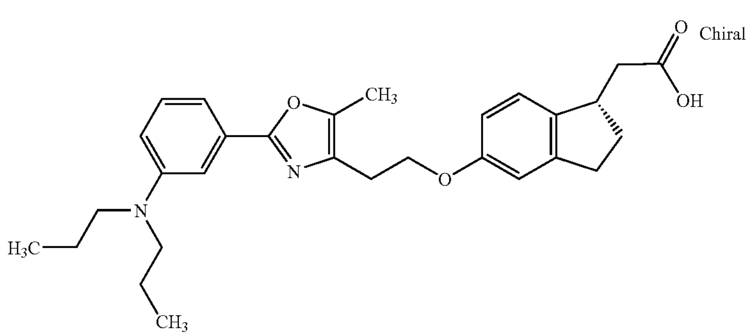 | 3.62 | 477.4 |

TABLE 1-continued

| Example No. | Structure | HPLC RT (min) | EI-MS [M + H]+ |
|---|---|---|---|
| 123 | 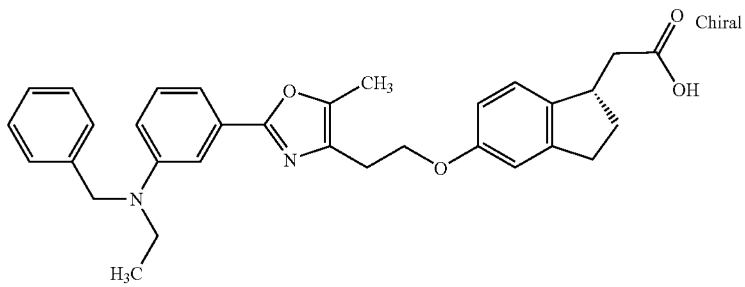 | 4.06 | 511.4 |
| 124 | 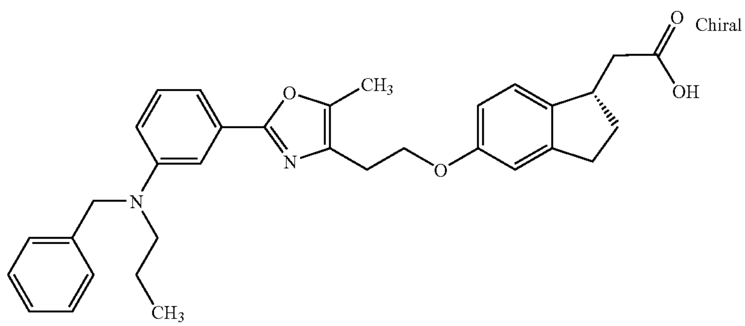 | 4.34 | 525.4 |
| 125 | 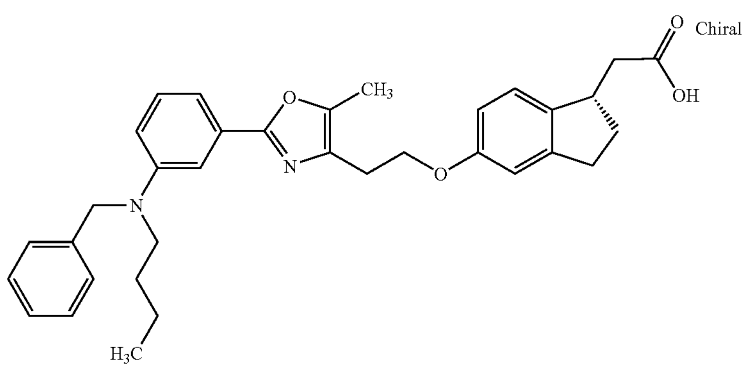 | 4.47 | 539.4 |
| 126 | 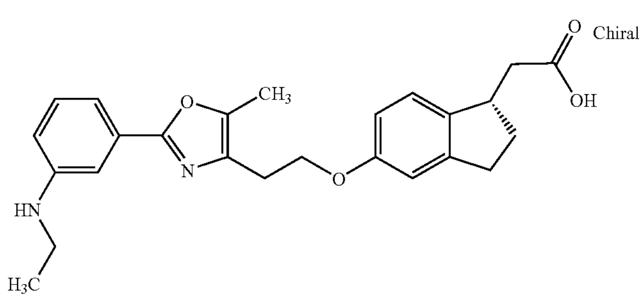 | 3.14 | 421.4 |

TABLE 1-continued
| Example No. | Structure | HPLC RT (min) | EI-MS [M + H]+ |
|---|---|---|---|
| 127 | 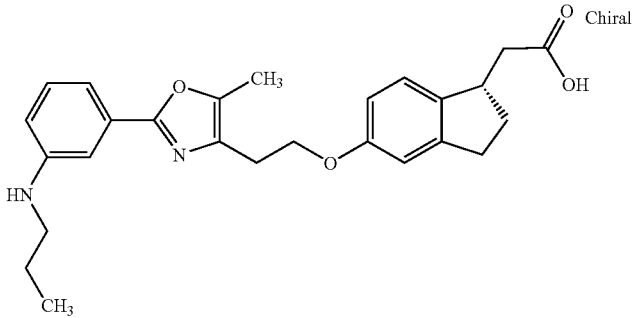 | 3.46 | 435.4 |
| 128 | 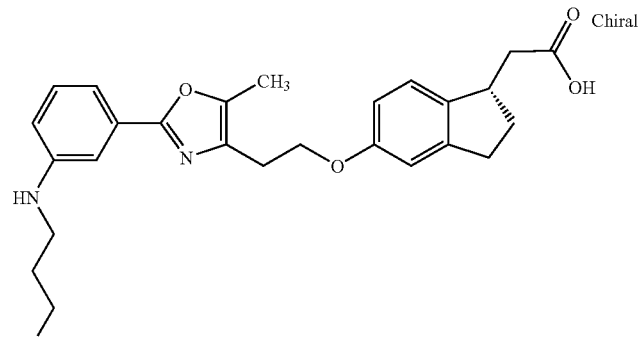 | 3.64 | 449.4 |
| 129 | 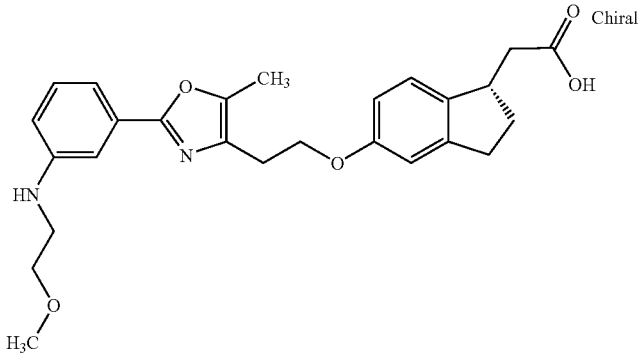 | 3.46 | 451.5 |
| 130 | 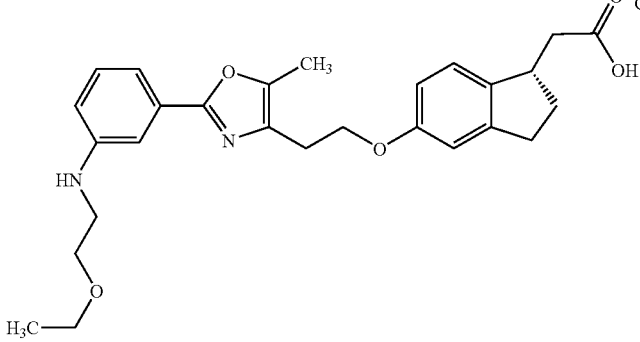 | 3.59 | 465.5 |

TABLE 1-continued
| Example No. | Structure | HPLC RT (min) | EI-MS [M + H]+ |
|---|---|---|---|
| 131 | 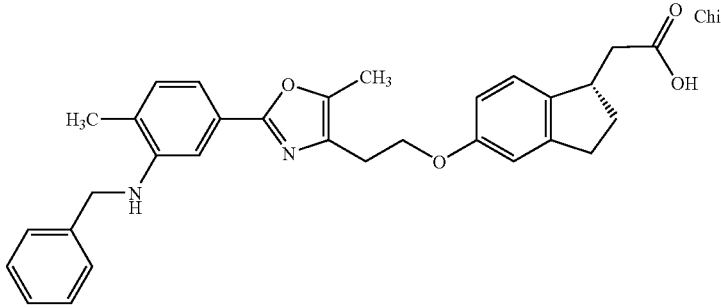 | 4.04 | 497.4 |
| 132 | 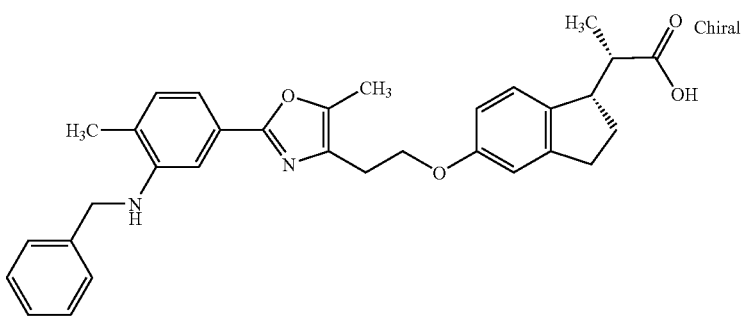 | 4.14 | 511.4 |
| 133 | 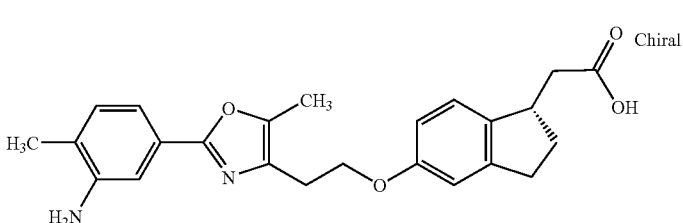 | 3.18 | 407.3 |
| 134 | 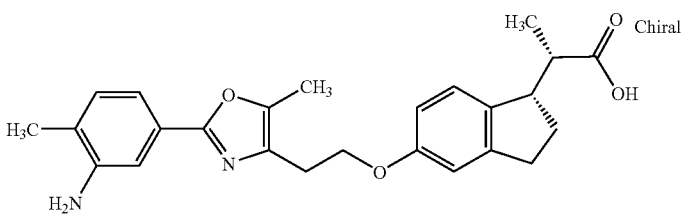 | 3.28 | 421.4 |
| 135 | 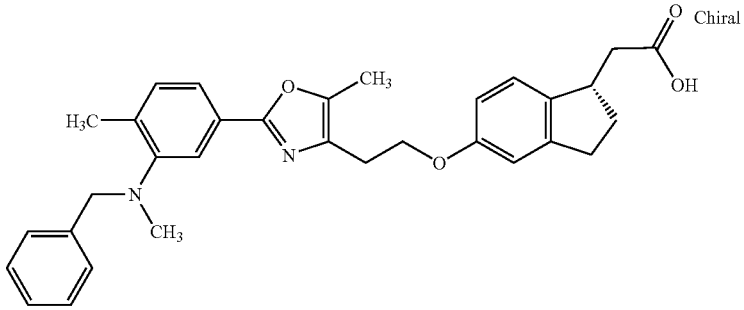 | 3.9 | 511.4 |

TABLE 1-continued

| Example No. | Structure | HPLC RT (min) | EI-MS [M + H]+ |
|---|---|---|---|
| 136 | 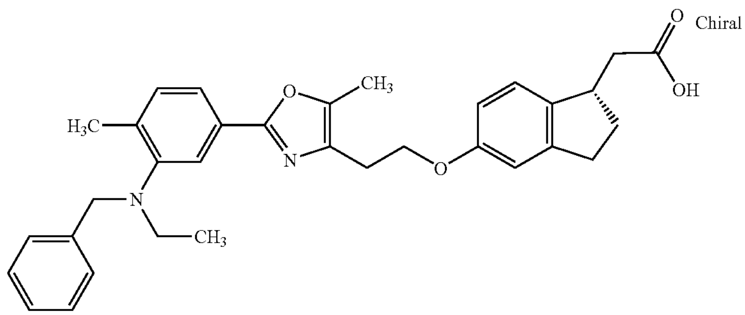 | 3.66 | 525.4 |
| 137 | 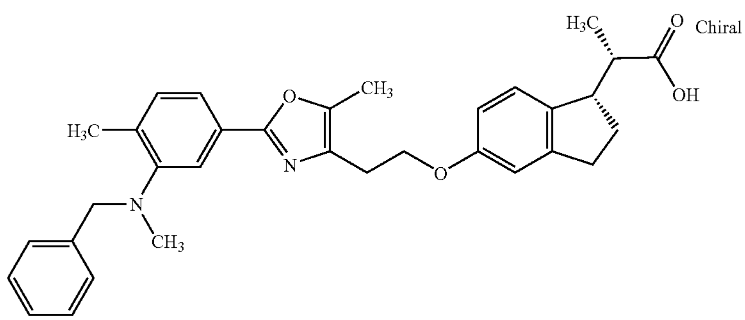 | 4.05 | 525.4 |
| 138 | 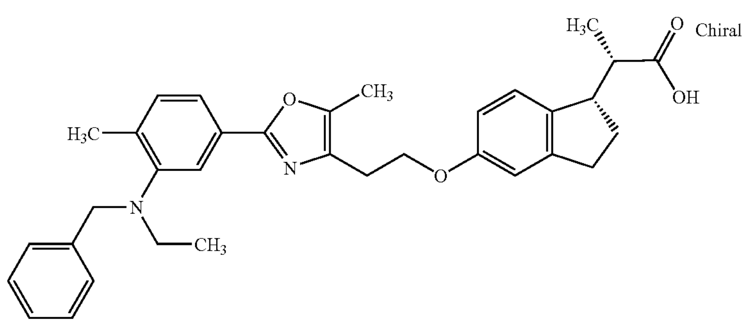 | 3.76 | 539.4 |
| 139 | 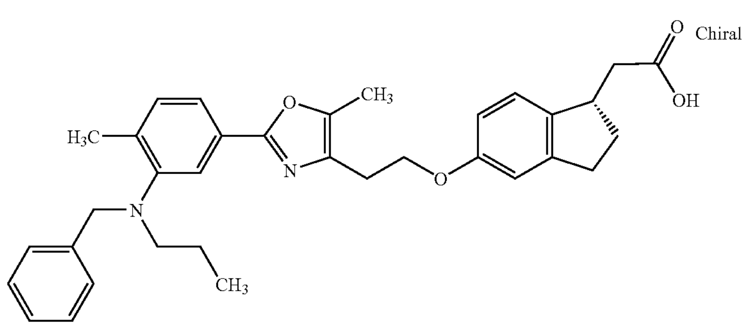 | 3.98 | 539.4 |

TABLE 1-continued

| Example No. | Structure | HPLC RT (min) | EI-MS [M + H]+ |
|---|---|---|---|
| 140 | 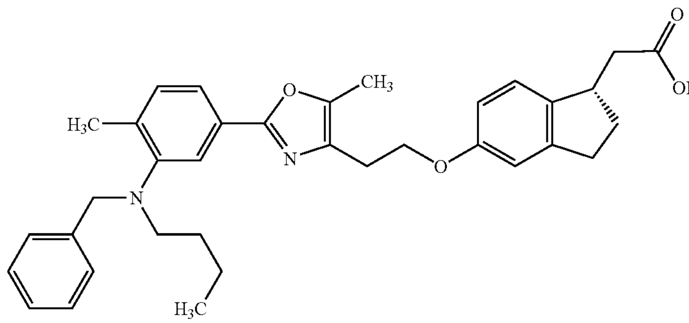 | 4.12 | 553.4 |
| 141 | 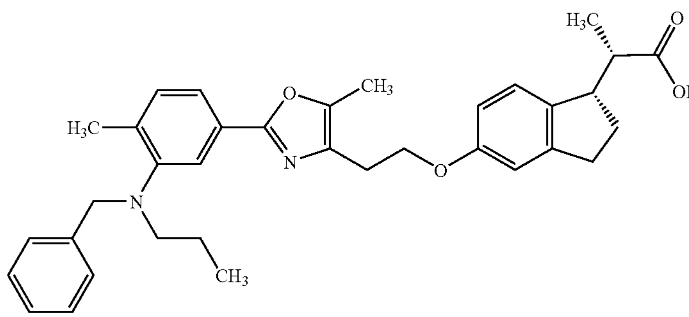 | 4.08 | 553.4 |
| 142 | 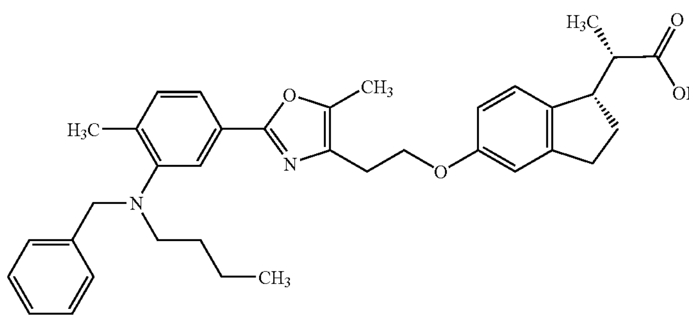 | 4.21 | 567.4 |
| 143 | 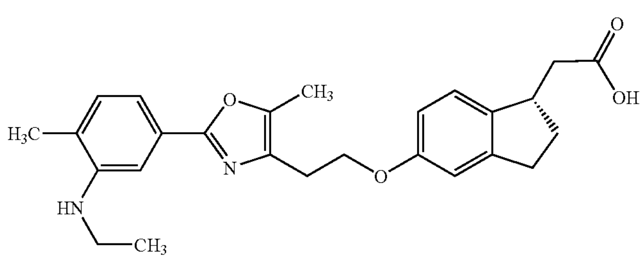 | 3.44 | 435.4 |
| 144 | 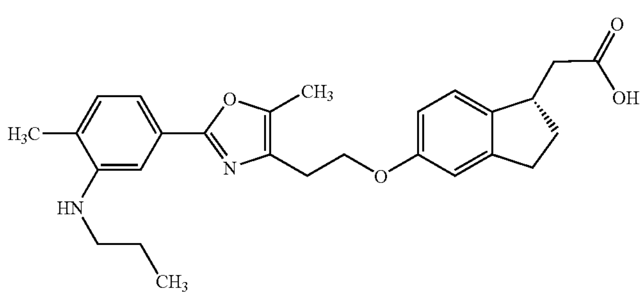 | 3.73 | 449.4 |

TABLE 1-continued

| Example No. | Structure | HPLC RT (min) | EI-MS [M + H]+ |
|---|---|---|---|
| 145 | 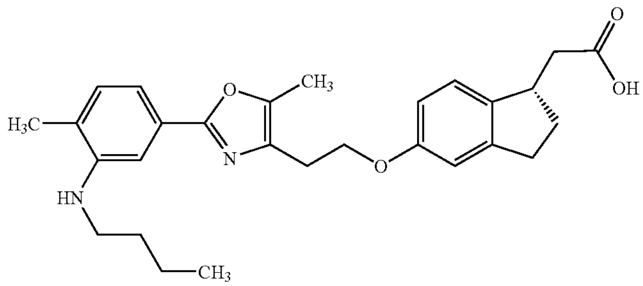 | 3.91 | 463.4 |
| 146 | 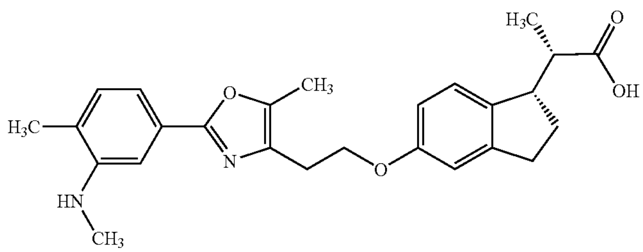 | 3.56 | 435.4 |
| 147 | 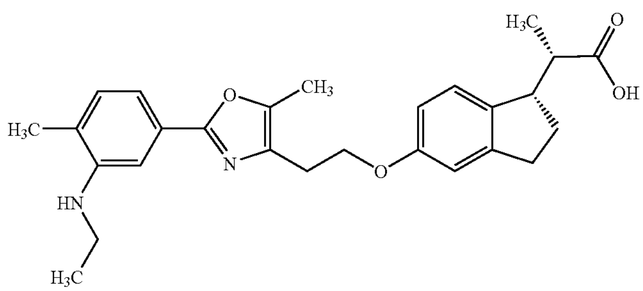 | 3.59 | 449.4 |
| 148 | 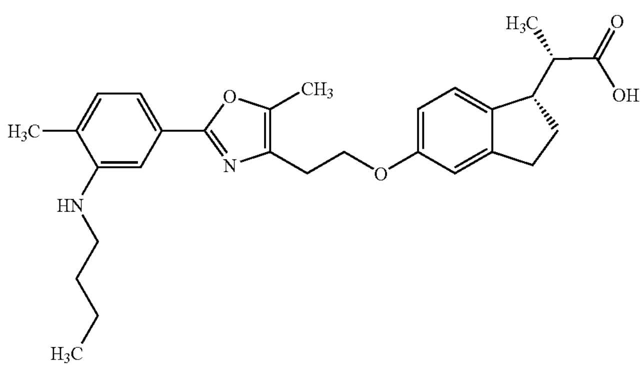 | 4.01 | 477.4 |
| 149 | 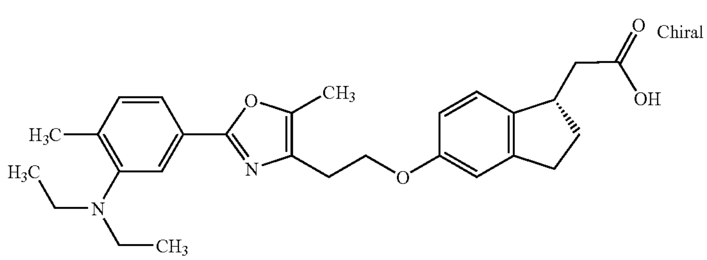 | 2.88 | 463.4 |

TABLE 1-continued

| Example No. | Structure | HPLC RT (min) | EI-MS [M + H]+ |
|---|---|---|---|
| 150 | 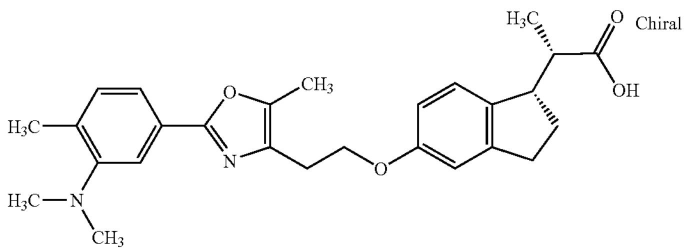 | 3.06 | 449.4 |
| 151 | 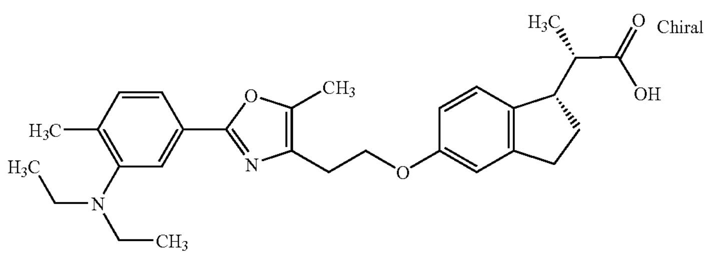 | 2.94 | 477.4 |
| 152 | 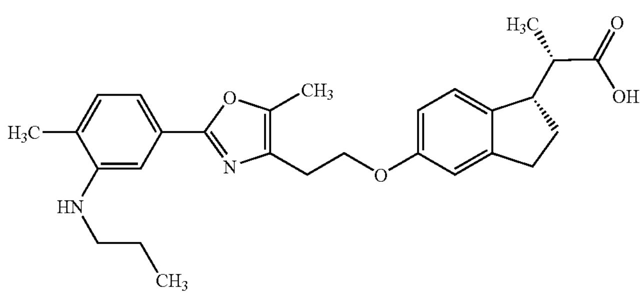 | 3.83 | 463.4 |
| 153 | 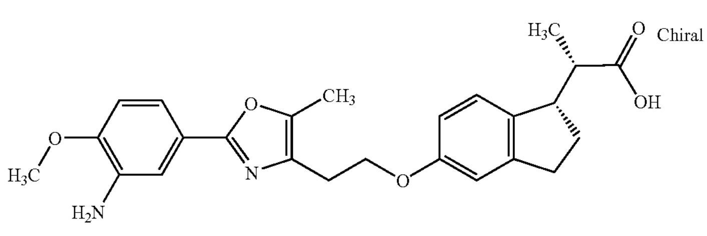 | 3.18 | 437.4 |
| 154 | 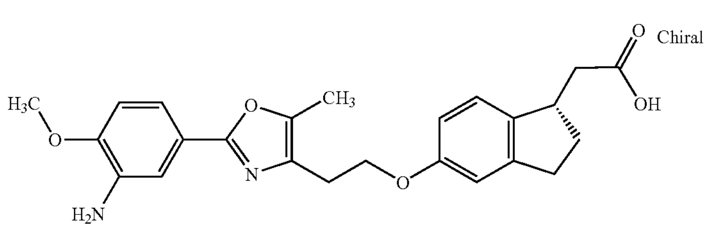 | 3.06 | 423.4 |

TABLE 1-continued

| Example No. | Structure | HPLC RT (min) | EI-MS [M + H]+ |
|---|---|---|---|
| 155 | 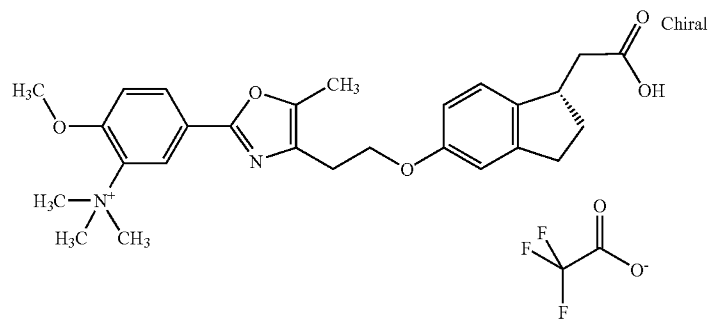 | 2.22 | 465.3 |
| 156 | 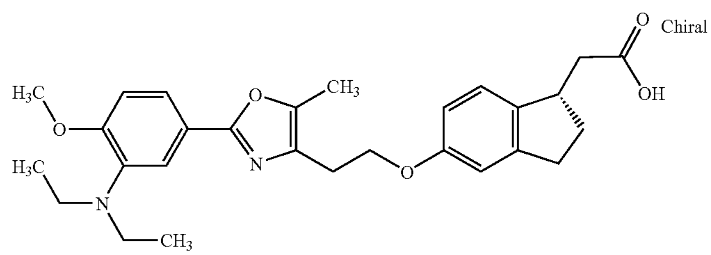 | 2.3 | 479.2 |
| 157 | 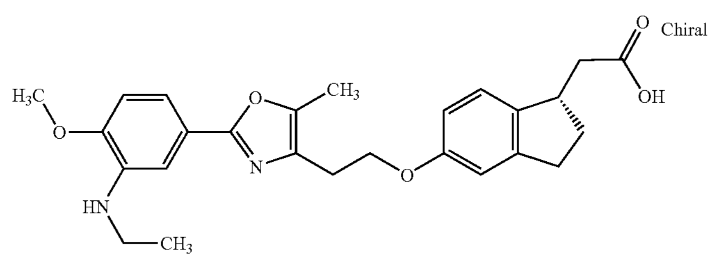 | 2.81 | 451.2 |
| 158 | 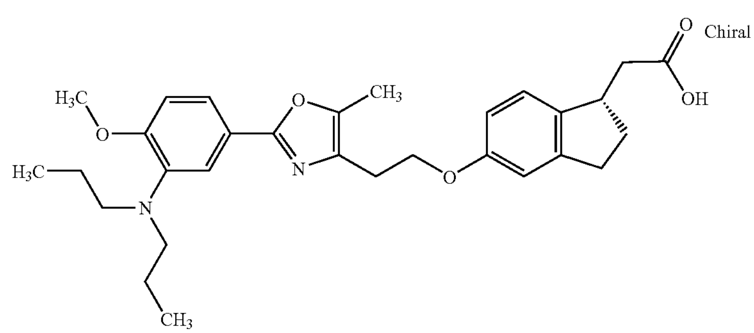 | 2.48 | 507.2 |
| 159 | 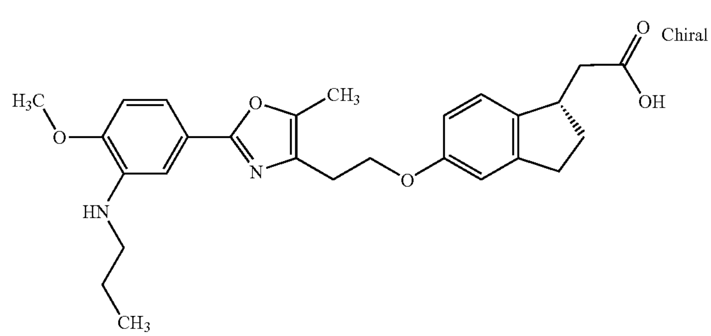 | 3.1 | 465.2 |

TABLE 1-continued

| Example No. | Structure | HPLC RT (min) | EI-MS [M + H]+ |
|---|---|---|---|
| 160 | 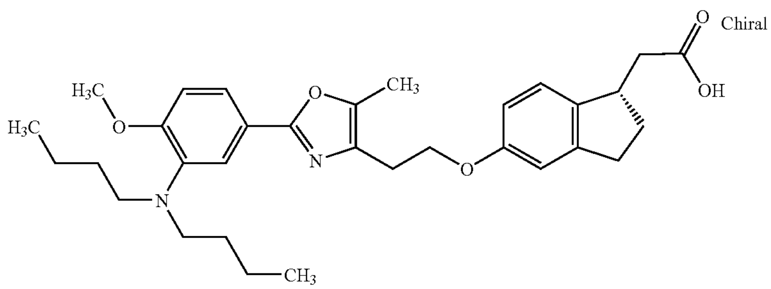 | 2.68 | 535.3 |
| 161 | 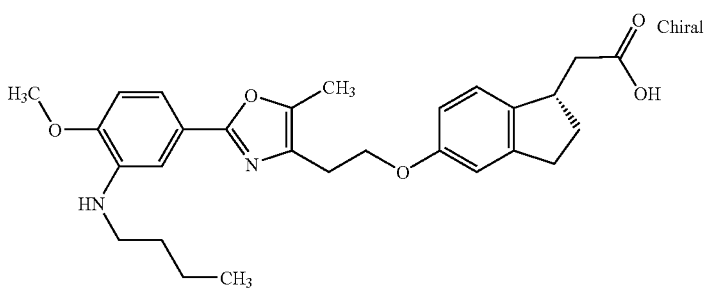 | 3.27 | 479.2 |
| 162 | 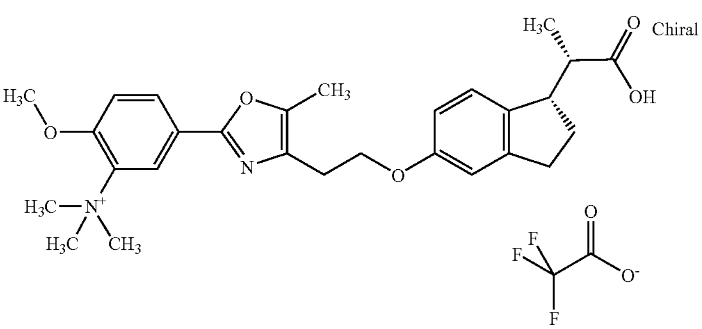 | 2.31 | 479.2 |
| 163 | 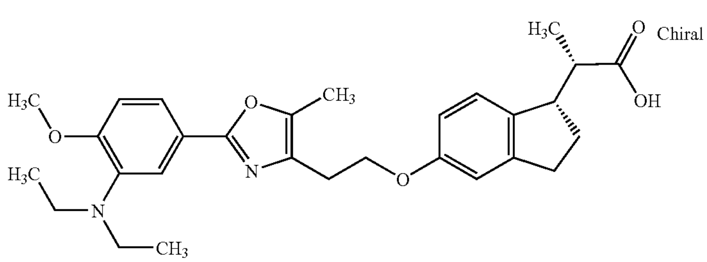 | 2.38 | 493.2 |
| 164 | 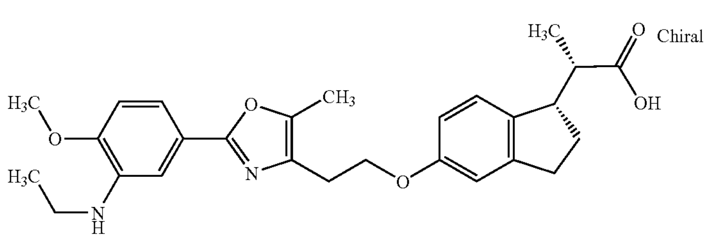 | 3.9 | 465.2 |

TABLE 1-continued

| Example No. | Structure | HPLC RT (min) | EI-MS [M + H]+ |
|---|---|---|---|
| 165 | 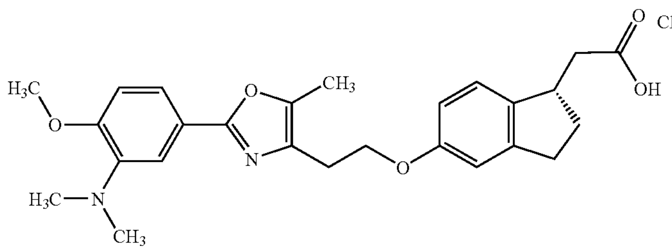 | 2.74 | 451.4 |
| 166 | 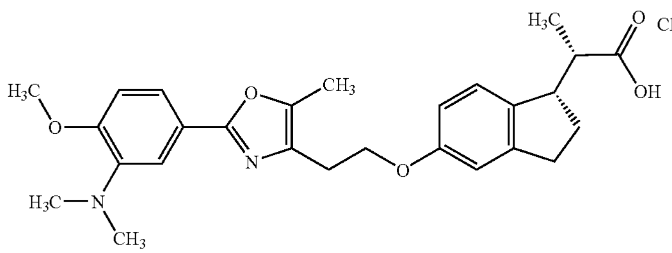 | 2.81 | 465.4 |
| 167 | 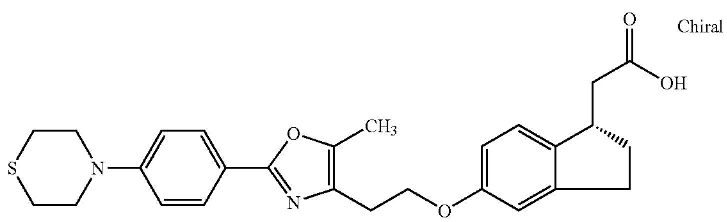 | 479 | 4.03 |
| 168 | 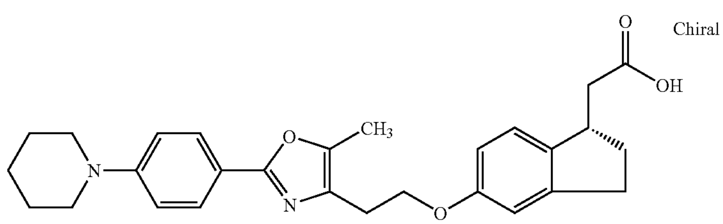 | 461 | 3.56 |
| 169 | 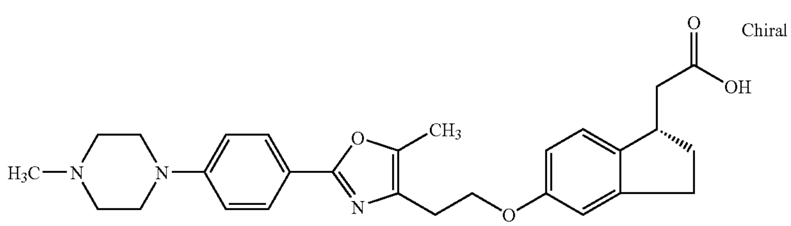 | 476 | 2.98 |
| 170 | 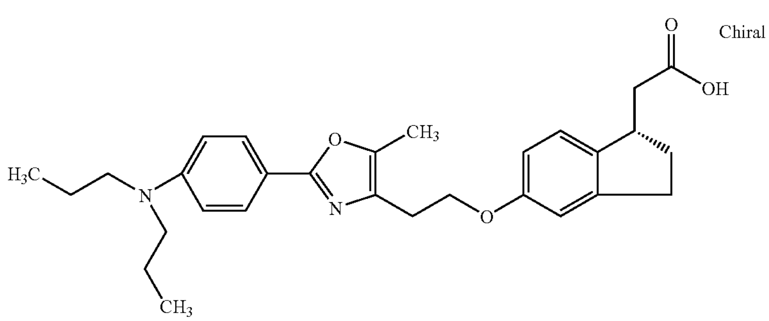 | 477 | 4.13 |

TABLE 1-continued

| Example No. | Structure | HPLC RT (min) | EI-MS [M + H]+ |
|---|---|---|---|
| 171 | 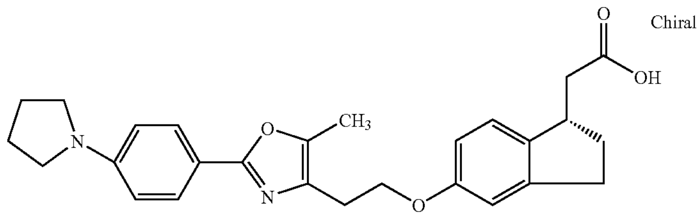 | 447 | 3.96 |
| 172 | 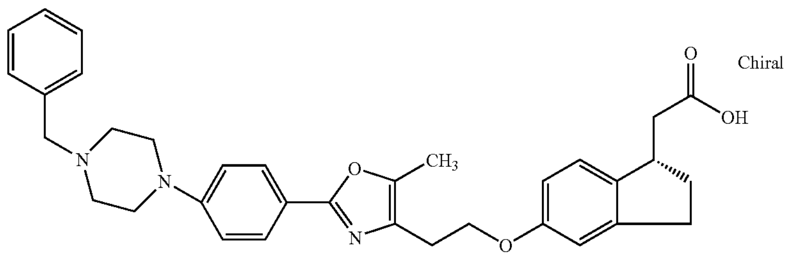 | 552 | 3.14 |
| 173 | 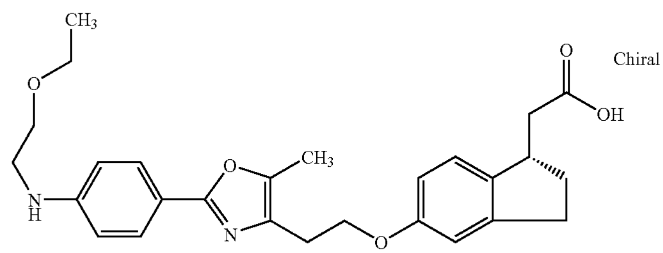 | 465 | 3.49 |
| 174 | 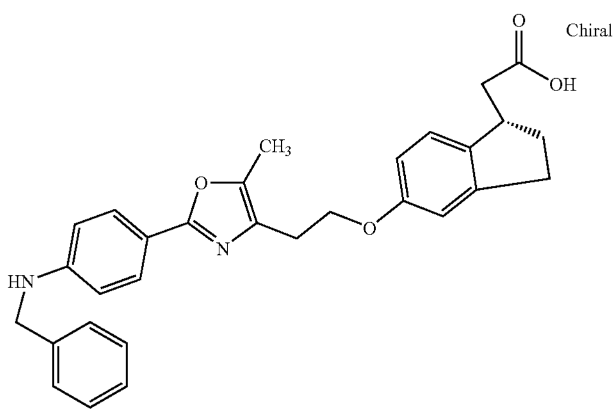 | 483 | 3.8 |
| 175 | 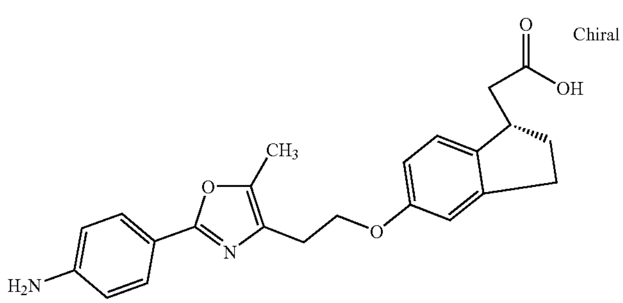 | 393 | 3.09 |

TABLE 1-continued

| Example No. | Structure | HPLC RT (min) | EI-MS [M + H]⁺ |
|---|---|---|---|
| 176 | 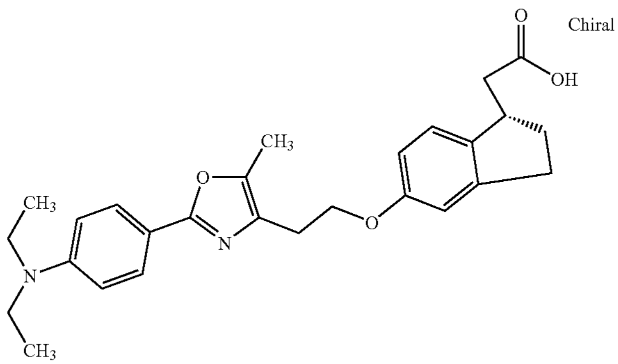 | 449 | 3.34 |
| 177 | 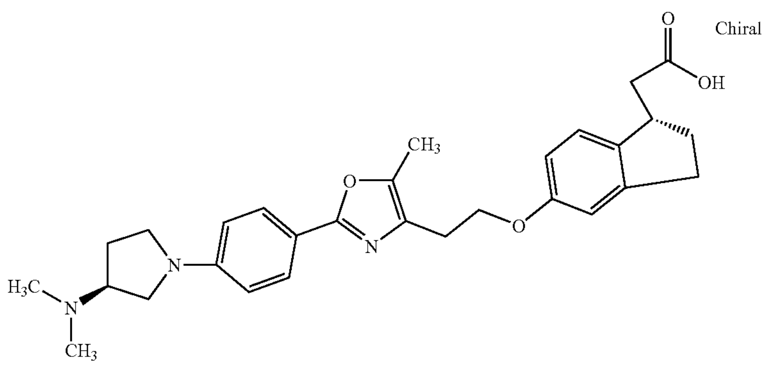 | 490 | 2.81 |
| 178 | 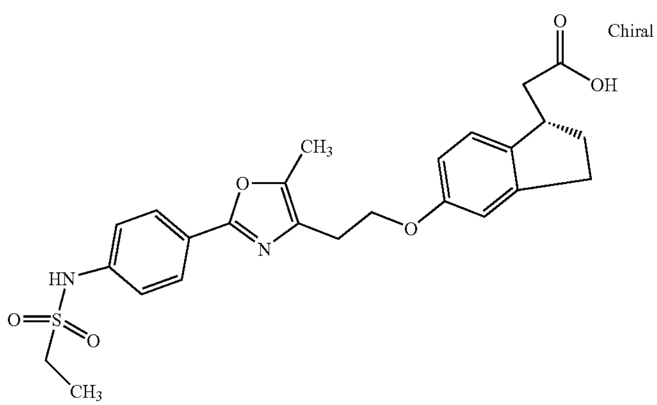 | 485 | 3.44 |
| 179 | 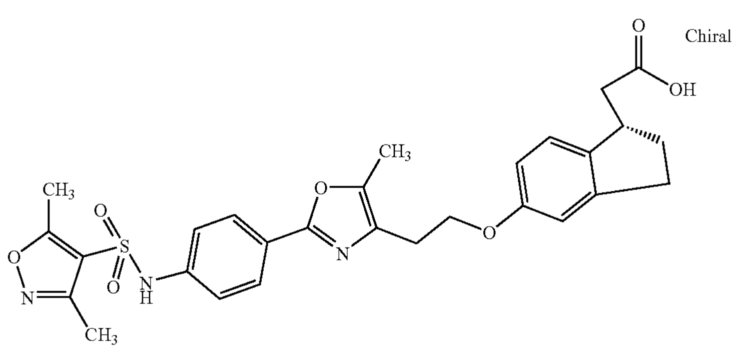 | 552 | 3.66 |

TABLE 1-continued

| Example No. | Structure | HPLC RT (min) | EI-MS [M + H]⁺ |
|---|---|---|---|
| 180 | 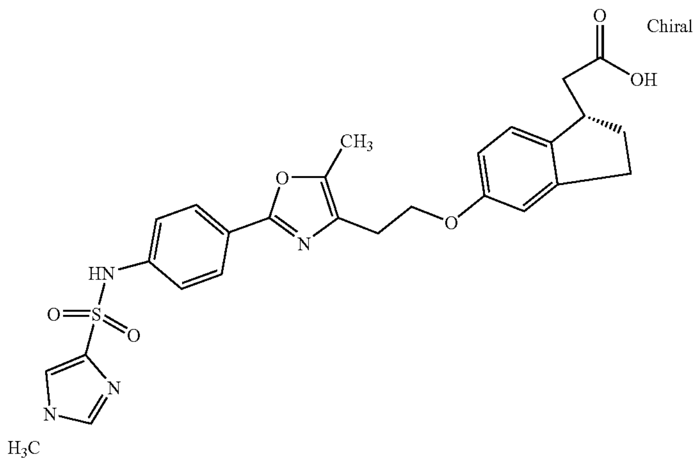 | 537 | 3.25 |
| 181 | 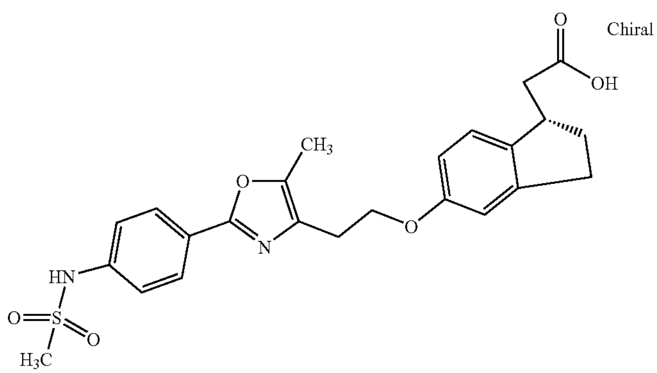 | 471 | 3.34 |
| 182 | 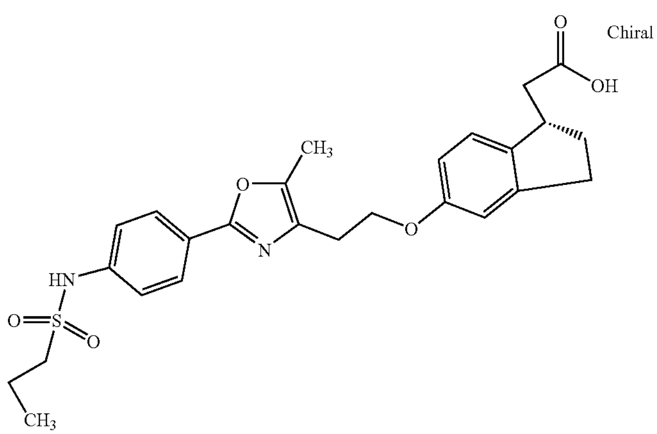 | 499 | 3.56 |
| 183 | 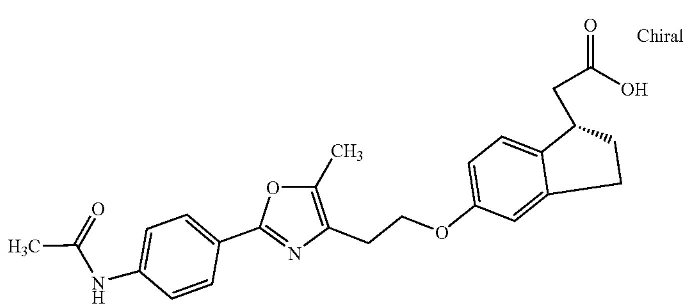 | 435 | 3.25 |

TABLE 1-continued

| Example No. | Structure | HPLC RT (min) | EI-MS [M + H]⁺ |
|---|---|---|---|
| 184 | (propanamide-phenyl-5-methyl-oxazole-ethoxy-indane-acetic acid, Chiral) | 449 | 3.4 |
| 185 | (isobutyramide-phenyl-5-methyl-oxazole-ethoxy-indane-acetic acid, Chiral) | 463 | 3.53 |
| 186 | (N,N-dimethylurea-phenyl-5-methyl-oxazole-ethoxy-indane-acetic acid, Chiral) | 464 | 3.25 |
| 187 | (thiophene-2-carboxamide-phenyl-5-methyl-oxazole-ethoxy-indane-acetic acid, Chiral) | 503 | 3.71 |
| 188 | (2-(methylthio)pyridine-3-carboxamide-phenyl-5-methyl-oxazole-ethoxy-indane-acetic acid, Chiral) | 544 | 3.66 |

TABLE 1-continued
| Example No. | Structure | HPLC RT (min) | EI-MS [M + H]+ |
|---|---|---|---|
| 189 | 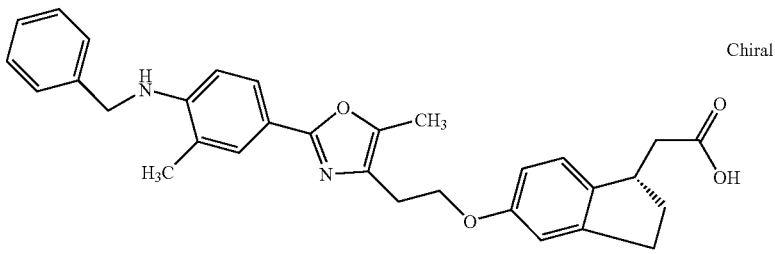 Chiral | 497 | 3.83 |
| 190 | 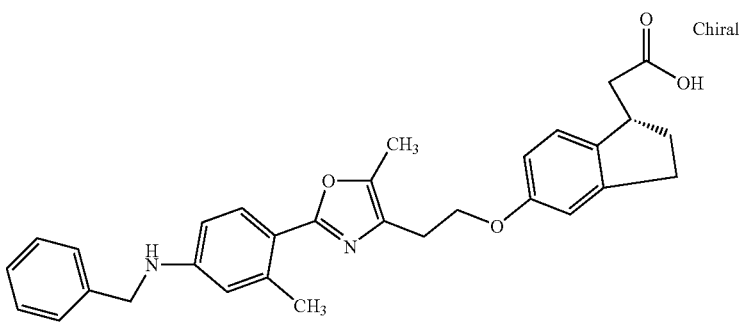 Chiral | 497 | 3.87 |
| 191 | 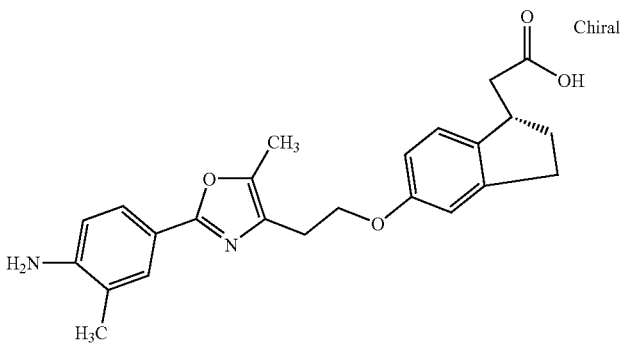 Chiral | 407 | 3.17 |
| 192 | 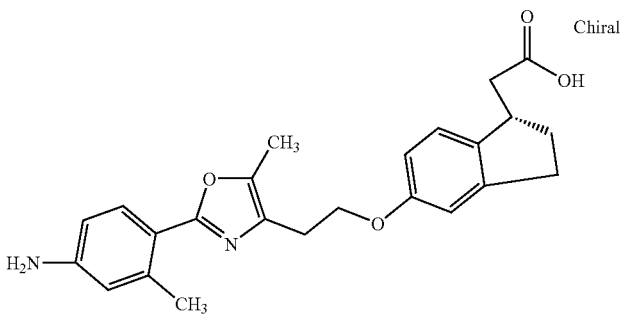 Chiral | 407 | 3.12 |
| 193 | 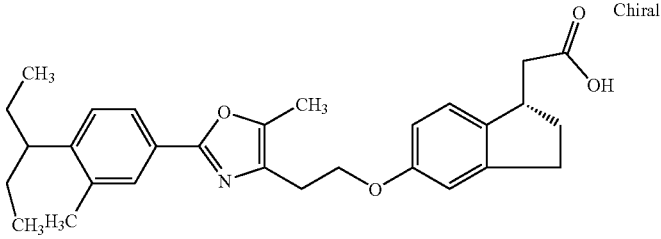 Chiral | 463 | 2.85 |

TABLE 1-continued

| Example No. | Structure | | HPLC RT (min) | EI-MS [M + H]+ |
|---|---|---|---|---|
| 194 | (structure) | Chiral | 449 | 2.74 |
| 195 | (structure) | Chiral | 491 | 3.95 |
| 196 | (structure) | Chiral | 449 | 3.67 |
| 197 | (structure) | Chiral | 435 | 3.57 |

TABLE 2

| Example No. | IUPAC NAME |
|---|---|
| 103 | [(1S)-5-(2-{2-[3-(benzylamino)phenyl]-5-methyl-1,3-oxazol-4-yl}ethoxy)-2,3-dihydro-1H-inden-1-yl]acetic acid |
| 104 | [(1S)-5-(2-{5-methyl-2-[3-(methylamino)phenyl]-1,3-oxazol-4-yl}ethoxy)-2,3-dihydro-1H-inden-1-yl]acetic acid |
| 105 | {(1S)-5-[2-(2-{3-[benzyl(methyl)amino]phenyl}-5-methyl-1,3-oxazol-4-yl)ethoxy]-2,3-dihydro-1H-inden-1-yl}acetic acid |
| 106 | ((1S)-5-{2-[2-(3-aminophenyl)-5-methyl-1,3-oxazol-4-yl]ethoxy}-2,3-dihydro-1H-inden-1-yl)acetic acid |
| 107 | {(1S)-5-[2-(5-methyl-2-{3-[methyl(propionyl)amino]phenyl}-1,3-oxazol-4-yl)ethoxy]-2,3-dihydro-1H-inden-1-yl}acetic acid |
| 108 | {(1S)-5-[2-(2-{3-[[(dimethylamino)carbonyl](methyl)amino]phenyl}-5-methyl-1,3-oxazol-4-yl)ethoxy]-2,3-dihydro-1H-inden-1-yl}acetic acid |
| 109 | [(1S)-5-(2-{5-methyl-2-[3-(propionylamino)phenyl]-1,3-oxazol-4-yl}ethoxy)-2,3-dihydro-1H-inden-1-yl]acetic acid |

TABLE 2-continued

| Example No. | IUPAC NAME |
|---|---|
| 110 | ((1S)-5-{2-[2-(3-{[(dimethylamino)carbonyl]amino}phenyl)-5-methyl-1,3-oxazol-4-yl]ethoxy}-2,3-dihydro-1H-inden-1-yl)acetic acid |
| 111 | {(1S)-5-[2-(2-{3-[(ethylsulfonyl)amino]phenyl}-5-methyl-1,3-oxazol-4-yl)ethoxy]-2,3-dihydro-1H-inden-1-yl}acetic acid |
| 112 | {(1S)-5-[2-(2-{3-[(isopropylsulfonyl)amino]phenyl}-5-methyl-1,3-oxazol-4-yl)ethoxy]-2,3-dihydro-1H-inden-1-yl}acetic acid |
| 113 | ((1S)-5-{2-[2-(3-{[(dimethylamino)sulfonyl]amino}phenyl)-5-methyl-1,3-oxazol-4-yl]ethoxy}-2,3-dihydro-1H-inden-1-yl)acetic acid |
| 114 | ((1S)-5-{2-[2-(3-{bis[(dimethylamino)sulfonyl]amino}phenyl)-5-methyl-1,3-oxazol-4-yl]ethoxy}-2,3-dihydro-1H-inden-1-yl)acetic acid |
| 115 | {(1S)-5-[2-(2-{3-[ethyl(methyl)amino]phenyl}-5-methyl-1,3-oxazol-4-yl)ethoxy]-2,3-dihydro-1H-inden-1-yl}acetic acid |
| 116 | [(1S)-5-(2-{2-[3-(dimethylamino)phenyl]-5-methyl-1,3-oxazol-4-yl}ethoxy)-2,3-dihydro-1H-inden-1-yl]acetic acid |
| 117 | 3-[4-(2-{[(1S)-1-(carboxymethyl)-2,3-dihydro-1H-inden-5-yl]oxy}ethyl)-5-methyl-1,3-oxazol-2-yl]-N,N,N-trimethylbenzenaminium trifluoroacetate |
| 118 | ((1S)-5-{2-[2-(3-{[(3,5-dimethyl-4-isoxazolyl)sulfonyl]amino}phenyl)-5-methyl-1,3-oxazol-4-yl]ethoxy}-2,3-dihydro-1H-inden-1-yl)acetic acid |
| 119 | ((1S)-5-{2-[2-(3-{[(1,2-dimethyl-1H-imidazol-4-yl)sulfonyl]amino}phenyl)-5-methyl-1,3-oxazol-4-yl]ethoxy}-2,3-dihydro-1H-inden-1-yl)acetic acid |
| 120 | ((1S)-5-{2-[5-methyl-2-(3-{[(1-methyl-1H-imidazol-4-yl)sulfonyl]amino}phenyl)-1,3-oxazol-4-yl]ethoxy}-2,3-dihydro-1H-inden-1-yl)acetic acid |
| 121 | [(1S)-5-(2-{2-[3-(diethylamino)phenyl]-5-methyl-1,3-oxazol-4-yl}ethoxy)-2,3-dihydro-1H-inden-1-yl]acetic acid |
| 122 | [(1S)-5-(2-{2-[3-(dipropylamino)phenyl]-5-methyl-1,3-oxazol-4-yl}ethoxy)-2,3-dihydro-1H-inden-1-yl]acetic acid |
| 123 | {(1S)-5-[2-(2-{3-[benzyl(ethyl)amino]phenyl}-5-methyl-1,3-oxazol-4-yl)ethoxy]-2,3-dihydro-1H-inden-1-yl}acetic acid |
| 124 | {(1S)-5-[2-(2-{3-[benzyl(propyl)amino]phenyl}-5-methyl-1,3-oxazol-4-yl)ethoxy]-2,3-dihydro-1H-inden-1-yl}acetic acid |
| 125 | {(1S)-5-[2-(2-{3-[benzyl(butyl)amino]phenyl}-5-methyl-1,3-oxazol-4-yl)ethoxy]-2,3-dihydro-1H-inden-1-yl}acetic acid |
| 126 | [(1S)-5-(2-{2-[3-(ethylamino)phenyl]-5-methyl-1,3-oxazol-4-yl}ethoxy)-2,3-dihydro-1H-inden-1-yl]acetic acid |
| 127 | [(1S)-5-(2-{5-methyl-2-[3-(propylamino)phenyl]-1,3-oxazol-4-yl}ethoxy)-2,3-dihydro-1H-inden-1-yl]acetic acid |
| 128 | [(1S)-5-(2-{2-[3-(butylamino)phenyl]-5-methyl-1,3-oxazol-4-yl}ethoxy)-2,3-dihydro-1H-inden-1-yl]acetic acid |
| 129 | {(1S)-5-[2-(2-{3-[(2-methoxyethyl)amino]phenyl}-5-methyl-1,3-oxazol-4-yl)ethoxy]-2,3-dihydro-1H-inden-1-yl}acetic acid |
| 130 | {(1S)-5-[2-(2-{3-[(2-ethoxyethyl)amino]phenyl}-5-methyl-1,3-oxazol-4-yl)ethoxy]-2,3-dihydro-1H-inden-1-yl}acetic acid |
| 131 | [(1S)-5-(2-{2-[3-(benzylamino)-4-methylphenyl]-5-methyl-1,3-oxazol-4-yl}ethoxy)-2,3-dihydro-1H-inden-1-yl]acetic acid |
| 132 | (2S)-2-[(1S)-5-(2-{2-[3-(benzylamino)-4-methylphenyl]-5-methyl-1,3-oxazol-4-yl}ethoxy)-2,3-dihydro-1H-inden-1-yl]propanoic acid |
| 133 | ((1S)-5-{2-[2-(3-amino-4-methylphenyl)-5-methyl-1,3-oxazol-4-yl]ethoxy}-2,3-dihydro-1H-inden-1-yl)acetic acid |
| 134 | (2S)-2-((1S)-5-{2-[2-(3-amino-4-methylphenyl)-5-methyl-1,3-oxazol-4-yl]ethoxy}-2,3-dihydro-1H-inden-1-yl)propanoic acid |
| 135 | {(1S)-5-[2-(2-{3-[benzyl(methyl)amino]-4-methylphenyl}-5-methyl-1,3-oxazol-4-yl)ethoxy]-2,3-dihydro-1H-inden-1-yl}acetic acid |
| 136 | {(1S)-5-[2-(2-{3-[benzyl(ethyl)amino]-4-methylphenyl}-5-methyl-1,3-oxazol-4-yl)ethoxy]-2,3-dihydro-1H-inden-1-yl}acetic acid |
| 137 | (2S)-2-{(1S)-5-[2-(2-{3-[benzyl(methyl)amino]-4-methylphenyl}-5-methyl-1,3-oxazol-4-yl)ethoxy]-2,3-dihydro-1H-inden-1-yl}propanoic acid |
| 138 | (2S)-2-{(1S)-5-[2-(2-{3-[benzyl(ethyl)amino]-4-methylphenyl}-5-methyl-1,3-oxazol-4-yl)ethoxy]-2,3-dihydro-1H-inden-1-yl}propanoic acid |
| 139 | {(1S)-5-[2-(2-{3-[benzyl(propyl)amino]-4-methylphenyl}-5-methyl-1,3-oxazol-4-yl)ethoxy]-2,3-dihydro-1H-inden-1-yl}acetic acid |
| 140 | {(1S)-5-[2-(2-{3-[benzyl(butyl)amino]-4-methylphenyl}-5-methyl-1,3-oxazol-4-yl)ethoxy]-2,3-dihydro-1H-inden-1-yl}acetic acid |
| 141 | (2S)-2-{(1S)-5-[2-(2-{3-[benzyl(propyl)amino]-4-methylphenyl}-5-methyl-1,3-oxazol-4-yl)ethoxy]-2,3-dihydro-1H-inden-1-yl}propanoic acid |
| 142 | (2S)-2-{(1S)-5-[2-(2-{3-[benzyl(butyl)amino]-4-methylphenyl}-5-methyl-1,3-oxazol-4-yl)ethoxy]-2,3-dihydro-1H-inden-1-yl}propanoic acid |
| 143 | [(1S)-5-(2-{2-[3-(ethylamino)-4-methylphenyl]-5-methyl-1,3-oxazol-4-yl}ethoxy)-2,3-dihydro-1H-inden-1-yl]acetic acid |
| 144 | [(1S)-5-(2-{5-methyl-2-[4-methyl-3-(propylamino)phenyl]-1,3-oxazol-4-yl}ethoxy)-2,3-dihydro-1H-inden-1-yl]acetic acid |
| 145 | [(1S)-5-(2-{2-[3-(butylamino)-4-methylphenyl]-5-methyl-1,3-oxazol-4-yl}ethoxy)-2,3-dihydro-1H-inden-1-yl]acetic acid |
| 146 | (2S)-2-[(1S)-5-(2-{5-methyl-2-[4-methyl-3-(methylamino)phenyl]-1,3-oxazol-4-yl}ethoxy)-2,3-dihydro-1H-inden-1-yl]propanoic acid |

TABLE 2-continued

| Example No. | IUPAC NAME |
|---|---|
| 147 | (2S)-2-[(1S)-5-(2-{2-[3-(ethylamino)-4-methylphenyl]-5-methyl-1,3-oxazol-4-yl}ethoxy)-2,3-dihydro-1H-inden-1-yl]propanoic acid |
| 148 | (2S)-2-[(1S)-5-(2-{5-methyl-2-[4-methyl-3-(butylamino)phenyl]-1,3-oxazol-4-yl}ethoxy)-2,3-dihydro-1H-inden-1-yl]propanoic acid |
| 149 | [(1S)-5-(2-{2-[3-(diethylamino)-4-methylphenyl]-5-methyl-1,3-oxazol-4-yl}ethoxy)-2,3-dihydro-1H-inden-1-yl]acetic acid |
| 150 | (2S)-2-[(1S)-5-(2-{2-[3-(dimethylamino)-4-methylphenyl]-5-methyl-1,3-oxazol-4-yl}ethoxy)-2,3-dihydro-1H-inden-1-yl]propanoic acid |
| 151 | (2S)-2-[(1S)-5-(2-{2-[3-(diethylamino)-4-methylphenyl]-5-methyl-1,3-oxazol-4-yl}ethoxy)-2,3-dihydro-1H-inden-1-yl]propanoic acid |
| 152 | (2S)-2-[(1S)-5-(2-{5-methyl-2-[4-methyl-3-(propylamino)phenyl]-1,3-oxazol-4-yl}ethoxy)-2,3-dihydro-1H-inden-1-yl]propanoic acid |
| 153 | (2S)-2-((1S)-5-{2-[2-(3-amino-4-methoxyphenyl)-5-methyl-1,3-oxazol-4-yl]ethoxy}-2,3-dihydro-1H-inden-1-yl)propanoic acid |
| 154 | ((1S)-5-{2-[2-(3-amino-4-methoxyphenyl)-5-methyl-1,3-oxazol-4-yl]ethoxy}-2,3-dihydro-1H-inden-1-yl)acetic acid |
| 155 | 5-[4-(2-{[(1S)-1-(carboxymethyl)-2,3-dihydro-1H-inden-5-yl]oxy}ethyl)-5-methyl-1,3-oxazol-2-yl]-2-methoxy-N,N,N-trimethylbenzenaminium trifluoroacetate |
| 156 | [(1S)-5-(2-{2-[3-(diethylamino)-4-methoxyphenyl]-5-methyl-1,3-oxazol-4-yl}ethoxy)-2,3-dihydro-1H-inden-1-yl]acetic acid |
| 157 | [(1S)-5-(2-{2-[3-(ethylamino)-4-methoxyphenyl]-5-methyl-1,3-oxazol-4-yl}ethoxy)-2,3-dihydro-1H-inden-1-yl]acetic acid |
| 158 | [(1S)-5-(2-{2-[3-(dipropylamino)-4-methoxyphenyl]-5-methyl-1,3-oxazol-4-yl}ethoxy)-2,3-dihydro-1H-inden-1-yl]acetic acid |
| 159 | [(1S)-5-(2-{2-[4-methoxy-3-(propylamino)phenyl]-5-methyl-1,3-oxazol-4-yl}ethoxy)-2,3-dihydro-1H-inden-1-yl]acetic acid |
| 160 | [(1S)-5-(2-{2-[3-(dibutylamino)-4-methoxyphenyl]-5-methyl-1,3-oxazol-4-yl}ethoxy)-2,3-dihydro-1H-inden-1-yl]acetic acid |
| 161 | [(1S)-5-(2-{2-[3-(butylamino)-4-methoxyphenyl]-5-methyl-1,3-oxazol-4-yl}ethoxy)-2,3-dihydro-1H-inden-1-yl]acetic acid |
| 162 | 5-{4-[2-({(1S)-1-[(1S)-1-carboxyethyl]-2,3-dihydro-1H-inden-5-yl}oxy)ethyl]-5-methyl-1,3-oxazol-2-yl}-2-methoxy-N,N,N-trimethylbenzenaminium trifluoroacetate |
| 163 | (2S)-2-[(1S)-5-(2-{2-[3-(diethylamino)-4-methoxyphenyl]-5-methyl-1,3-oxazol-4-yl}ethoxy)-2,3-dihydro-1H-inden-1-yl]propanoic acid |
| 164 | (2S)-2-[(1S)-5-(2-{2-[3-(ethylamino)-4-methoxyphenyl]-5-methyl-1,3-oxazol-4-yl}ethoxy)-2,3-dihydro-1H-inden-1-yl]propanoic acid |
| 165 | [(1S)-5-(2-{2-[3-(dimethylamino)-4-methoxyphenyl]-5-methyl-1,3-oxazol-4-yl}ethoxy)-2,3-dihydro-1H-inden-1-yl]acetic acid |
| 166 | (2S)-2-[(1S)-5-(2-{2-[3-(dimethylamino)-4-methoxyphenyl]-5-methyl-1,3-oxazol-4-yl}ethoxy)-2,3-dihydro-1H-inden-1-yl]propanoic acid |
| 167 | [(1S)-5-(2-{5-methyl-2-[4-(4-thiomorpholinyl)phenyl]-1,3-oxazol-4-yl}ethoxy)-2,3-dihydro-1H-inden-1-yl]acetic acid |
| 168 | [(1S)-5-(2-{5-methyl-2-[4-(1-piperidinyl)phenyl]-1,3-oxazol-4-yl}ethoxy)-2,3-dihydro-1H-inden-1-yl]acetic acid |
| 169 | [(1S)-5-(2-{5-methyl-2-[4-(4-methyl-1-piperazinyl)phenyl]-1,3-oxazol-4-yl}ethoxy)-2,3-dihydro-1H-inden-1-yl]acetic acid |
| 170 | [(1S)-5-(2-{2-[4-(dipropylamino)phenyl]-5-methyl-1,3-oxazol-4-yl}ethoxy)-2,3-dihydro-1H-inden-1-yl]acetic acid |
| 171 | [(1S)-5-(2-{5-methyl-2-[4-(1-pyrrolidinyl)phenyl]-1,3-oxazol-4-yl}ethoxy)-2,3-dihydro-1H-inden-1-yl]acetic acid |
| 172 | [(1S)-5-(2-{2-[4-(4-benzyl-1-piperazinyl)phenyl]-5-methyl-1,3-oxazol-4-yl}ethoxy)-2,3-dihydro-1H-inden-1-yl]acetic acid |
| 173 | {(1S)-5-[2-(2-{4-[(2-ethoxyethyl)amino]phenyl}-5-methyl-1,3-oxazol-4-yl)ethoxy]-2,3-dihydro-1H-inden-1-yl}acetic acid |
| 174 | [(1S)-5-(2-{2-[4-(benzylamino)phenyl]-5-methyl-1,3-oxazol-4-yl}ethoxy)-2,3-dihydro-1H-inden-1-yl]acetic acid |
| 175 | ((1S)-5-{2-[2-(4-aminophenyl)-5-methyl-1,3-oxazol-4-yl]ethoxy}-2,3-dihydro-1H-inden-1-yl)acetic acid |
| 176 | [(1S)-5-(2-{2-[4-(diethylamino)phenyl]-5-methyl-1,3-oxazol-4-yl}ethoxy)-2,3-dihydro-1H-inden-1-yl]acetic acid |
| 177 | {(1S)-5-[2-(2-{4-[(3S)-3-(dimethylamino)-1-pyrrolidinyl]phenyl}-5-methyl-1,3-oxazol-4-yl)ethoxy]-2,3-dihydro-1H-inden-1-yl}acetic acid |
| 178 | {(1S)-5-[2-(2-{4-[(ethylsulfonyl)amino]phenyl}-5-methyl-1,3-oxazol-4-yl)ethoxy]-2,3-dihydro-1H-inden-1-yl}acetic acid |

TABLE 2-continued

| Example No. | IUPAC NAME |
|---|---|
| 179 | ((1S)-5-{2-[2-(4-{[(3,5-dimethyl-4-isoxazolyl)sulfonyl]amino}phenyl)-5-methyl-1,3-oxazol-4-yl]ethoxy}-2,3-dihydro-1H-inden-1-yl)acetic acid |
| 180 | ((1S)-5-{2-[5-methyl-2-(4-{[(1-methyl-1H-imidazol-4-yl)sulfonyl]amino}phenyl)-1,3-oxazol-4-yl]ethoxy}-2,3-dihydro-1H-inden-1-yl)acetic acid |
| 181 | {(1S)-5-[2-(5-methyl-2-{4-[(methylsulfonyl)amino]phenyl}-1,3-oxazol-4-yl)ethoxy]-2,3-dihydro-1H-inden-1-yl}acetic acid |
| 182 | {(1S)-5-[2-(5-methyl-2-{4-[(propylsulfonyl)amino]phenyl}-1,3-oxazol-4-yl)ethoxy]-2,3-dihydro-1H-inden-1-yl}acetic acid |
| 183 | [(1S)-5-(2-{2-[4-(acetylamino)phenyl]-5-methyl-1,3-oxazol-4-yl}ethoxy)-2,3-dihydro-1H-inden-1-yl]acetic acid |
| 184 | [(1S)-5-(2-{5-methyl-2-[4-(propionylamino)phenyl]-1,3-oxazol-4-yl}ethoxy)-2,3-dihydro-1H-inden-1-yl]acetic acid |
| 185 | [(1S)-5-(2-{2-[4-(isobutyrylamino)phenyl]-5-methyl-1,3-oxazol-4-yl}ethoxy)-2,3-dihydro-1H-inden-1-yl]acetic acid |
| 186 | ((1S)-5-{2-[2-(4-{[(dimethylamino)carbonyl]amino}phenyl)-5-methyl-1,3-oxazol-4-yl]ethoxy}-2,3-dihydro-1H-inden-1-yl)acetic acid |
| 187 | {(1S)-5-[2-(5-methyl-2-{4-[(2-thienylcarbonyl)amino]phenyl}-1,3-oxazol-4-yl)ethoxy]-2,3-dihydro-1H-inden-1-yl}acetic acid |
| 188 | [(1S)-5-(2-{5-methyl-2-[4-({[2-{methylsulfanyl)-3-pyridinyl]carbonyl}amino)phenyl]-1,3-oxazol-4-yl}ethoxy)-2,3-dihydro-1H-inden-1-yl]acetic acid |
| 189 | [(1S)-5-(2-{2-[4-{benzylamino)-3-methylphenyl]-5-methyl-1,3-oxazol-4-yl}ethoxy)-2,3-dihydro-1H-inden-1-yl]acetic acid |
| 190 | [(1S)-5-(2-{2-[4-(benzylamino)-2-methylphenyl]-5-methyl-1,3-oxazol-4-yl}ethoxy)-2,3-dihydro-1H-inden-1-yl]acetic acid |
| 191 | ((1S)-5-{2-[2-(4-amino-3-methylphenyl)-5-methyl-1,3-oxazol-4-yl]ethoxy}-2,3-dihydro-1H-inden-1-yl)acetic acid |
| 192 | ((1S)-5-{2-[2-(4-amino-2-methylphenyl)-5-methyl-1,3-oxazol-4-yl]ethoxy}-2,3-dihydro-1H-inden-1-yl)acetic acid |
| 193 | [(1S)-5-(2-{2-[4-(diethylamino)-3-methylphenyl]-5-methyl-1,3-oxazol-4-yl}ethoxy)-2,3-dihydro-1H-inden-1-yl]acetic acid |
| 194 | 4-[4-(2-{[(1S)-1-(carboxymethyl)-2,3-dihydro-1H-inden-5-yl]oxy}ethyl)-5-methyl-1,3-oxazol-2-yl]-N,N,N,3-tetramethylbenzenaminium trifluoroacetate |
| 195 | [(1S)-5-(2-{2-[4-(dipropylamino)-2-methylphenyl]-5-methyl-1,3-oxazol-4-yl}ethoxy)-2,3-dihydro-1H-inden-1-yl]acetic acid |
| 196 | [(1S)-5-(2-{5-methyl-2-[2-methyl-4-(propylamino)phenyl]-1,3-oxazol-4-yl}ethoxy)-2,3-dihydro-1H-inden-1-yl]acetic acid |
| 197 | [(1S)-5-(2-{2-[4-{dimethylamino)-2-methylphenyl]-5-methyl-1,3-oxazol-4-yl}ethoxy)-2,3-dihydro-1H-inden-1-yl]acetic acid |

EXAMPLE 198

Preparation of [(1S)-5-(2-{2-[4-(2,4-dimethoxy-pyrimidin-5-yl)-phenyl]-5-methyl-oxazol-4-yl}-ethoxy)-indan-1-yl]-acetic acid ethyl ester

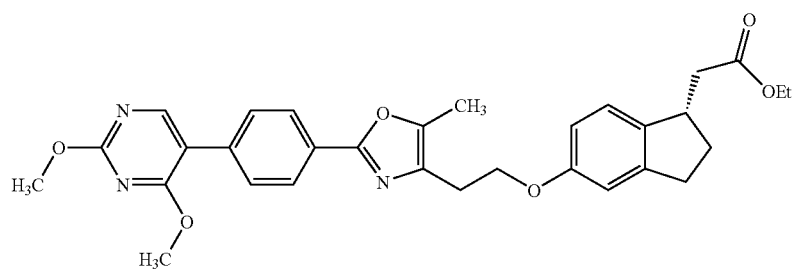

To a solution containing (1S)-(5-{2-[2-(4-bromo-phenyl)-5-methyl-oxazole-4-yl]-ethoxy}-indan-1-yl)-acetic acid ethyl ester (0.100 g, 0.21 mmol), 1,1'-phosphino)ferrocene] dichloro palladium(II) (16.9 mg, 0.02 mmol), and 2,4-dimethoxy-pyrimidin-5-boronic acid (0.076 g, 0.41 mmol) in degassed toluene and dioxane (4:1, 2 mL) was added aqueous 2 M sodium carbonate (0.5 mL). The mixture was heated at 85° C. for 16 hours. The reaction mixture was cool to rt and concentrated under vacuum and the residue was dissolved in methanol and acetonitrile and filtered through a C8 reverse phase extraction cartridge. The filtrated concentrated and the residue was purified by preparative HPLC to obtain [(1S)-5-(2-{2-[4-(2,4-dimethoxy-pyrimidin-5-yl)-phenyl]-5-methyl-oxazol-4-yl}-ethoxy)-indan-1-yl]-acetic acid ethyl ester in 45% yield, (50 mg, 0.09 mmol). $^1$H NMR (CD$_3$Cl) δ 1.3 (t, 3H), 1.8 (m, 1H), 2.4 (m, 5H), 2.9 (m, 3H) 3.1 (t, 2H), 3.5 (m, 1H), 4.1 (s, 6H), 4.2 (m, 4H), 6.7 (m, 2H), 7.1 (d, 1H) 7.8 (d, 2H), 8.4 (s, 1H); MS (ES) 544 (M+1)+.

EXAMPLE 199

[(1S)-5-(2-{2-[4-(2,4-Dimethoxy-5-pyrimidinyl) phenyl]-5-methyl-1,3-oxazol-4-yl}ethoxy)-2,3-dihydro-1H-inden-1-yl]acetic acid

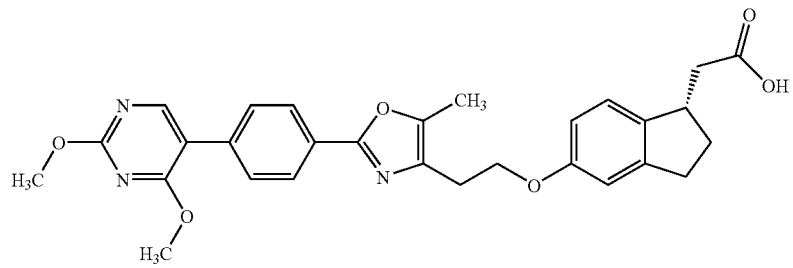

The procedure for the hydrolysis of the ester of Example 198 was similar to Example 61; $^1$H NMR (CD$_3$Cl) δ 1.8 (m, 1H), 2.4 (m, 5H), 2.9 (m, 3H), 3.0 (t, 2H), 3.5 (m, 1H), 4.1 (s, 6H), 4.2 (t, 2H), 6.7 (m, 2H), 7.1 (d, 1H) 7.6 (d, 2H), 8.0 (d, 2H), 8.4 (s, 1H); MS (ES) 516 (M+1)+.

EXAMPLE 200

Preparation of ethyl ((1S)-5-{2-[5-methyl-2-(3-vinylphenyl)-1,3-oxazol-4-yl]ethoxy}-2,3-dihydro-1H-inden-1-yl)acetate

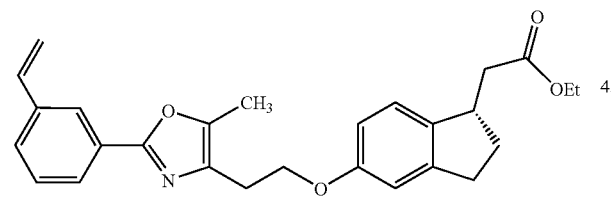

To a mixture of vinyltributyltin (Aldrich, 65.0 mg, 0.21 mmol), ethyl ((1S)-5-{2-[2-(3-bromophenyl)-5-methyl-1,3-oxazol-4-yl]ethoxy}-2,3-dihydro-1H-inden-1-yl)acetate (50 mg, 0.10 mmol), and [1,1'-bis(diphenylphosphino)-ferrocene]dichloropalladium(II), complex with dichloromethane (1:1) (4.2 mg, 0.005 mmol) was added toluene (2 mL). The resulting solution was degassed with argon for 30 minutes, and then stirred at 110° C. for 16 h. The reaction mixture was cooled to rt and diluted with 10 mL ethyl acetate. The organic layer was filtered through a silica plug and the filtrate concentrated under reduced pressure. The crude was then redissolved in methanol and filtered through a silica-octyl plug before preparative HPLC purification using 30 to 100% acetonitrile in water (0.1% TFA) gradient to afford the desired product. $^1$H NMR (CD$_2$Cl$_2$) δ 8.03 (s, 1H), 7.86 (d, 1H), 7.39-7.51 (m, 2H), 7.04 (d, 1H), 6.68-6.84 (m, 3H), 5.88 ((d, 1H), 5.31-5.35 (m, 1H), 4.10-4.23 (m, 4H), 3.48 (qr, 1H), 2.97 (t, 2H), 2.64-2.89 (m, 3H), 2.29-2.42 (m, 5H), 1.69-1.76 (m, 1H), 1.26 (t, 3H).

EXAMPLE 201

Preparation of ethyl ((1S)-5-{2-[5-methyl-2-(3-vinylphenyl)-1,3-oxazol-4-yl]ethoxy}-2,3-dihydro-1H-inden-1-yl)acetate

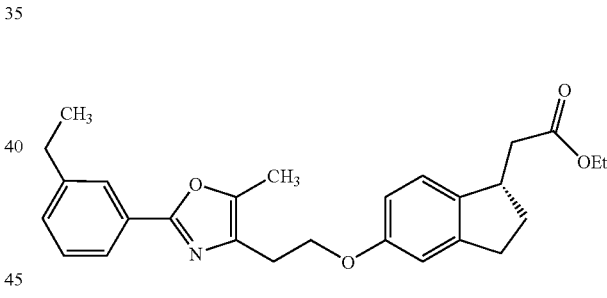

To a 25 mL dried flask was added Pd/C (10% wt, 4 mg), and the flask was flushed with argon. Ethanol (0.5 mL) was added to the reaction vessel, followed by a solution of ethyl ((1S)-5-{2-[5-methyl-2-(3-vinylphenyl)-1,3-oxazol4-yl]ethoxy}-2,3-dihydro-1H-inden-1-yl)acetate (60 mg, 0.14 mmol) in a mixture of ethyl acetate and ethanol (1/1). The flask was then flushed with hydrogen for 5 minutes and the mixture was then stirred under 1 atm of hydrogen for 16 h. The flask was flushed with argon and the reaction mixture was filtered through a Celite® plug. The filtrate was then concentrated under reduced pressure to afford 52 mg (86%) of desired product. $^1$H NMR (CD$_2$Cl$_2$) δ 7.73 (s, 1H), 7.68 (d, 1H), 7.26 (t, 1H), 7.17 (d, 1H), 6.95 (d, 1H), 6.69 (s, 1H), 6.60 (d, 1H), 3.97-4.13 (m, 4H), 3.39 (qr, 1H), 2.85 (t, 2H), 2.55-2.80 (m, 5H), 2.20-2.33 (m, 5H), 1.55-1.67 (m, 1H), 1.10-1.21 (m, 6 H). EI-LCMS(rel abundance), RT=4.66, m/z 434.4 (MH+, 100%).

EXAMPLE 202

Preparation of ((1S)-5-{2-[5-methyl-2-(3-vinylphenyl)-1,3-oxazol-4-yl]ethoxy}-2,3-dihydro-1H-inden-1-yl)acetic acid

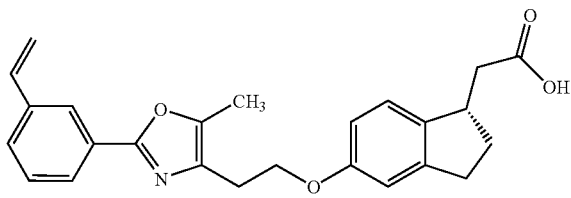

To a solution of ethyl ((1S)-5-{2-[5-methyl-2-(3-vinylphenyl)-1,3-oxazol-4-yl]ethoxy}-2,3-dihydro-1H-inden-1-yl)acetate (40 mg, 0.09 mmol) in ethanol (1.0 mL) and THF (1.0 mL) was added LiOH (39 mg) followed by water (1 mL). The reaction mixture was then stirred at rt for 4 h. The reaction mixture was then acidified to pH 5-6 and concentrated under reduced pressure. The residue redissolved in methanol, and filtered through a $C_8$-Silica plug. The filtrate was then purified by preparative HPLC using with 10 to 70% acetonitrile in water to afford 27.2 mg (72%) of desired product. $^1$H NMR (CD$_2$Cl$_2$) δ 7.97 (s, 1H), 7.79 (d, 1H), 7.42 (d, 1H), 7.35 (t, 1H), 7.02 (d, 1H), 6.62-6.76 (m, 3H), 5.80 (d, 1H), 5.27 (d, 1H), 4.14 (t, 2H), 3.43 (qr, 1H), 2.90 (t, 2H), 2.66-2.83 (m, 3H), 2.29-2.43 (m, 5H), 1.67-1.72 (m, 1H). EI-LCMS(rel abundance), RT=3.95, m/z 404.4 (MH+, 72%).

EXAMPLE 203

((1S)-5-{2-[5-Methyl-2-(3-ethylphenyl)-1,3-oxazol-4-yl]ethoxy}-2,3-dihydro-1H-inden-1-yl)acetic acid

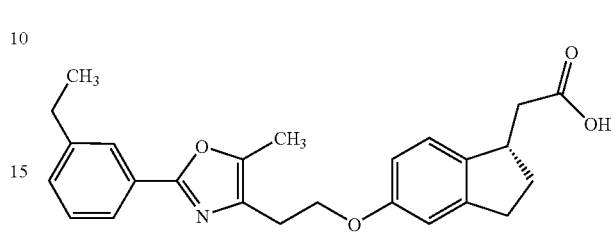

The product was prepared by following the hydrolysis procedure described of Example 61 and starting with Example 202. $^1$H NMR (CD$_2$Cl$_2$) δ 7.76 (s, 1H), 7.70 (d, 1H), 7.28 (t, 1H), 7.20 (d, 1H), 7.01 (d, 1H), 6.72 (s, 1H), 6.64 (d, 1H), 4.13 (t, 2H), 3.43 (qr, 1H), 2.88 (t, 2H), 2.60-2.82 (m, 5H), 2.26-2.43 (m, 5H), 1.61-1.73 (m, 1H), 1.21 (t, 3H). EI-LCMS(rel abundance), RT=4.03, m/z 406.4 (MH+, 100%).

Using the methods described above and the appropriate starting materials, the compounds in Table 3 may be prepared. The corresponding IUPAC names for the compounds in Table 3 may be found on Table 4.

TABLE 3

| Example No. | Structure | EI-MS [M + H]+ | HPLC RT (min) |
|---|---|---|---|
| 204 | 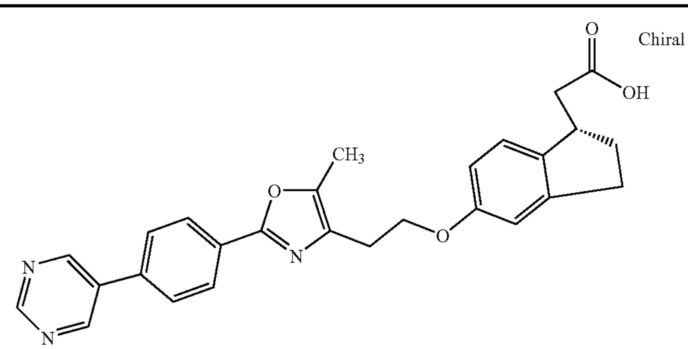 | 456 | 2.86 |
| 205 | 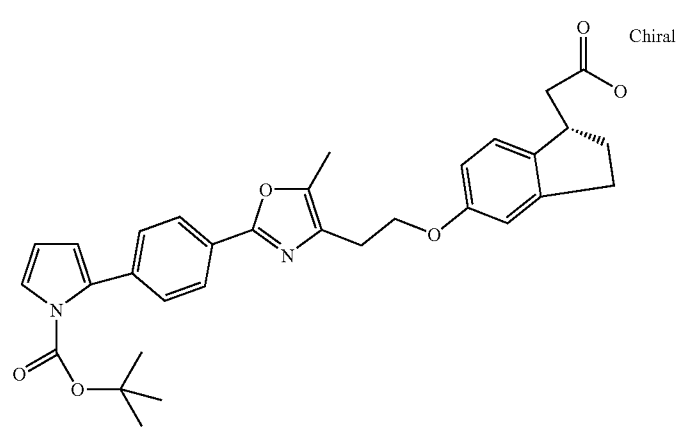 | 543 | 3.87 |

TABLE 3-continued

| Example No. | Structure | EI-MS [M + H]+ | HPLC RT (min) |
| --- | --- | --- | --- |
| 206 | 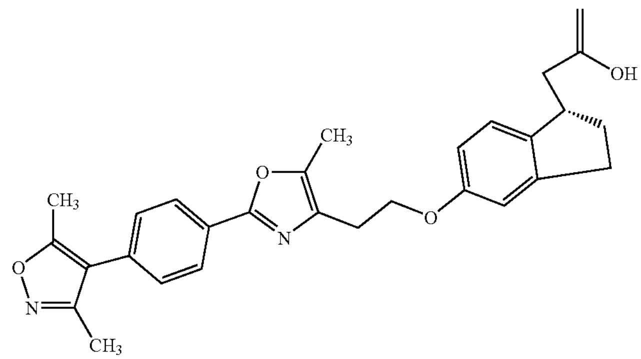 | 473 | 3.29 |
| 207 | 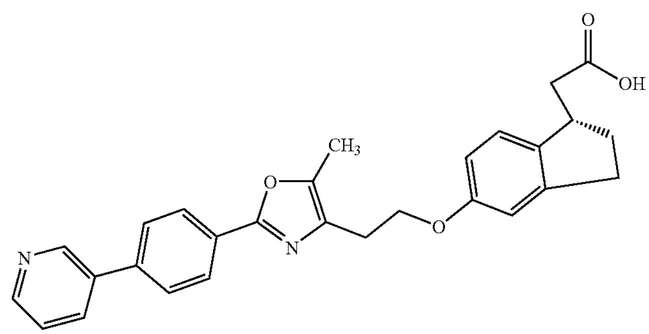 | 455 | 2.45 |
| 208 | 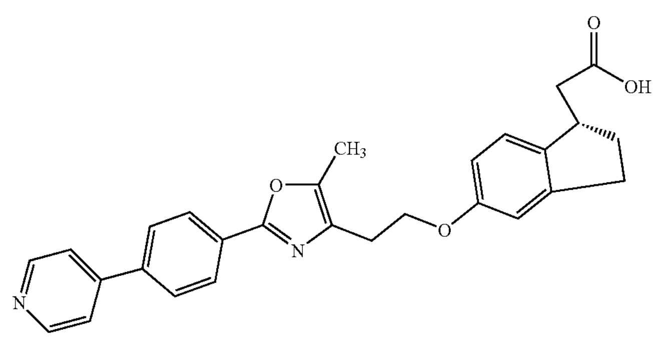 | 455 | 2.34 |
| 209 | 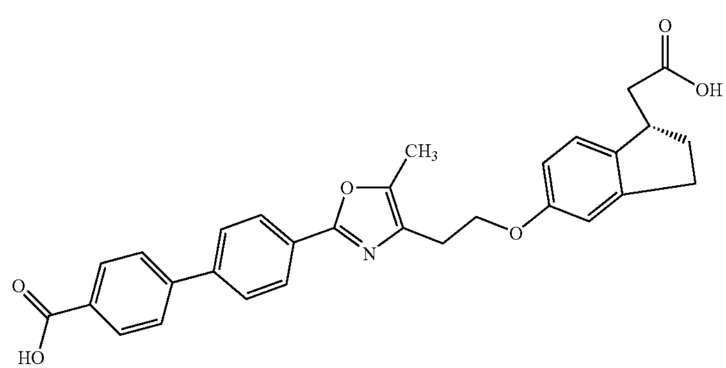 | 498 | 3.21 |

TABLE 3-continued

| Example No. | Structure | EI-MS [M + H]+ | HPLC RT (min) |
|---|---|---|---|
| 210 | 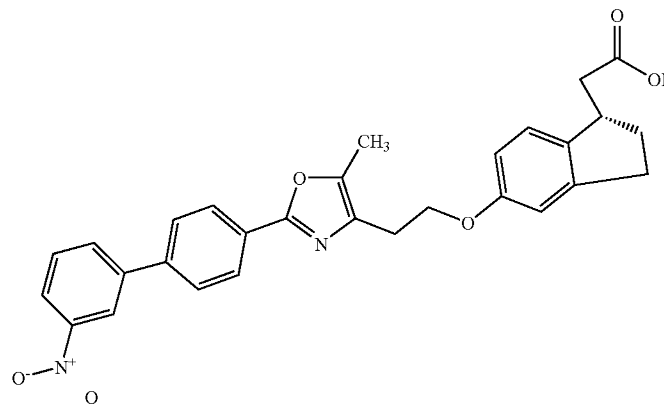 | 499 | 4.38 |
| 211 | 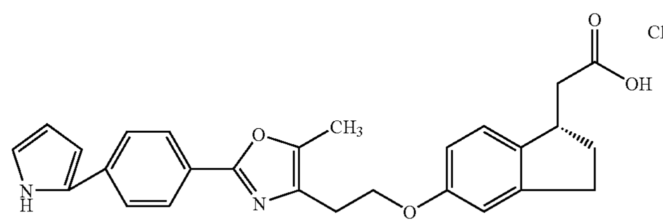 | 443 | 3.27 |
| 212 | 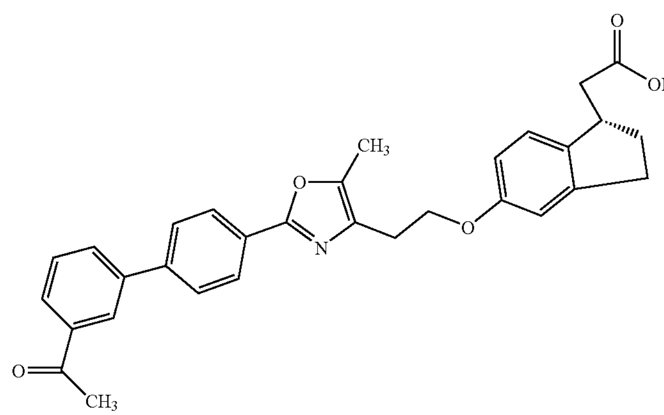 | 496 | 4.22 |
| 213 | 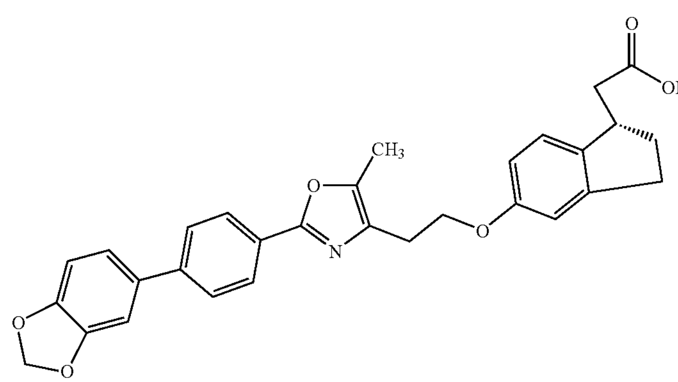 | 498 | 4.35 |

TABLE 3-continued

| Example No. | Structure | EI-MS [M + H]+ | HPLC RT (min) |
|---|---|---|---|
| 214 | 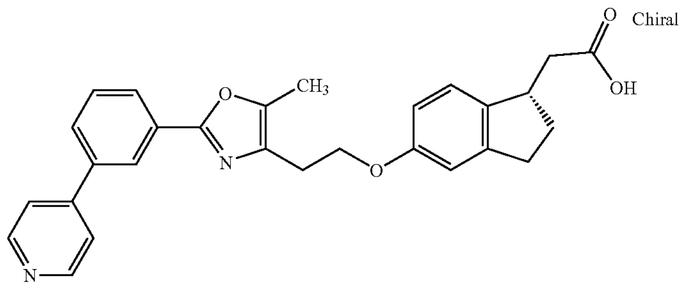 | 3.09 | 455.3 |
| 215 | 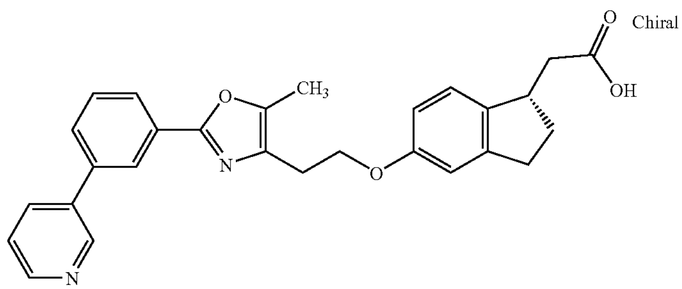 | 3.19 | 455.3 |
| 216 | 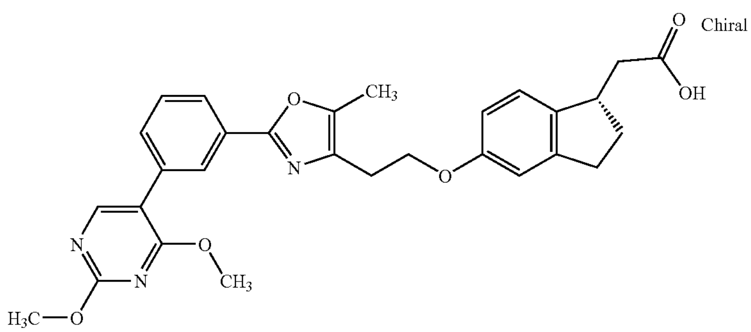 | 4 | 516.3 |
| 217 | 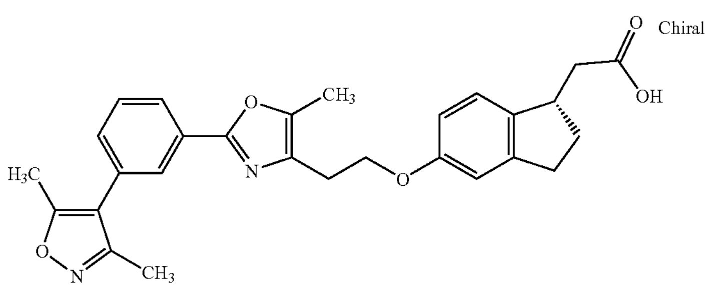 | 4.01 | 473.3 |
| 218 | 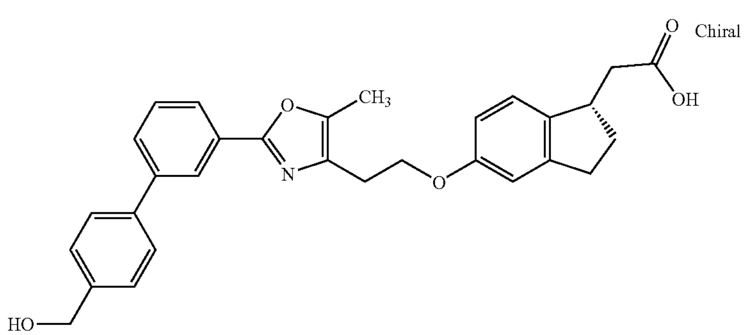 | 3.88 | 484.4 |

TABLE 3-continued

| Example No. | Structure | EI-MS [M + H]+ | HPLC RT (min) |
|---|---|---|---|
| 219 | 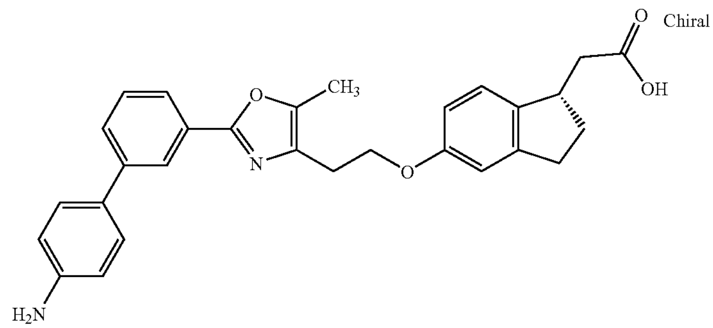 | 3.43 | 469.3 |
| 220 | 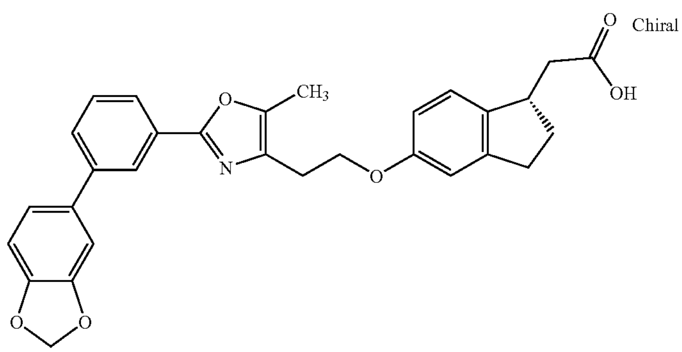 | 4.35 | 498.4 |
| 221 | 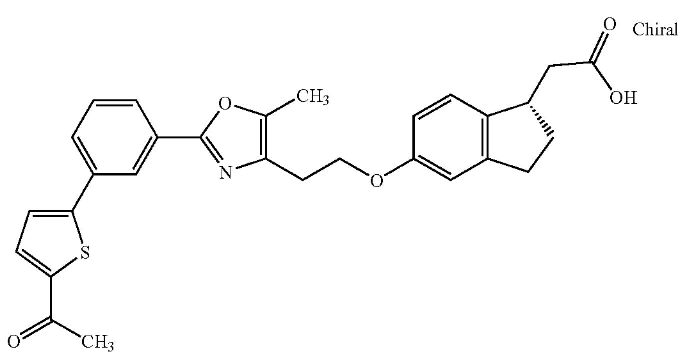 | 4.19 | 502.3 |
| 222 | 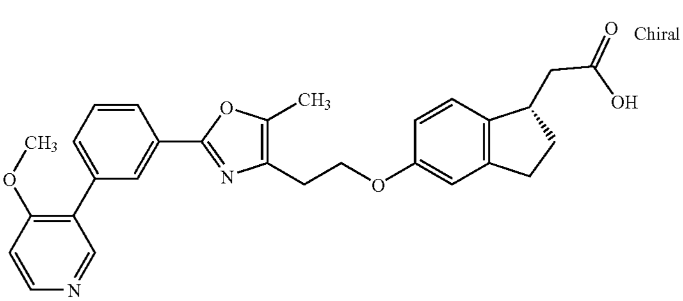 | 3.04 | 485.3 |

TABLE 3-continued
| Example No. | Structure | EI-MS [M + H]+ | HPLC RT (min) |
|---|---|---|---|
| 223 | 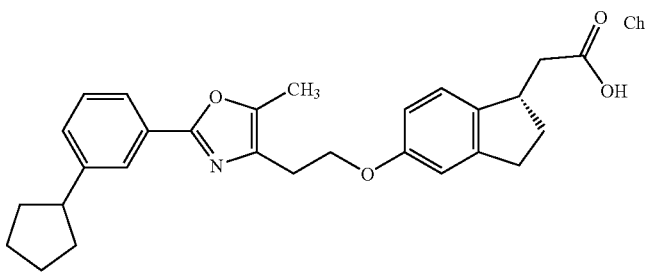 | 4.63 | 446.4 |
| 224 | 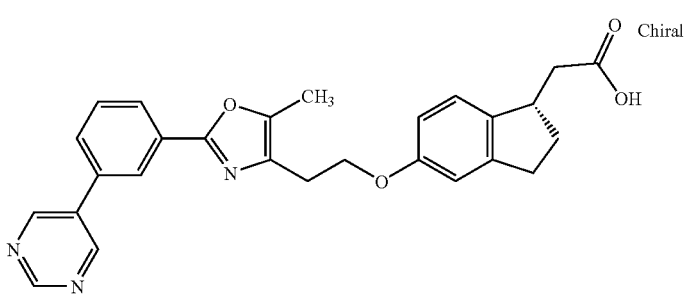 | 3.61 | 456.3 |
| 225 | 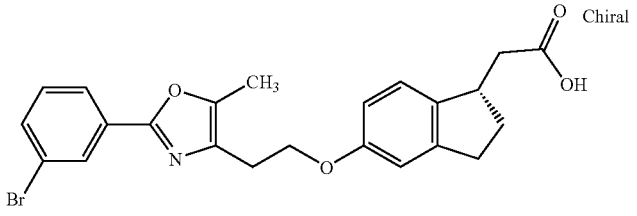 | 4.3 | 456.3 |
| 226 | 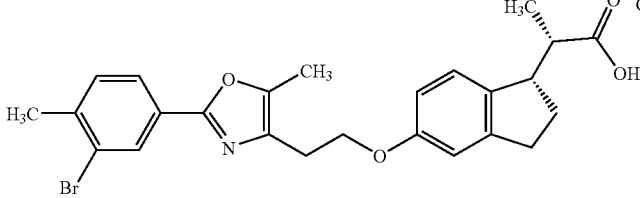 | 4.38 | 484.3 |
| 227 | 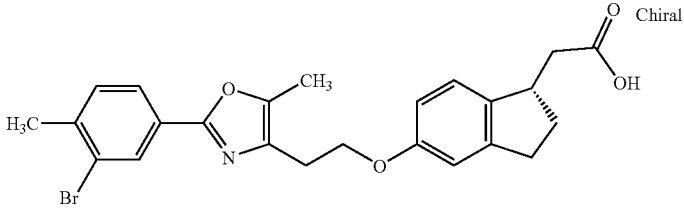 | 3.82 | 470.1 |
| 228 | 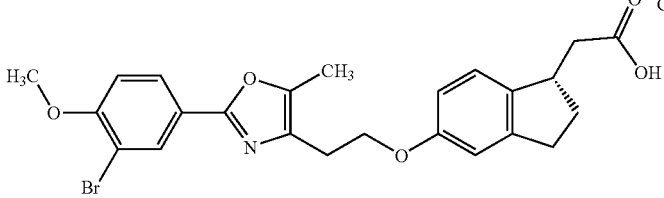 | 3.56 | 486.3 |

TABLE 3-continued

| Example No. | Structure | EI-MS [M + H]+ | HPLC RT (min) |
|---|---|---|---|
| 229 | 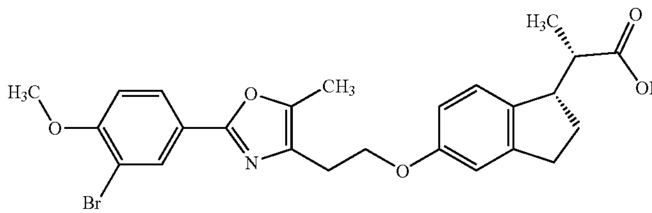 | 3.67 | 500.3 |
| 230 | 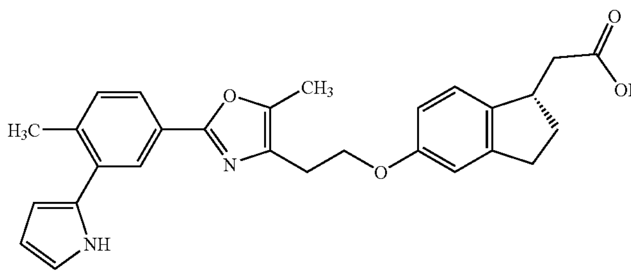 | 3.57 | 457.5 |
| 231 | 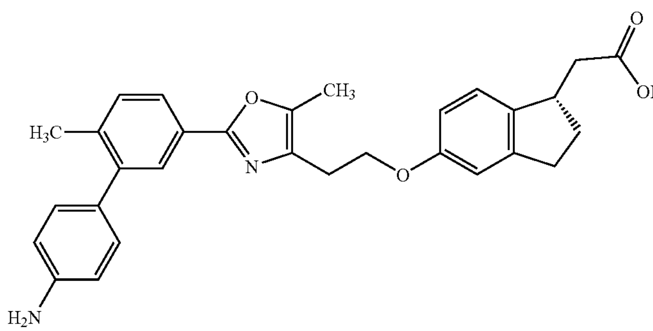 | 3.13 | 483.4 |
| 232 | 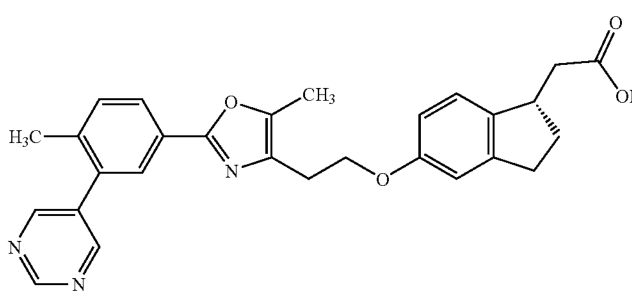 | 3.27 | 470.4 |
| 233 | 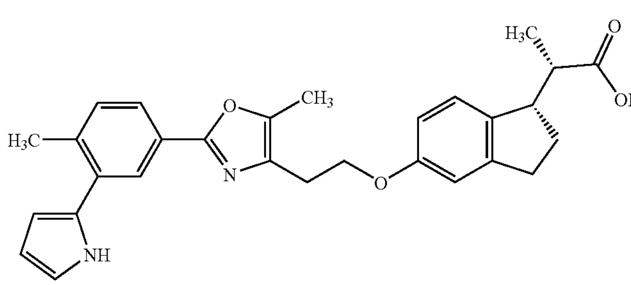 | 3.48 | 471.4 |

TABLE 3-continued

| Example No. | Structure | EI-MS [M + H]+ | HPLC RT (min) |
| --- | --- | --- | --- |
| 234 | 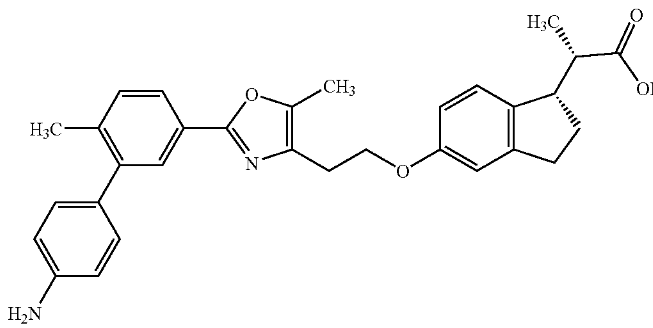 | 3.14 | 497.4 |
| 235 | 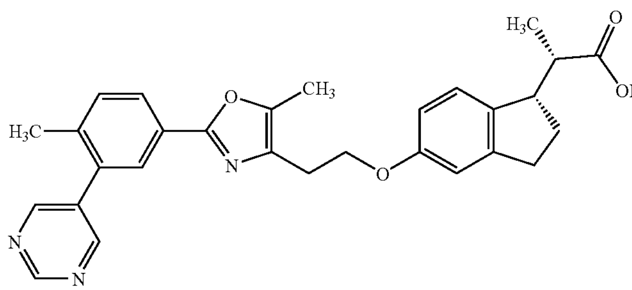 | 3.27 | 484.4 |
| 236 | 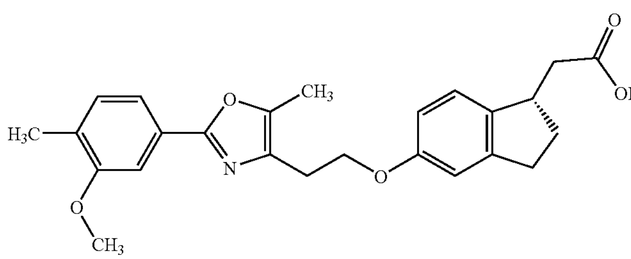 | 3.9 | 422.4 |
| 237 | 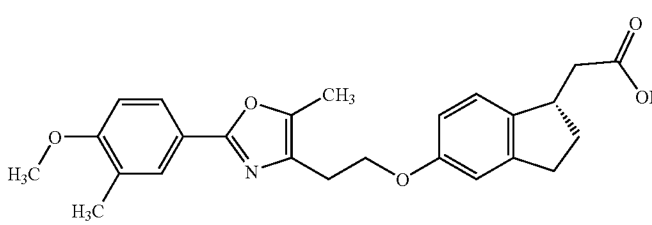 | 3.84 | 422.4 |
| 238 | 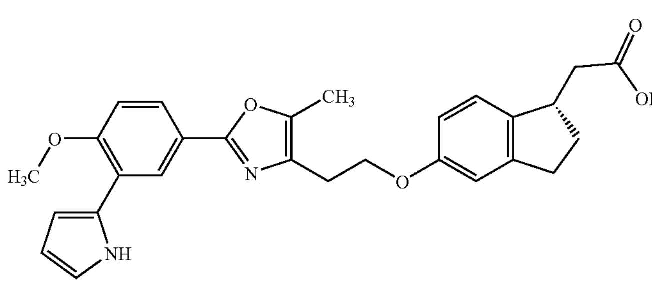 | 3.79 | 473.4 |

TABLE 3-continued
| Example No. | Structure | EI-MS [M + H]+ | HPLC RT (min) |
|---|---|---|---|
| 239 | 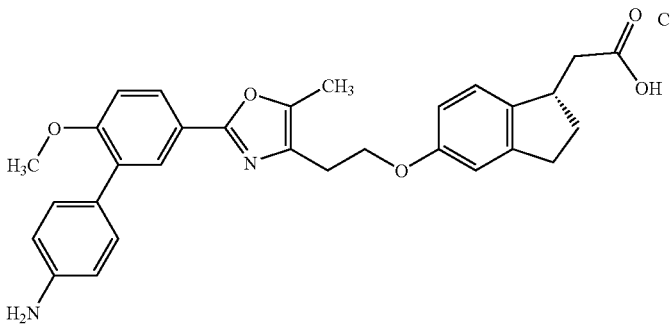 | 3.09 | 499.3 |
| 240 | 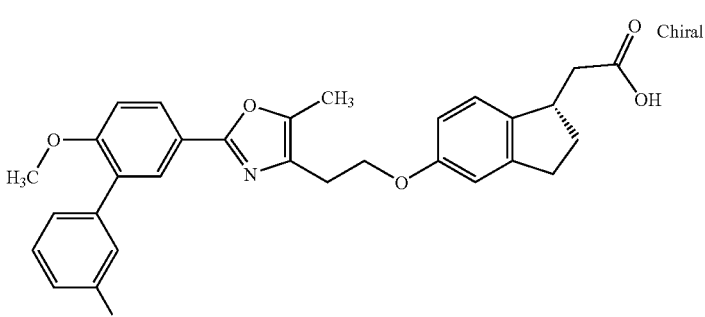 | 3.09 | 499.3 |
| 241 | 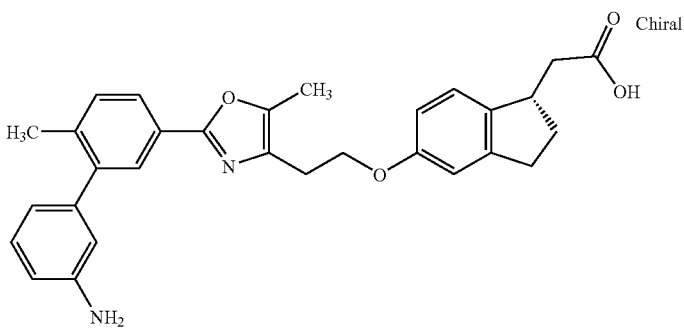 | 3.26 | 483.4 |
| 242 | 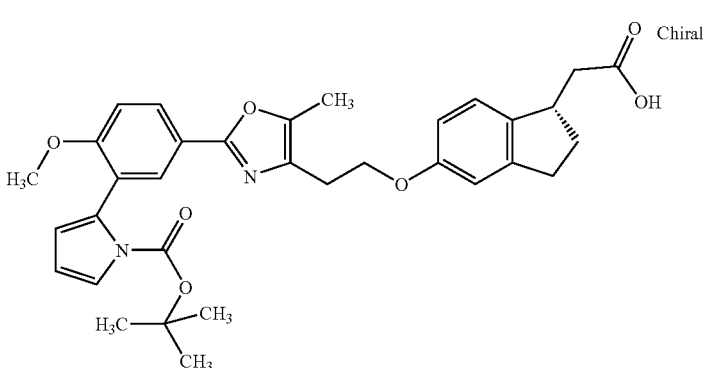 | 4.19 | 573.2 |

TABLE 4

| Example No. | IUPAC NAME |
|---|---|
| 204 | [(1S)-5-(2-{5-methyl-2-[4-(5-pyrimidinyl)phenyl]-1,3-oxazol-4-yl}ethoxy)-2,3-dihydro-1H-inden-1-yl]acetic acid |
| 205 | {(1S)-5-[2-(2-{4-[1-(tert-butoxycarbonyl)-1H-pyrrol-2-yl]phenyl}-5-methyl-1,3-oxazol-4-yl)ethoxy]-2,3-dihydro-1H-inden-1-yl}acetic acid |
| 206 | [(1S)-5-(2-{2-[4-(3,5-dimethyl-4-isoxazolyl)phenyl]-5-methyl-1,3-oxazol-4-yl}ethoxy)-2,3-dihydro-1H-inden-1-yl]acetic acid |
| 207 | [(1S)-5-(2-{5-methyl-2-[4-(3-pyridinyl)phenyl]-1,3-oxazol-4-yl}ethoxy)-2,3-dihydro-1H-inden-1-yl]acetic acid |
| 208 | [(1S)-5-(2-{5-methyl-2-[4-(4-pyridinyl)phenyl]-1,3-oxazol-4-yl}ethoxy)-2,3-dihydro-1H-inden-1-yl]acetic acid |
| 209 | 4'-[4-(2-{[(1S)-1-(carboxymethyl)-2,3-dihydro-1H-inden-5-yl]oxy}ethyl)-5-methyl-1,3-oxazol-2-yl]-1,1'-biphenyl-4-carboxylic acid |
| 210 | ((1S)-5-{2-[5-methyl-2-(3'-nitro-1,1'-biphenyl-4-yl)-1,3-oxazol-4-yl]ethoxy}-2,3-dihydro-1H-inden-1-yl)acetic acid |
| 211 | [(1S)-5-(2-{5-methyl-2-[4-(1H-pyrrol-2-yl)phenyl]-1,3-oxazol-4-yl}ethoxy)-2,3-dihydro-1H-inden-1-yl]acetic acid |
| 212 | ((1S)-5-{2-[2-(3'-acetyl-1,1'-biphenyl-4-yl)-5-methyl-1,3-oxazol-4-yl]ethoxy}-2,3-dihydro-1H-inden-1-yl)acetic acid |
| 213 | [(1S)-5-(2-{2-[4-(1,3-benzodioxol-5-yl)phenyl]-5-methyl-1,3-oxazol-4-yl}ethoxy)-2,3-dihydro-1H-inden-1-yl]acetic acid |
| 214 | [(1S)-5-(2-{5-methyl-2-[3-(4-pyridinyl)phenyl]-1,3-oxazol-4-yl}ethoxy)-2,3-dihydro-1H-inden-1-yl]acetic acid |
| 215 | [(1S)-5-(2-{5-methyl-2-[3-(3-pyridinyl)phenyl]-1,3-oxazol-4-yl}ethoxy)-2,3-dihydro-1H-inden-1-yl]acetic acid |
| 216 | [(1S)-5-(2-{2-[3-(2,4-dimethoxy-5-pyrimidinyl)phenyl]-5-methyl-1,3-oxazol-4-yl}ethoxy)-2,3-dihydro-1H-inden-1-yl]acetic acid |
| 217 | [(1S)-5-(2-{2-[3-(3,5-dimethyl-4-isoxazolyl)phenyl]-5-methyl-1,3-oxazol-4-yl}ethoxy)-2,3-dihydro-1H-inden-1-yl]acetic acid |
| 218 | [(1S)-5-(2-{2-[4'-(hydroxymethyl)-1,1'-biphenyl-3-yl]-5-methyl-1,3-oxazol-4-yl}ethoxy)-2,3-dihydro-1H-inden-1-yl]acetic acid |
| 219 | ((1S)-5-{2-[2-(4'-amino-1,1'-biphenyl-3-yl)-5-methyl-1,3-oxazol-4-yl]ethoxy}-2,3-dihydro-1H-inden-1-yl)acetic acid |
| 220 | [(1S)-5-(2-{2-[3-(1,3-benzodioxol-5-yl)phenyl]-5-methyl-1,3-oxazol-4-yl}ethoxy)-2,3-dihydro-1H-inden-1-yl]acetic acid |
| 221 | [(1S)-5-(2-{2-[3-(5-acetyl-2-thienyl)phenyl]-5-methyl-1,3-oxazol-4-yl}ethoxy)-2,3-dihydro-1H-inden-1-yl]acetic acid |
| 222 | [(1S)-5-(2-{2-[3-(4-methoxy-3-pyridinyl)phenyl]-5-methyl-1,3-oxazol-4-yl}ethoxy)-2,3-dihydro-1H-inden-1-yl]acetic acid |
| 223 | ((1S)-5-{2-[2-(3-cyclopentylphenyl)-5-methyl-1,3-oxazol-4-yl]ethoxy}-2,3-dihydro-1H-inden-1-yl)acetic acid |
| 224 | [(1S)-5-(2-{5-methyl-2-[3-(5-pyrimidinyl)phenyl]-1,3-oxazol-4-yl}ethoxy)-2,3-dihydro-1H-inden-1-yl]acetic acid |
| 225 | ((1S)-5-{2-[2-(3-bromophenyl)-5-methyl-1,3-oxazol-4-yl]ethoxy}-2,3-dihydro-1H-inden-1-yl)acetic acid |
| 226 | (2S)-2-((1S)-5-{2-[2-(3-bromo-4-methylphenyl)-5-methyl-1,3-oxazol-4-yl]ethoxy}-2,3-dihydro-1H-inden-1-yl)propanoic acid |
| 227 | ((1S)-5-{2-[2-(3-bromo-4-methylphenyl)-5-methyl-1,3-oxazol-4-yl]ethoxy}-2,3-dihydro-1H-inden-1-yl)acetic acid |
| 228 | ((1S)-5-{2-[2-(3-bromo-4-methoxyphenyl)-5-methyl-1,3-oxazol-4-yl]ethoxy}-2,3-dihydro-1H-inden-1-yl)acetic acid |
| 229 | (2S)-2-((1S)-5-{2-[2-(3-bromo-4-methoxyphenyl)-5-methyl-1,3-oxazol-4-yl]ethoxy}-2,3-dihydro-1H-inden-1-yl)propanoic acid |
| 230 | [(1S)-5-(2-{5-methyl-2-[4-methyl-3-(1H-pyrrol-2-yl)phenyl]-1,3-oxazol-4-yl}ethoxy)-2,3-dihydro-1H-inden-1-yl]acetic acid |
| 231 | ((1S)-5-{2-[2-(4'-amino-6-methyl-1,1'-biphenyl-3-yl)-5-methyl-1,3-oxazol-4-yl]ethoxy}-2,3-dihydro-1H-inden-1-yl)acetic acid |
| 232 | [(1S)-5-(2-{5-methyl-2-[4-methyl-3-(5-pyrimidinyl)phenyl]-1,3-oxazol-4-yl}ethoxy)-2,3-dihydro-1H-inden-1-yl]acetic acid |
| 233 | (2S)-2-[(1S)-5-(2-{5-methyl-2-[4-methyl-3-(1H-pyrrol-2-yl)phenyl]-1,3-oxazol-4-yl}ethoxy)-2,3-dihydro-1H-inden-1-yl]propanoic acid |
| 234 | (2S)-2-((1S)-5-{2-[2-(4'-amino-6-methyl-1,1'-biphenyl-3-yl)-5-methyl-1,3-oxazol-4-yl]ethoxy}-2,3-dihydro-1H-inden-1-yl)propanoic acid |
| 235 | (2S)-2-[(1S)-5-(2-{5-methyl-2-[4-methyl-3-(5-pyrimidinyl)phenyl]-1,3-oxazol-4-yl}ethoxy)-2,3-dihydro-1H-inden-1-yl]propanoic acid |
| 236 | ((1S)-5-{2-[2-(3-methoxy-4-methylphenyl)-5-methyl-1,3-oxazol-4-yl]ethoxy}-2,3-dihydro-1H-inden-1-yl)acetic acid |
| 237 | ((1S)-5-{2-[2-(4-methoxy-3-methylphenyl)-5-methyl-1,3-oxazol-4-yl]ethoxy}-2,3-dihydro-1H-inden-1-yl)acetic acid |
| 238 | [(1S)-5-(2-{2-[4-methoxy-3-(1H-pyrrol-2-yl)phenyl]-5-methyl-1,3-oxazol-4-yl}ethoxy)-2,3-dihydro-1H-inden-1-yl]acetic acid |
| 239 | ((1S)-5-{2-[2-(4'-amino-6-methoxy-1,1'-biphenyl-3-yl)-5-methyl-1,3-oxazol-4-yl]ethoxy}-2,3-dihydro-1H-inden-1-yl)acetic acid |
| 240 | ((1S)-5-{2-[2-(3'-amino-6-methoxy-1,1'-biphenyl-3-yl)-5-methyl-1,3-oxazol-4-yl]ethoxy}-2,3-dihydro-1H-inden-1-yl)acetic acid |

TABLE 4-continued

| Example No. | IUPAC NAME |
|---|---|
| 241 | ((1S)-5-{2-[2-(3'-amino-6-methyl-1,1'-biphenyl-3-yl)-5-methyl-1,3-oxazol-4-yl]ethoxy}-2,3-dihydro-1H-inden-1-yl)acetic acid |
| 242 | {(1S)-5-[2-(2-{3-[1-(tert-butoxycarbonyl)-1H-pyrrol-2-yl]-4-methoxyphenyl}-5-methyl-1,3-oxazol-4-yl)ethoxy]-2,3-dihydro-1H-inden-1-yl}acetic acid |

The compounds of Formula (I) are effective in the treatment of Type II diabetes mellitus (including associated diabetic dyslipidemia and other diabetic complications), as well as a number of other pharmaceutical uses associated therewith, such as hyperglycemia, hyperinsulinemia, impaired glucose tolerance, impaired fasting glucose, dyslipidemia, hypertriglyceridemia, Syndrome X, and insulin resistance. In addition, the compounds of the present invention are also effective in the regulation of appetite and food intake in such disorders as obesity, and in the treatment of atherosclerotic disease, hyperlipidemia, hypercholesteremia, low HDL levels, hypertension, cardiovascular disease (including atherosclerosis, coronary heart disease, coronary artery disease, and hypertension, cerebrovascular disease and peripheral vessel disease; and for the treatment of lupus, polycystic ovary syndrome, carcinogenesis, and hyperplasia. The compounds of Formula (I) are also useful for treating physiological disorders related to, for example, cell differentiation to produce lipid accumulating cells, regulation of insulin sensitivity and blood glucose levels, which are involved in, for example, abnormal pancreatic beta cell function, insulin secreting tumors and/or autoimmune hypoglycemia due to autoantibodies to insulin, autoantibodies to the insulin receptor, or autoantibodies that are stimulatory to pancreatic beta cells), macrophage differentiation which leads to the formation of atherosclerotic plaques, inflammatory response, carcinogenesis, hyperplasia, adipocyte gene expression, adipocyte differentiation, reduction in the pancreatic β-cell mass, insulin secretion, tissue sensitivity to insulin, liposarcoma cell growth, polycystic ovarian disease, chronic anovulation, hyperandrogenism, progesterone production, steroidogenesis, redox potential and oxidative stress in cells, nitric oxide synthase (NOS) production, increased gamma glutamyl transpeptidase, catalase, plasma triglycerides, HDL, and LDL cholesterol levels, and the like.

Particularly useful compounds of Formula (I) of the present invention are those with efficacy in lowering blood glucose concentration and serum triglyceride levels, and raising serum HDL cholesterol levels.

Therefore, the compounds of Formula (I) of this invention are expected to be valuable as therapeutic agents. Accordingly, an embodiment of this invention includes a method of treating the various conditions identified above in a patient (including mammals) which comprises administering to said patient a composition containing an amount of the compound of Formula (I) that is effective in treating the target condition.

As indicated above, a compound of Formula (I) may be administered alone or in combination with one or more additional hypoglycemic agents. Combination therapy includes administration of a single pharmaceutical dosage formulation which contains a compound of Formula (I) and one or more additional hypoglycemic agent, as well as administration of the compound of Formula (I) and each additional hypoglycemic agents in its own separate pharmaceutical dosage formulation. For example, a compound of Formula (I) and hypoglycemic agent may be administered to the patient together in a single oral dosage composition such as a tablet or capsule, or each agent may be administered in separate oral dosage formulations.

Where separate dosage formulations are used, the compound of Formula (I) and one or more additional hypoglycemic agents may be administered at essentially the same time (e.g., concurrently) or at separately staggered times (e.g., sequentially).

For example, the compound of Formula (I) may be administered in combination with one or more of the following additional hypoglycemic agents: insulin; biguanidines such as metformin or buformin; sulfonylureas such as acetohexamide, chloropropamide, tolazamide, tolbutamide, glyburide, glipizide, glyclazide; or any other insulin secretagogue such as, for example, repaglinide and nateglinide; α-glycosidase inhibitors such as acarbose, voglibose, or miglitol; or β$_3$-adrenoreceptor agonists such as CL-316,243.

The compounds of Formula (I) may also be utilized, in free base form or in compositions, as well as in research and diagnostics or as analytical reference standards, and the like, which are well known in the art. Therefore, the present invention includes compositions which are comprised of an inert carrier and an effective amount of a compound of Formula (I), or a salt, or ester thereof. An inert carrier is any material which does not interact with the compound to be carried and which lends support, means of conveyance, bulk, traceable material, and the like to the compound to be carried. An effective amount of the compound is that amount which produces a result or exerts an influence on the particular procedure being performed.

In another aspect, the present invention provides a method for treating a disease state in a patient, wherein the disease is associated with a physiological detrimental level of insulin, glucose, free fatty acids (FFA), cholesterol, or triglycerides in the blood, comprising administering to the patient a therapeutically effective amount of a compound of Formula (I). In a further embodiment, the present invention provides a method for treating a disease state in a patient, wherein the disease is associated with a physiological detrimental level of insulin, glucose, free fatty acids (FFA), or triglycerides in the blood, comprising administering to the patient a therapeutically effective amount of a compound of Formula (I) and also administering a therapeutically effective amount of an additional hypoglycemic agent such as, for example, insulin, a biguanidine compound, and the like.

Since sulfonylureas and other insulin secretagogues are known to be capable of stimulating insulin release, but are not capable of acting on insulin resistance, and compounds of Formula I are able to act on insulin resistance, it is envisaged that a combination of these medicaments may be used as a remedy for conditions associated with both deficiency in insulin secretion and insulin resistance. Therefore, the invention also provides a method of treating Type II diabetes mellitus in a patient comprising administering a compound of Formula (I) and one or more additional hypoglycemic agents such as, for example, sulfonylureas, biguanidines, β-adrenoreceptor agonists, α-glycosidase inhibitors, and insulin. Also, compounds of Formula (I) may be used in combination with HMG Co-A reductase inhibitors (statins), bile acid binding resin, or fibric acid derivatives to improve the lipid profile of subjects with dyslipidemia and insulin resistance. Compounds of Formula (I) may also be used in combination with agents that regulate hypertension (e.g., inhibitors of angiotension converting enzyme (ACE), β-blockers, calcium channel blockers) and body weight of subjects with insulin resistance or Type II diabetes.

Evaluation of Compounds

Demonstration of the activity of the compounds of the present invention may be accomplished through in vitro, ex vivo, and in vivo assays that are well known in the art. For example, to demonstrate the efficacy of a pharmaceutical agent for the treatment of diabetes and related disorders such as Syndrome X, impaired glucose tolerance, impaired fasting glucose, and hyperinsulinemia or atherosclerotic disease and related disorders such as hypertriglyceridemia and hypercholesteremia, the following assays may be used.

Insulin Receptor Binding in 3T3-L1 Cells Treated with Compounds

3T3-L1 cells were seeded at 9300 cells per well in Costar flat bottom TC and incubated for 1 week until they were 2 days post-confluent (e.g., cells have reached maximum density). The cells were then treated for 2 days with differentiation media (Dulbecco's Modified Eagle Medium (DMEM), 100 μg/ml Penicillin/Streptomycin, 2 mM L-Glutamine, 10% Fetal Bovine Serum) containing 0.5 μM human Insulin-like Growth Factor (IGF-1) and test compounds. After treatment, the media was replaced with differentiation media, and the cells were incubated for 4 days. The cells were then assayed for insulin receptor activity. After washing the cells with buffer, they were incubated with 0.1 nM $^{125}$I-insulin and (+/−) 100 nM unlabeled insulin, and incubated at rt for 1 hour. The cells were then washed 3× with buffer, dissolved with 1 N NaOH, and counted on a gamma counter. An EC50 value was determined if a plateau was attained and percent maximum stimulation was assessed.

In Vivo Assays

Method for Measuring Blood Glucose Levels db/db mice (obtained from Jackson Laboratories, Bar Harbor, Me.) were bled (by either eye or tail vein) and grouped according to equivalent mean blood glucose levels. They were dosed orally (by gavage in a pharmaceutically acceptable vehicle) with the test compound once daily for 14 days. At this point, the animals were bled again by eye or tail vein and blood glucose levels were determined. In each case, glucose levels were measured with a Glucometer Elite XL (Bayer Corporation, Elkhart, Ind.).

Method for Measuring Triglyceride Levels hApoA1 mice (obtained from Jackson Laboratories, Bar Harbor, Me.) were bled (by either eye or tail vein) and grouped according to equivalent mean serum triglyceride levels. They were dosed orally (by gavage in a pharmaceutically acceptable vehicle) with the test compound once daily for 8 days. The animals were then bled again by eye or tail vein, and serum triglyceride levels were determined. In each case, triglyceride levels were measured using a Technicon Axon Autoanalyzer (Bayer Corporation, Tarrytown, N.Y.).

Method for Measuring HDL-Cholesterol Levels

To determine plasma HDL-cholesterol levels, hApoA1 mice are bled and grouped with equivalent mean plasma HDL-cholesterol levels. The mice are orally dosed once daily with vehicle or test compound for 7 days, and then bled again on day 8. Plasma is analyzed for HDL-cholesterol using the Synchron Clinical System (C×4) (Beckman Coulter, Fullerton, Calif.).

Method for Measuring Total Cholesterol, HDL-Cholesterol, Triglycerides, and Glucose Levels In another in vivo assay, obese monkeys are bled, then orally dosed once daily with vehicle or test compound for 4 weeks, and then bled again. Serum is analyzed for total cholesterol, HDL-cholesterol, triglycerides, and glucose using the Synchron Clinical System (C×4) (Beckman Coulter, Fullerton, Calif.). Lipoprotein subclass analysis is performed by NMR spectroscopy as described by Oliver et al., (Proc. Natl. Acad. Sci. USA 98:5306-5311, 2001).

Method for Measuring an Effect on Cardiovascular Parameters

Cardiovascular parameters (e.g., heart rate and blood pressure) are also evaluated. SHR rats are orally dosed once daily with vehicle or test compound for 2 weeks. Blood pressure and heart rate are determined using a tail-cuff method as described by Grinsell et al., (Am. J. Hypertens. 13:370-375, 2000). In monkeys, blood pressure and heart rate are monitored as described by Shen et al., (J. Pharmacol. Exp. Therap. 278:1435-1443,1996).

Compounds of the present invention were tested in the above assays and by the resulting activity profiles, they were found to have an effect on blood glucose levels and serum triglyceride levels, and therefore, a potential utility in the treatment of diabetes and related disorders such as Syndrome X, impaired glucose tolerance, impaired fasting glucose, and hyperinsulinemia or cardiovascular disease and related disorders such as hypertriglyceridemia and hypercholesteremia.

Pharmaceutical Compositions

Based on the above tests, or other well known assays used to determine the efficacy for treatment of conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered may generally range from about 0.001 mg/kg to about 200 mg/kg, and preferably from about 0.01 mg/kg to about 200 mg/kg body weight per day. A unit dosage may contain from about 0.05 mg to about 1500 mg of active ingredient, and may be administered one or more times per day. The daily dosage for administration by injection, including intravenous, intramuscular, subcutaneous, and parenteral injections, and use of infusion techniques may be from about 0.01 to about 200 mg/kg. The daily rectal dosage regimen may be from 0.01 to 200 mg/kg of total body weight. The transdermal concentration may be that required to maintain a daily dose of from 0.01 to 200 mg/kg.

Of course, the specific initial and continuing dosage regimen for each patient will vary according to the nature and severity of the condition as determined by the attending diagnostician, the activity of the specific compound employed, the age of the patient, the diet of the patient, time of administration, route of administration, rate of excretion of the drug, drug combinations, and the like. The desired mode of treatment and number of doses of a compound of the present invention or a pharmaceutically acceptable salt thereof may be ascertained by those skilled in the art using conventional treatment tests.

The compounds of this invention may be utilized to achieve the desired pharmacological effect by administration to a patient in need thereof in an appropriately formulated pharmaceutical composition. A patient, for the purpose of this invention, is a mammal, including a human, in need of treatment for a particular condition or disease. Therefore, the present invention includes pharmaceutical compositions which are comprised of a pharmaceutically acceptable carrier and a pharmaceutically effective amount of a compound identified by the methods described herein, or a pharmaceutically acceptable salt or ester thereof. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of a compound is that amount which produces a result or exerts an influence on the particular condition being treated. The compounds identified by the methods described herein may be administered with a pharmaceutically-acceptable carrier using any effective conventional dosage unit forms, including, for example, immediate and timed release preparations, orally, parenterally, topically, or the like.

For oral administration, the compounds may be formulated into solid or liquid preparations such as, for example, capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil, or coconut oil; or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring and coloring agents.

The compounds of this invention may also be administered parenterally, that is, subcutaneously, intravenously, intramuscularly, or interperitoneally, as injectable dosages of the compound in a physiologically acceptable diluent with a pharmaceutical carrier which may be a sterile liquid or mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,1-dioxolane-4-methanol, ethers such as poly(ethyleneglycol) 400; an oil; a fatty acid; a fatty acid ester or glyceride; or an acetylated fatty acid glyceride with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention may typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A composition of the invention may also be administered in the form of suppositories for rectal administration of the drug. These compositions may be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. For example, direct techniques for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, incorporated herein by reference.

The compositions of the invention may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

Commonly used pharmaceutical ingredients which may be used as appropriate to formulate the composition for its intended route of administration include: acidifying agents, for example, but are not limited to, acetic acid, citric acid, fumaric acid, hydrochloric acid, nitric acid; and alkalinizing agents such as, but are not limited to, ammonia solution, ammonium carbonate, diethanolamine, monoethanolamine, potassium hydroxide, sodium borate, sodium carbonate, sodium hydroxide, triethanolamine, trolamine.

Other pharmaceutical ingredients include, for example, but are not limited to, adsorbents (e.g., powdered cellulose and activated charcoal); aerosol propellants (e.g., carbon dioxide, $CCl_2F_2$, $F_2ClC—CClF_2$ and $CClF_3$); air displacement agents (e.g., nitrogen and argon); antifungal preservatives (e.g., benzoic acid, butylparaben, ethylparaben, methylparaben, propylparaben, sodium benzoate); antimicrobial preservatives (e.g., benzalkonium chloride, benzethonium chloride, benzyl alcohol, cetylpyridinium chloride, chlorobutanol, phenol, phenylethyl alcohol, phenylmercuric nitrate and thimerosal); antioxidants (e.g., ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite); binding materials (e.g., block polymers, natural and synthetic rubber, polyacrylates, polyurethanes, silicones and styrene-butadiene copolymers); buffering agents (e.g., potassium metaphosphate, potassium phosphate monobasic, sodium acetate, sodium citrate anhydrous and sodium citrate dihydrate); carrying agents (e.g., acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection); chelating agents (e.g., edetate disodium and edetic acid); colorants (e.g., FD&C Red No. 3, FD&C Red No. 20, FD&C Yellow No. 6, FD&C Blue No. 2, D&C Green No. 5, D&C Orange No. 5, D&C Red No. 8, caramel and ferric oxide red); clarifying agents (e.g., bentonite); emulsifying agents (but are not limited to, acacia, cetomacrogol, cetyl alcohol, glyceryl monostearate, lecithin, sorbitan monooleate, polyethylene 50 stearate); encapsulating agents (e.g., gelatin and cellulose acetate phthalate); flavorants (e.g., anise oil, cinnamon oil, cocoa, menthol, orange oil, peppermint oil and vanillin); humectants (e.g., glycerin, propylene glycol and sorbitol); levigating agents (e.g., mineral oil and glycerin); oils (e.g., arachis oil, mineral oil, olive oil, peanut oil, sesame oil and vegetable oil); ointment bases (e.g., lanolin, hydrophilic ointment, polyethylene glycol ointment, petrolatum, hydrophilic petrolatum, white ointment, yellow ointment, and rose water ointment); penetration enhancers (transdermal delivery) (e.g., monohydroxy or polyhydroxy alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas);

plasticizers (e.g., diethyl phthalate and glycerin); solvents (e.g., alcohol, corn oil, cottonseed oil, glycerin, isopropyl alcohol, mineral oil, oleic acid, peanut oil, purified water, water for injection, sterile water for injection and sterile water for irrigation); stiffening agents (e.g., cetyl alcohol, cetyl esters wax, microcrystalline wax, paraffin, stearyl alcohol, white wax and yellow wax); suppository bases (e.g., cocoa butter and polyethylene glycols (mixtures)); surfactants (e.g., benzalkonium chloride, nonoxynol 10, oxtoxynol 9, polysorbate 80, sodium lauryl sulfate and sorbitan monopalmitate); suspending agents (e.g., agar, bentonite, carbomers, carboxymethylcellulose sodium, hydroxyethyl cellulose, hydroxypropyl cellulose, hydroxypropyl methylcellulose, kaolin, methylcellulose, tragacanth and veegum); sweetening e.g., aspartame, dextrose, glycerin, mannitol, propylene glycol, saccharin sodium, sorbitol and sucrose); tablet anti-adherents (e.g., magnesium stearate and talc); tablet binders (e.g., acacia, alginic acid, carboxymethylcellulose sodium, compressible sugar, ethylcellulose, gelatin, liquid glucose, methylcellulose, povidone and pregelatinized starch); tablet and capsule diluents (e.g., dibasic calcium phosphate, kaolin, lactose, mannitol, microcrystalline cellulose, powdered cellulose, precipitated calcium carbonate, sodium carbonate, sodium phosphate, sorbitol and starch); tablet coating agents (e.g., liquid glucose, hydroxyethyl cellulose, hydroxypropyl cellulose, hydroxypropyl methylcellulose, methylcellulose, ethylcellulose, cellulose acetate phthalate and shellac); tablet direct compression excipients (e.g., dibasic calcium phosphate); tablet disintegrants (e.g., alginic acid, carboxymethylcellulose calcium, microcrystalline cellulose, polacrillin potassium, sodium alginate, sodium starch glycoliate and starch); tablet glidants (e.g., colloidal silica, corn starch and talc); tablet lubricants (e.g., calcium stearate, magnesium stearate, mineral oil, stearic acid and zinc stearate); tablet/capsule opaquants (e.g., titanium dioxide); tablet polishing agents (e.g., carnuba wax and white wax); thickening agents (e.g., beeswax, cetyl alcohol and paraffin); tonicity agents (e.g., dextrose and sodium chloride); viscosity increasing agents (e.g., alginic acid, bentonite, carbomers, carboxymethylcellulose sodium, methylcellulose, povidone, sodium alginate and tragacanth); and wetting agents (e.g., heptadecaethylene oxycetanol, lecithins, polyethylene sorbitol monooleate, polyoxyethylene sorbitol monooleate, and polyoxyethylene stearate).

The compounds identified by the methods described herein may be administered as the sole pharmaceutical agent or in combination with one or more other pharmaceutical agents where the combination causes no unacceptable adverse effects. For example, the compounds of this invention can be combined with known anti-obesity, or with known antidiabetic or other indication agents, and the like, as well as with admixtures and combinations thereof.

The compounds identified by the methods described herein may also be utilized, in free base form or in compositions, in research and diagnostics, or as analytical reference standards, and the like. Therefore, the present invention includes compositions which are comprised of an inert carrier and an effective amount of a compound identified by the methods described herein, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

Formulations suitable for subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., 20$^{th}$ edition, 2000).

The following examples are presented to illustrate the invention described herein, but should not be construed as limiting the scope of the invention in any way.

Capsule Formulation

A capsule formula is prepared from:

| | |
|---|---|
| Compound of this invention | 40 mg |
| Starch | 109 mg |
| Magnesium stearate | 1 mg |

The components are blended, passed through an appropriate mesh sieve, and filled into hard gelatin capsules.

Tablet Formulation

A tablet is prepared from:

| | |
|---|---|
| Compound of this invention | 25 mg |
| Cellulose, microcrystaline | 200 mg |
| Colloidal silicon dioxide | 10 mg |
| Stearic acid | 5.0 mg |

The ingredients are mixed and compressed to form tablets. Appropriate aqueous and non-aqueous coatings may be applied to increase palatability, improve elegance and stability or delay absorption.

Sterile IV Solution

A 5 mg/ml solution of the desired compound of this invention is made using sterile, injectable water, and the pH is adjusted if necessary. The solution is diluted for administration to 1-2 mg/ml with sterile 5% dextrose and is administered as an IV infusion over 60 minutes.

Intramuscular Suspension

The following intramuscular suspension is prepared:

| | |
|---|---|
| Compound of this invention | 50 mg/ml |
| Sodium carboxymethylcellulose | 5 mg/ml |
| TWEEN 80 | 4 mg/ml |
| Sodium chloride | 9 mg/ml |
| Benzyl alcohol | 9 mg/ml |

The suspension is administered intramuscularly.

Hard Shell Capsules

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

It should be apparent to one of ordinary skill in the art that changes and modifications can be made to this invention without departing from the spirit or scope of the invention as it is set forth herein.

We claim:

1. A compound of Formula (I),

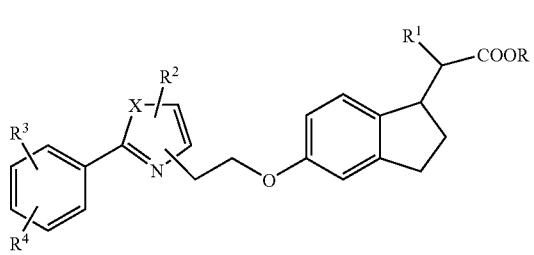

wherein
R and $R^1$ is H or $C_1$-$C_6$ alkyl;
$R^2$ is H, $C_1$-$C_6$ alkyl, or phenyl which may be unsubstituted or substituted with $R^3$;
$R^3$ is H, halo, $NO_2$, $CF_3$, 2,3-methylenedioxy, 3,4-methylenedioxy, $C_1$-$C_6$ alkylthio,
$C_1$-$C_6$ alkyl optionally substituted with oxo or hydroxy, $C_1$-$C_6$ alkoxy optionally substituted with fluoro, or —COOH or —COO$C_1$-$C_6$ alkyl.
$R^4$ is NH(Y—$R^6$) or N(Y—$R^6$)$_2$;
Y is a bond, —SO$_2$—, or —C(O)—;
$R^6$ is H, aryl, benzyl, $C_1$-$C_6$ alkoxyalkyl, $C_1$-$C_6$ alkyl, or heteroaryl, each of which can be substituted by $R^3$, or
when Y is a bond, two $R^6$ groups may form, together with the N atom to which they are attached, a 3-7 membered heterocyclic ring optionally containing an additional N, S, or O atom, which is optionally substituted by N($R^7$)$_2$ or N$^+$($R^5$)$_3$, and
$R^5$ is $C_1$-$C_6$ alkyl optionally substituted with phenyl,
$R^7$ is H, $C_1$-$C_6$ alkyl or phenyl substituted with $R^3$; and
X is O;
or a pharmaceutically acceptable salt or ester thereof.

2. The compound of claim 1, wherein R, $R^1$, $R_2$, and $R^3$, are defined as in claim 1;
$R^4$ is NH(Y—$R^6$) or N(Y—$R^6$)$_2$,
Y is a bond,
$R^6$ is aryl, benzyl, $C_1$-$C_6$ alkoxyalkyl, $C_1$-$C_6$ alkyl, or heteroaryl, each of which can be substituted by $R^3$, or
two $R^6$ groups may form, together with the N atom to which they are attached, a 3-7 membered heterocyclic ring optionally containing an additional N, S, or O atom, which is optionally substituted by N($R^7$)$_2$ or N$^+$($R^5$)$_3$, and
$R^7$ is H, $C_1$-$C_6$ alkyl or phenyl substituted with $R^3$; and
X is O.

3. The compound of claim 1, wherein R, $R^1$, $R_2$, and $R^3$, are defined as in claim 1;
$R^4$ is NH(Y—$R^6$) or N(Y—$R^6$)$_2$,
Y is —SO$_2$—,
$R^6$ is H, aryl, benzyl, $C_1$-$C_6$ alkoxyalkyl, $C_1$-$C_6$ alkyl, or heteroaryl, each of which can be substituted by $R^3$, and
$R^7$ is H, $C_1$-$C_6$ alkyl or phenyl substituted with $R^3$, and
X is O.

4. The compound of claim 1, wherein R, $R^1$, $R^2$, and $R^3$, are defined as in claim 1;
$R^4$ is NH(Y—$R^6$) or N(Y—$R^6$)$_2$,
Y is —C(O)—,
$R^6$ is H, aryl, benzyl, $C_1$-$C_6$ alkoxyalkyl, $C_1$-$C_6$ alkyl, or heteroaryl, each of which can be substituted by $R^3$, and
$R^7$ is H, $C_1$-$C_6$ alkyl or phenyl substituted with $R^3$, and
X is O.

5. A pharmaceutical composition comprising an effective amount of a compound of claim 1, or a pharmaceutically acceptable salt or ester thereof, in combination with a pharmaceutically acceptable carrier.

6. A pharmaceutical composition comprising an effective amount of a compound of claim 1, or a pharmaceutically acceptable salt or ester thereof, in combination with a pharmaceutically acceptable carrier and one or more hypoglycemic agents.

7. The pharmaceutical composition of claim 6, wherein said hypoglycemic agent is selected from the group consisting of insulin, biguanidines, sulfonylureas, insulin secretagogues, α-glycosidase inhibitors, and β$_3$-adrenoreceptor agonists.

8. A method of treating diabetes or diabetes-related disorders selected from the group consisting of hyperglycemia, hyperinsulinemia, impaired glucose tolerance, impaired fasting glucose, dyslipidemia, hypertriglyceridemia, and insulin resistance comprising the step of administering to a patient in need thereof a pharmaceutically effective amount of a compound of claim 1.

9. A method of treating Syndrome X comprising the step of administering to a patient in need thereof a pharmaceutically effective amount of a compound of claim 1.

10. A method of treating obesity comprising the step of administering to a patient in need thereof a pharmaceutically effective amount of a compound of claim 1.

11. A method of treating cardiovascular disease selected from the group consisting of atherosclerotic disease, dyslipidemia, hypercholesterolemia, decreased HDL levels, hypertension, coronary heart disease, and coronary artery disease comprising the step of administering to a patient in need thereof a pharmaceutically effective amount of a compound of claim 1.

12. A method of treating diabetes or diabetes-related disorders selected from the group consisting of hyperglycemia, hyperinsulinemia, impaired glucose tolerance, impaired fasting glucose, dyslipidemia, hypertriglyceridemia, and insulin resistance comprising the step of administering to a patient in need thereof a pharmaceutically effective amount of a compound of claim 1 in combination with one or more hypoglycemic agents.

13. A method of treating Syndrome X comprising the step of administering to a patient in need thereof a pharmaceutically effective amount of a compound of claim 1 in combination with one or more hypoglycemic agents.

* * * * *

UNITED STATES PATENT AND TRADEMARK OFFICE
CERTIFICATE OF CORRECTION

| | | |
|---|---|---|
| PATENT NO. | : 7,476,742 B2 | Page 1 of 1 |
| APPLICATION NO. | : 10/506270 | |
| DATED | : January 13, 2009 | |
| INVENTOR(S) | : Wickens et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 814 days.

Signed and Sealed this
Twelfth Day of April, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,476,742 B2 | Page 1 of 1 |
| APPLICATION NO. | : 10/506270 | |
| DATED | : January 13, 2009 | |
| INVENTOR(S) | : Philip Wickens et al. | |

It is certified that error appears in the above-identified patent and that said Letters Patent is hereby corrected as shown below:

This certificate supersedes the Certificate of Correction issued April 12, 2011. The certificate is vacated since request for patent term adjustment under 37 CFR 1.705(d) has been dismissed by the Office of Petitions. The Certificate of Correction should not have been issued for this patent and the term of this patent is reinstated to be extended or adjusted under 35 U. S. C. 154(b) by --378 days--.

Signed and Sealed this
Twenty-third Day of August, 2011

David J. Kappos
*Director of the United States Patent and Trademark Office*